(12) United States Patent
Kozlowski et al.

(10) Patent No.: US 7,432,330 B2
(45) Date of Patent: Oct. 7, 2008

(54) HYDROLYTICALLY STABLE MALEIMIDE-TERMINATED POLYMERS

(75) Inventors: Antoni Kozlowski, Huntsville, AL (US); Remy F. Gross, III, Huntsville, AL (US); Samuel P. McManus, Brevard, NC (US)

(73) Assignee: Nektar Therapeutics AL, Corporation, Huntsville, AL (US)

( * ) Notice: Subject to any disclaimer, the term of this patent is extended or adjusted under 35 U.S.C. 154(b) by 410 days.

(21) Appl. No.: 10/751,274

(22) Filed: Dec. 31, 2003

(65) Prior Publication Data

US 2004/0204548 A1 Oct. 14, 2004

Related U.S. Application Data

(60) Provisional application No. 60/437,211, filed on Dec. 31, 2002.

(51) Int. Cl.
- C08C 19/20 (2006.01)
- C08F 8/34 (2006.01)
- C08G 65/326 (2006.01)
- A61K 47/48 (2006.01)
- C08C 19/22 (2006.01)
- C08F 8/32 (2006.01)
- C08G 65/325 (2006.01)

(52) U.S. Cl. .............. 525/343; 525/50; 525/54.1; 525/55; 525/56; 525/61; 525/326.7; 525/326.9; 525/327.2; 525/328.2; 525/328.8; 525/379; 525/403; 528/421; 528/487; 424/78.17

(58) Field of Classification Search .......... 525/50, 525/54.1, 55, 56, 61, 326.7, 326.9, 327.2, 525/328.2, 328.8, 343, 379, 403; 528/421, 528/487; 424/78.17

See application file for complete search history.

(56) References Cited

U.S. PATENT DOCUMENTS

| | | |
|---|---|---|
| 4,179,337 A | 12/1979 | Davis et al. |
| 4,179,551 A | 12/1979 | Jones et al. |
| 4,229,550 A | 10/1980 | Jones et al. |
| 4,251,626 A | 2/1981 | Minamizono et al. |
| 4,288,612 A | 9/1981 | Lewis et al. |
| 4,645,741 A | 2/1987 | Inada |
| 4,675,414 A | 6/1987 | DeFusco et al. |
| 4,839,345 A | 6/1989 | Doi et al. |
| 5,166,322 A | 11/1992 | Shaw et al. |
| 5,527,528 A | 6/1996 | Allen et al. |
| 5,583,114 A | 12/1996 | Barrows et al. |
| 5,585,484 A | 12/1996 | Acharya et al. |
| 5,620,689 A | 4/1997 | Allen et al. |
| 5,641,856 A | 6/1997 | Meurs |
| 5,766,897 A | 6/1998 | Braxton |
| 5,844,020 A | 12/1998 | Paine et al. |
| 5,932,462 A | 8/1999 | Harris et al. |
| 6,001,958 A | 12/1999 | Tapolsky et al. |
| 6,139,819 A | 10/2000 | Unger et al. |
| 6,180,134 B1 | 1/2001 | Zalipsky et al. |
| 6,180,598 B1 | 1/2001 | Nelson |
| 6,183,738 B1 | 2/2001 | Clark |
| 6,210,707 B1 | 4/2001 | Papahadjopoulos et al. |
| 6,261,537 B1 | 7/2001 | Klaveness et al. |
| 6,271,339 B1 | 8/2001 | Thepot et al. |
| 6,303,119 B1 | 10/2001 | Weisgerber et al. |
| 6,306,923 B1 | 10/2001 | Thepot et al. |
| 6,331,289 B1 | 12/2001 | Klaveness et al. |
| 6,521,211 B1 | 2/2003 | Unger et al. |
| 6,552,170 B1 | 4/2003 | Thompson et al. |
| 6,602,498 B2 | 8/2003 | Shen |
| 2001/0044526 A1 | 11/2001 | Shen |
| 2002/0082345 A1 | 6/2002 | Kozlowski et al. |
| 2003/0065134 A1 | 4/2003 | Sakanoue et al. |
| 2003/0086867 A1 | 5/2003 | Lanza et al. |
| 2003/0149307 A1 | 8/2003 | Hai et al. |
| 2003/0162693 A1 | 8/2003 | Winslow et al. |
| 2003/0170474 A1 | 9/2003 | Qiao et al. |
| 2003/0219404 A1* | 11/2003 | Yamasaki et al. .......... 424/85.4 |
| 2004/0167287 A1 | 8/2004 | Kozlowski et al. |
| 2005/0014903 A1 | 1/2005 | Kozlowski et al. |
| 2005/0226843 A1 | 10/2005 | Bentley et al. |

FOREIGN PATENT DOCUMENTS

| | | |
|---|---|---|
| CN | 1110681 A | 10/1995 |
| DE | 19652544 A1 | 6/1998 |
| EP | 0 318 162 | 5/1989 |
| EP | 357110 A1 | 3/1990 |
| EP | 878482 A1 | 11/1998 |
| EP | 1046394 A2 | 10/2000 |
| EP | 0714402 B9 | 11/2000 |
| EP | 1 283 233 | 2/2003 |

(Continued)

OTHER PUBLICATIONS

Juszczak et al. Biochemistry 41 (2002) 376-385.*

(Continued)

Primary Examiner—Roberto Rábago
(74) Attorney, Agent, or Firm—Susan T. Evans; Mark A. Wilson

(57) ABSTRACT

The present invention is directed to hydrolytically stabilized maleimide-functionalized water soluble polymers and to methods for making and utilizing such polymers and their precursors.

61 Claims, 3 Drawing Sheets

FOREIGN PATENT DOCUMENTS

| | | |
|---|---|---|
| FR | 2206317 A1 | 6/1974 |
| JP | 50110491 A2 | 8/1975 |
| JP | 57192418 A2 | 11/1982 |
| JP | 57205413 A2 | 12/1982 |
| JP | 58015515 A2 | 1/1983 |
| JP | 58040374 A2 | 3/1983 |
| JP | 6328645 A2 | 11/1988 |
| JP | 63277619 A2 | 11/1988 |
| JP | 01062338 A2 | 3/1989 |
| JP | 01088129 A2 | 4/1989 |
| JP | 02149335 A2 | 6/1990 |
| JP | 07132685 A2 | 5/1995 |
| JP | 08041195 A2 | 2/1996 |
| JP | 08117586 A2 | 5/1996 |
| JP | 11349877 A2 | 12/1999 |
| JP | 2000/143729 A2 | 5/2000 |
| JP | 2000/144033 A2 | 5/2000 |
| JP | 2000/144041 A2 | 5/2000 |
| JP | 2000191700 | 7/2000 |
| JP | 2000/306605 A2 | 11/2000 |
| JP | 2000/319252 A2 | 11/2000 |
| JP | 2001/172554 A2 | 6/2001 |
| JP | 2001/294777 A2 | 10/2001 |
| JP | 2001/322976 A2 | 11/2001 |
| JP | 2002/121221 A2 | 4/2002 |
| JP | 2002/265442 A2 | 9/2002 |
| JP | 2002/265541 A2 | 9/2002 |
| JP | 2003/040939 A2 | 2/2003 |
| JP | 2003/221443 A2 | 8/2003 |
| JP | 2003/241337 A2 | 8/2003 |
| WO | WO 90/12874 A2 | 11/1990 |
| WO | WO 92/16221 A1 | 10/1992 |
| WO | WO 94/21235 A1 | 9/1994 |
| WO | WO 94/21281 A1 | 9/1994 |
| WO | WO 95/11987 A1 | 5/1995 |
| WO | WO 96/32841 A1 | 10/1996 |
| WO | WO 96/40285 A1 | 12/1996 |
| WO | WO 98/02743 A1 | 1/1998 |
| WO | WO 98/11919 A2 | 3/1998 |
| WO | WO 98/18500 A2 | 5/1998 |
| WO | WO 98/22092 A1 | 5/1998 |
| WO | WO 98/30575 A1 | 7/1998 |
| WO | WO 98/31383 A1 | 7/1998 |
| WO | WO 99/03887 A1 | 1/1999 |
| WO | WO 99/13919 A1 | 3/1999 |
| WO | WO 99/48918 A1 | 9/1999 |
| WO | WO 99/48928 A1 | 9/1999 |
| WO | WO 99/55837 A2 | 11/1999 |
| WO | WO 99/64460 A1 | 12/1999 |
| WO | WO 00/05582 A2 | 2/2000 |
| WO | WO 00/10974 A2 | 3/2000 |
| WO | WO 00/16733 A2 | 3/2000 |
| WO | WO 00/26256 A2 | 5/2000 |
| WO | WO 00/45856 A2 | 8/2000 |
| WO | WO 01/07484 A1 * | 2/2001 |
| WO | WO 01/07484 A2 | 2/2001 |
| WO | WO 01/07577 A2 | 2/2001 |
| WO | WO 01/12154 A2 | 2/2001 |
| WO | WO 01/48052 * | 7/2001 |
| WO | WO 01/48052 A1 | 7/2001 |
| WO | 01/62827 | 8/2001 |
| WO | WO 02/37850 A2 | 2/2002 |
| WO | WO 02/25644 A1 | 3/2002 |
| WO | WO 02/35636 A1 | 5/2002 |
| WO | WO 02/36161 A2 | 5/2002 |
| WO | WO 02/060978 A1 | 8/2002 |
| WO | WO 02/076428 A1 | 10/2002 |
| WO | WO 02/083067 A2 | 10/2002 |
| WO | WO 02/100343 A2 | 12/2002 |
| WO | 03/000278 | 1/2003 |
| WO | WO-03/000278 * | 1/2003 |
| WO | WO 03/000278 A1 | 1/2003 |
| WO | WO 03/028640 A2 | 4/2003 |
| WO | WO 03/034995 A2 | 5/2003 |
| WO | WO 03/047549 A2 | 6/2003 |
| WO | WO 03/057134 A2 | 7/2003 |
| WO | WO 03/059363 A1 | 7/2003 |
| WO | WO 03/061577 A2 | 7/2003 |
| WO | WO 03/064462 A1 | 8/2003 |

OTHER PUBLICATIONS

Acevedo, et al., "Synthesis and Characterization of Imide End-Capped Oligomers of Poly(diethyleneglycol Terephthalate)," *J. of Applied Polymer Sci.* 38(9):1745-1759 (1989).

Acevedo, et al., "Kinetic Study Of The Crosslinking Reaction Of Flexible Bismaleimides," *Polymer* 31(10):1955-1959 (1990).

Acevedo, et al., "Semi-Interpenetrating Polymer Networks Of Maleimide End-Capped Oligoesters," *Polymer* 32(12):2210-2214 (1991).

Alam, et al., "The Importance Of Being Knotted: Effects Of The C-Terminal Knot Structure On Enzymatic And Mechanical Properties Of Bovine Carbonic Anhydrase II," *FEBS Letters* 519(1-3):35-40 (2002).

Allen, et al., "Use Of The Post-Insertion Method For The Formation Of Ligand-Coupled Lipsomes," *Cellular & Molecular Biol. Letters* 7(3):889-894 (2002).

Andreadis, et al., "Use Of Immobilized PCR Primers To Generate Covalently Immobilized Dnas For In Vitro Transcription/Translation Reactions," *Nucleic Acids Research* 28(2):II-VIII (2000).

Bestman-Smith, et al., "Sterically Stabilized Liposomes Bearing Anti-HLA-DR Antibodies For Targeting The Primary Cellular Reservoirs Of HIV-1," *Biochimica et Biophysica Acta* 1468(1-2):161-174 (2000).

Bieniarz, et al., "Extended Length Heterobifunctional Coupling Agents For Protein Conjugations," *Bioconjugate Chem.* 7:88-95 (1996).

Blessing, et al., "Different Strategies For Formation Of PEGylated EGF-Conjugated PEI/DNA Complexes For Targeted Gene Delivery," *Bioconjugate Chem.* 12(4):529-537 (2001).

Chain, et al., "Synthesis Of Bismaleimide Resin Containing The Poly(Ethylene Glycol) Side Chain: Curing Behavior And Thermal Properties," *J. of Applied Polymer Sci.* 85(14):2935-2945 (2002).

Chain, et al., Mechanical Properties And Morphology Of Poly(Ethylene Glycol)-Side-Chain-Modified Bismaleimide Polymer, *J. of Applied Polymer Sci.* 86(3):715-724 (2002).

Chluba, et al., "Enhancement Of Gene Delivery By An Analogue Of α-MSH In A Receptor-Independent Fashion," *Biochimica et Biophysica Acta* 1510(1-2):198-208 (2001).

Christakopouos, et al., "Enhancement Of pH-Stability Of A Low Molecular Mass Endoglucanase From Fusarium Oxysporum By Protein Pegylation," *Carbohydrate Res.* 314(1-2):95-99 (1998).

Dauty, et al., "Intracelular Delivery Of Nanometric DNA Particles Via The Folate Receptor," *Bioconjugate Chem.* 13(4):831-839 (2002).

Derycke, et al., "Transferrin-Mediated Targeting Of Hypericin Embedded In Sterically Stabilized PEG-Liposomes," *International J. of Onocology* 20(1):181-187 (2002).

Dix, et al., "Chain Extension And Crosslinking Of Telechelic Oligomers-1. Michael Additions Of Bismines To Bismaleimides And Bis(Acetylene Ketones)," *Eur. Polym. J.* 31(7):647-652 (1995).

Fleiner, et al., "Studies On Protein-Liposome Coupling Using Novel Thiol-Reactive Coupling Lipids: Influence Of Spacer Length And Polarity," *Bioconjugate Chem.* 12(4):470-475 (2001).

Fles, et al., "Synthesis And Spectroscopic Evidence Of N-Arylmaleimides And N-Aryl-2,3-Dimethylmaleimides," *Croatica Chemica Acta*, 76(1):69-74 (2003).

Gagné, "Targeted Delivery Of Indinavir To HIV-1 Primary Reservoirs With Immunoliposomes," *Biochimica et Biophysica Acta*, 1558(2):198-210, (2002(.

Gaina, et al., "Bismaleimide Resins Containing Urethanic Moieties," *J of Macromolecular Sci.—Pure and Appl. Chem.* A34(12):2435-2449 (1997).

Gheneim, et al., "Diels-Alder Reactions With Novel Polymeric Dienes And Dienophiles: Synthesis Of Reversibly Cross-Linked Elastomers," *Macromolecules* 35(19):7246-7253 (2002).

Gusens, et al., "Targeting Of The Photocytotoxic Compound AlPcS4 To Hela Cells By Transferring Conjugate PEG-Liposomes," *Intern. J. of Cancer* 101(1):78-85 (2002).

Goodson, et al., "Site-Directed Pegylation Of Recombinant Interleukin-2 At Its Glycosylation Site," *Biotech.* 8:343-346 (1990).

Hai, et al., "Synthesis Of Water-Soluble, Nonimmunogenic Polyamide Cross-Linking Agents," *Bioconjugate Chem.* 9(6):645-654 (1998).

Hai, et al., "Polymerization Of Diaspirin Cross-Linked Hemoglobin (DCLHb) With Water-Soluble, Non-immunogenic Polyamide Cross-Liking Agents," *Bioconjugate Chem.* 10(6):1013-1020 (1999).

Heimbuch, et al., "Composites Of Vinyl Polystyrylpyridine/Bismaleimide-Aliphatic Ether Copolymers," *SAMPE Quarterly* 20(3):17-21 (1989).

Hill, et al., "Diels-Alder Bioconjugation Of Diene-Modified Oligonucleotides," *J. Org. Chem..* 66(16):5352-5358 (2001).

Huwyler, et al., "Bypassing Of P-glycoprotein Using Immunoliposomes," *J. of Drug Targeting* 10(1):73-79 (2002).

Ishida, et al., "Targeted Delivery And Triggered Release Of Liposomal Doxorubicin Enhances Cytotoxicity Against Human B Lymphoma Cells," *Biochimica Acta*, 1515(2):144-158, (2001).

Juszczak, et al., "UV Resonance Raman Study Of β93-Modified Hemoglobin A: Chemical Modifier-Specific Effects And Added Influences Of Attached Poly(Ethylene Glycol,)" *Biochemistry* 41(1):376-385 (2002).

Kirpotin et al., "Sterically Stabilized Anti-HER2 Immunoliposomes : Design And Targeting To Human Breast Cancer Cells In Vitro," *Biochemistry* 36(1):66-75 (1997).

Kirchmeier, et al., "Correlations Between The Rate Of Intracellular Release Of Endocytosed Liposomal Doxorubicin And Cytotoxicity As Determined By A New Assay," *J. of Liposome Res.* 11(1):15-29 (2001).

Kley, et al., "Synthesis Of Novel Thiol-Reactive Amphiphilic Lipids Based On Cholesterol For Protein-Liposome Coupling," *Monatshefte für Chemie* 129(3):319-327 (1998).

Kogan, "The Synthesis Of Substituted Methoxy-Poly(Ethyleneglycol) Derivatives Suitable For Selective Protein Modification," *Synthetic Communications* 22(16):2417-2424 (1992).

Kuehne, et al., "SynthesisAand Characterization Of Membrane-Active GALA-OKT9 Conjugates," *Bioconjugate Chemistry* 12(5):742-749 (2001).

Kullberg, et al., "Development Of EGF-Conjugated Liposomes For Targeted Delivery Of Boronated DNA-Binding Agents," *Bioconjugate Chem.* 13(4):737-743 (2002).

Lee, et al., "A New Gene Delivery Formulation Of Polyethylenimine/DNA Complexes Coated With PEG Conjugated Fusogenic Peptide," *Journal of Controlled Release* 76(1-2):183-192 (2001).

Lu, et al., "Preparation And Biological Evaluation Of Polymerizable Antibody Fab' Fragment Targeted Polymeric Drug Delivery System," *Journal of Controlled Released* 74(1-3):263-268 (2001).

Makmura, et al., "Development Of A Sensitive Assay To Detect Reversibly Oxidized Protein Cysteine Sulfydryl Groups," *Antioxidants & Redox Signaling* 3(6):1105-1118 (2001).

Manjula, et al, "Cys-93-ββ-Succinimidophenyl Polyethylene Glycol 2000 Hemoglobin A. Intramolecular Cross-Bridging Of Hemoglobin Outside The Central Cavity," *The J. of Biological Chemistry* 275(8):5527-5534 (2000).

Manjula, et al., "Site-Specific PEGylation Of Hemoglobin At Cys-93(β): Correlation Between The Colligative Properties Of The PEGylated Protein And The Length Of The Conjugated PEG Chain," *Bioconjugate Chem.* 14:464-472 (2003).

Mao, et al., "Chitosan-DNA Nanoparticles As Gene Carriers: Synthesis, Characterization And Transfection Efficiency," *J. of Controlled Release* 70(3):399-421 (2001).

Maruyama, et al., "Targeting Efficiency Of PEG-Immunoliposome-Conjugated Antibodies At PEG Terminals," *Advanced Drug Delivery Reviews* 24(2,3):235-242 (1997).

Maruyama, et al., "Targetability Of PEG-Immunoliposomes Conjugating Antibodies At The Ends Of PEG Chains," *Polymer Preprints* 38(1):541-542 (1997).

Menezes, et al., "Cellular Trafficking And Cytotoxicity Of Anti-CD19-Targeted Liposomal Doxorubicin In B Lymphoma Cells," *Journal of Liposome Research* 9(2):199-228 (1999).

Meyer, et al., "Cationic Liposomes Coated With Polyethylene Glycol As Carriers For Oligonucleotides", *The J. of Biological Chemistry*, 273(25):15621-15627 (1998).

Moreira, et al., "Targeting Stealth Liposomes In A Murine Model Of Human Small Cell Lung Cancer," *Biochemica et Biophysica Acta* 1515(2):167-176 (2001).

Oliver, et al., "Synthesis Of Pegylated Immunonanoparticles," *Pharmaceutical Res.* 19(8):1137-1143 (2002).

Perret, et al., "Versatile Decoration Of Glass Surfaces To Probe Individual Protein Interactions And Cellular Adhesion," *Langmuir* 18(3):846-854 (2002).

Pierce Product Catalog "SMCC (Succinimidyl 4-[N-Maleimidomethyl]Cyclohexane-1-Carboxylate)," Product No. 22360 (2002).

Reddy, et al., "Folate-Targeyted, Cationic Liposome-Mediated Gene Transfer Into Disseminated Peritoneal Tumors," *Gene Therapy* 9(22):1542-1550 (2002).

Romani, et al., "Synthesis Of Unsymmetrical Cystine Peptides: Directed Disulfide Pairing With The Sulfenohydrazide Method," *Chem. of Peptides and Proteins* 2:29-34 (1984).

Sapra, et al., "Targeting Of Immunoliposomal Vincristine To Hematological Malignancies," *Proceed. Int'l. Symp. Control. Rel. Bioact. Mater. Controlled Release Soc.* 28:582-583 (2001).

Sapra, et al., "Internalizing Antibodies Are Necessary For Improved Therapeutic Efficacy Of Antibody-Targeted Liposomal Drugs," *Cancer Res.* 62(24):7190-7194 (2002).

Schmidt, et al., "Force Tolerances Of Hybrid Nanodevices," *Nano Letters* 2(11):1229-1233 (2002).

Shearwater Corporation, pp. 1-17 (2001).

Shi, et al., "Noninvasive Gene Targeting To The Brain," *Proceed. Of the Nat'l Academy of Sci. of the U.S.A.* 97(13):7567-7572 (2000).

Shi, et al., "Brain-Specific Expression Of An Exogenous Gene After I.V. Administration," *Proceed. Of the Nat'l Academy of Sci. of the U.S.A.* 98(22):12754-12759 (2001).

Shukla, et al., "Synthesis And Biological Evaluation Of Folate Receptor-Targeted Boronated PAMAM Dendrimers As Potential Agents For Neutron Capture Therapy," *Bioconjugate Chem.* 14(1):158-167 (2003).

Souza, et al., "Membrane-Active Properties Of α-MSH Analogs: Aggregation And Fusion Of Liposomes Triggered By Surface-Conjugated Peptides," *Biochimica et Biophysica Acta* 1558(2):222-237 (2002).

Takizawa, et al., "Targetability Of The Pendant Type Polyethyleneglycol-Immunoliposomes In Vivo," *Drug Delivery System* 13(6):407-414 (1998).

Tang, et al., "Preparation Of A New Pegylation Reagent For Sulfhydryl-Containing Polypeptide," *Tetrahedron Letters* 35(35):6515-6516 (1994).

Tessmar, et al., "Amine-Reactive Biodegradable Diblock Copolymers", *Biomacromolecules* 3(1):194-200 (2002).

Tsutsumi, et al., "Site-Specific Chemical Modification With Polyethylene Glycol Of Recombinant Immunotoxin Anti-Tac(Fv)-PE38 (LMB-2) Improves Antitumor Activity And Reduces Animal Toxicity And Immunogenicity," *Proceed. of the Nat'l Academy of Sci. of the U.S.A.* 97(15):8548-8553 (2000).

Turner, et al., "The Transfection Of Jurkat T-Leukemic Cells By Use Of pH-Sensitive Immunoliposomes," *Journal of Liposome Research* 12(4):311-334 (2002).

Vargas, et al, "Diels-Alder Modification Of Poly(Ethylene Terphthalate-Co-Anthracene-2,6-Carboxylate) With N-Substituted Maleimides," *J. of Polymer Sci.* 40(19):3256-3263 (2002).

Vreeland, et al., "Molar Mass Profiling Of Synthetic Polymers By Free-Solution Capillary Electrophoresis Of DNA-Polymer Conjugates," *Anal. Chem.* 73(8):1795-1803, (2001).

Wu, et al., "p53 Protein Oxidation In Cultured Cells In Response To Pyrrolidline Dithiocarbamate: A Novel Method For Relation The Amount Of p53 Oxidation In Vivo To The Regulation Of p53-Responsive Genes", *Biochem. J.*, 351(1):87-93, (2000).

Wünsch, et al., "A New Method For The Selective Synthesis of Unsymmetrical Cystine Peptides," *Peptides; Proceedings of the 17th European Peptide Symposium*, pp. 183-188 (1982).

Enzon Pharmaceuticals Catalog, "Macromolecular Engineering Technologies," pp. 1-14 (2004).

Nektar Molecule Engineering Catalog, "Polyethylene Glycol and Derivatives for Advanced PEGylation," pp. 1-21 (2003).

Nektar Advanced PEGylation Catalog, "Polyethylene Glycol and Derivatives for Advanced PEGylation," pp. 1-24 (2004).

Nektar Advanced PEGylation Catalog, "Polyethylene Glycol and Derivatives for Advanced PEGylation," pp. 1-30 (2005-2006).

NOF Corporation Catalog, "Peg Derivatives, Phospholipid and Drug Delivery Materials for Pharmaceuticals," 1: pp. 2-46 (2003).

Polypure Products Catalog, Apr. 2005.

Quanta Biodesign Catalog, "Labeling, Modification and Crosslinking Reagents Incorporating our Unique Monodispersed dPEG™ Technology," pp. 1-38, Mar. 12, 2004.

Quanta Biodesign Catalog, "Labeling, Derivatization and Crosslinking Reagents for Biological and Related Materials with dPEG," pp. 1-31, Nov. 5, 2004.

Quanta Biodesign Product Catalog, "Leading Innovator, Producer and Provider of Monodisperse Discrete PEG (dPEG) Derivatives," pp. 1-51, Nov. 17, 2005.

Shearwater Polymers, Inc., Catalog, , "Functionalized Biocompatible Polymers for Research: Polyethylene Glycol and Derivatives," pp. 2-49 (Mar. 1995).

Shearwater Polymers, Inc., Catalog, , "Functionalized Biocompatible Polymers for Research and Pharmaceuticals: Polyethylene Glycol and Derivatives," pp. 2-53 (1997-1998).

Shearwater Polymers, Inc., Catalog, "Functionalized Biocompatible Polymers for Research and Pharmaceuticals: Polyethylene Glycol and Derivatives," pp. 2-50 (2000).

* cited by examiner

HYDROLYTICALLY STABLE MALEIMIDE-TERMINATED POLYMERS

CROSS REFERENCE TO RELATED APPLICATIONS

This application claims the benefit of priority to U.S. provisional application Ser. No. 60/437,211, filed Dec. 31, 2002, which is incorporated herein by reference in its entirety.

FIELD OF THE INVENTION

This invention relates to particular maleimide-terminated water soluble polymers, and to methods for making and utilizing such polymers. In particular, the invention relates to: (i) hydrolytically stabilized polymers having one or more terminal maleimide groups, (ii) conjugates formed from the attachment of a maleimide-terminated water soluble polymer reagent as described herein to another substance, such as an active agent or surface, (iii) methods for synthesizing such polymeric reagents, (iv) compositions comprising the polymeric reagents, and the like.

BACKGROUND OF THE INVENTION

Due to recent advances in biotechnology, therapeutic proteins and other biomolecules, e.g. antibodies and antibody fragments, can now be prepared on a large scale, making such biomolecules more widely available. Unfortunately, the clinical usefulness of potential therapeutic biomolecules is often hampered by their rapid proteolytic degradation, low bioavailability, instability upon manufacture, storage or administration, or by their immunogenicity. Due to the continued interest in administering proteins and other biomolecules for therapeutic use, various approaches to overcoming these deficiencies have been explored.

One such approach which has been widely explored is the modification of proteins and other potentially therapeutic molecules by covalent attachment of a water soluble polymer such as polyethylene glycol or "PEG" (Abuchowski, A., et al, J. Biol. Chem. 252 (11), 3579 (1977); Davis, S., et al., Clin. Exp Immunol., 46, 649-652 (1981). The biological properties of PEG-modified proteins, also referred to as PEG-conjugates or pegylated proteins, have been shown, in many cases, to be considerably improved over those of their non-pegylated counterparts (Herman, et al., Macromol. Chem. Phys., 195, 203-209 (1994). Polyethylene glycol-modified proteins have been shown to possess longer circulatory times in the body due to increased resistance to proteolytic degradation, and also to possess increased thermostability (Abuchowski, A., et al., J. Biol. Chem., 252, 3582-3586 (1977). A similar increase in bioefficacy is observed with other biomolecules, e.g. antibodies and antibody fragments (Chapman, A., Adv. Drug Del. Rev. 54, 531-545 (2002)).

Typically, attachment of polyethylene glycol to a drug or other surface is accomplished using an activated PEG derivative, that is to say, a PEG having at least one activated terminus suitable for reaction with a nucleophilic center of a biomolecule (e.g., lysine, cysteine and similar residues of proteins). Most commonly employed are methods based upon the reaction of an activated PEG with protein amino groups, such as those present in the lysine side chains of proteins. Polyethylene glycol having activated end groups suitable for reaction with the amino groups of proteins include PEG-aldehydes (Harris, J. M., Herati, R. S., Polym Prepr. (Am. Chem. Soc., Div. Polym. Chem), 32(1), 154-155 (1991), mixed anhydrides, N-hydroxysuccinimide esters, carbonylimadazolides, and chlorocyanurates (Herman, S., et al., Macromol. Chem. Phys. 195, 203-209 (1994)). Although many proteins have been shown to retain activity during PEG modification, in some instances, polymer attachment through protein amino groups can be undesirable, such as when derivatization of specific lysine residues inactivates the protein (Suzuki, T., et al., Biochimica et Biophysica Acta 788, 248-255 (1984)). Moreover, since most proteins possess several available/accessible amino groups, the polymer conjugates formed are typically mixtures of mono-pegylated, di-pegylated, tri-pegylated species and so on, which can be difficult and also time-consuming to characterize and separate. Further, such mixtures are often not reproducibly prepared, which can create problems during scale-up for regulatory approval and subsequent commercialization.

One method for avoiding these problems is to employ a site-selective polymer reagent that targets functional groups other than amines. One particularly attractive target is the thiol group on proteins, present in the amino acid, cysteine. Cysteines are typically less abundant in proteins than lysines, thus reducing the likelihood of protein deactivation upon conjugation to these thiol-containing amino acids. Moreover, conjugation to cysteine sites can often be carried out in a well-defined manner, leading to the formation of single species polymer-conjugates.

Polyethylene glycol derivatives having a thiol-selective reactive end group include maleimides, vinyl sulfones, iodoacetamides, thiols, and disulfides, with maleimides being the most popular. These derivatives have all been used for coupling to the cysteine side chains of proteins (Zalipsky, S. Bioconjug. Chem. 6, 150-165 (1995); Greenwald, R. B. et al. Crit. Rev. Ther. Drug Carrier Syst. 17, 101-161 (2000); Herman, S., et al., Macromol. Chem. Phys. 195, 203-209 (1994)). However, many of these reagents have not been widely exploited due to the difficulty in their synthesis and purification.

As discussed above, polyethylene glycol derivatives having a terminal maleimide group are one of the most popular types of sulfhydryl-selective reagents, and are commercially available from a number of sources. Although not widely appreciated or recognized, the Applicants have recognized that many PEG-maleimides unfortunately are hydrolytically unstable during storage and conjugation to a drug candidate. More particularly, a substantial degree of hydrolysis of the maleimide ring has been observed, both prior to and after conjugation. This instability can result in the formation of multiple species of drug conjugates within a drug-conjugate composition. The various drug conjugate species are likely to possess similar biological activities, but may differ in their pharmacokinetic properties, making such compositions undesirable for patient administration. Additionally, separation of the open-ring and closed-ring forms of the drug conjugate can be extremely difficult to carry out. Moreover, such hydrolytic instability can lead to inconsistency in drug batches. Thus, the applicants have realized a continuing need in the art for the development of new activated PEGs useful for coupling to biologically active molecules, desirably in a site-selective fashion, that are stable during both storage and coupling. This invention meets those needs.

SUMMARY OF THE INVENTION

The present invention provides a unique family of hydrolytically stabilized maleimide-terminated polymers, where the polymers comprise particular linkers interposed between a polymer segment and a maleimide group.

The invention is based on the discovery that the incorporation of a saturated acyclic, cyclic, or alicyclic hydrocarbon linker adjacent to the maleimide ring of a maleimide-terminated polymer substantially reduces its instability. Provided herein are polymers having a hydrolytically stabilized maleimide ring, their polymer precursors, conjugates of the hydrolytically stabilized maleimide-terminated polymers, and methods for making and using such polymers and their conjugates.

Generally, the present invention is directed to a water soluble polymer having the structure:

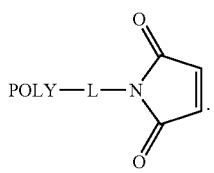

I

In the generalized structure above, POLY is a water soluble polymer segment, and L is a linkage that imparts hydrolytical stability to the adjacent maleimide ring. Typically the linker comprises a saturated acyclic, cyclic or alicyclic hydrocarbon chain adjacent to the maleimide ring and contains a total of about 3 to about 20 carbon atoms, optionally containing other non-interfering atoms or functional groups.

More particularly, in one aspect, the invention is directed to a water-soluble polymer having the structure:

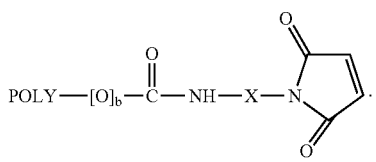

II

In structure II, POLY is a water-soluble polymer segment, b is 0 or 1, and X is a hydrolytically stable linker comprising at least 3 contiguous saturated carbon atoms. Preferably, the polymer is absent aromatic groups and ester linkages. In one embodiment, POLY is directly covalently bonded to the amide carbonyl carbon, optionally via an intervening oxygen ($[O]_b$) to form a carbamate group. In an alternative embodiment, POLY is connected to the amide carbonyl carbon, optionally via an intervening oxygen, ([O]) in the instance when b=1, via an intervening spacer, for example, a methylene.

In one embodiment, X is a saturated acyclic, cyclic or alicyclic hydrocarbon chain having a total of about 3 to about 20 carbon atoms. More particularly, X can possess a total number of carbon atoms selected from the group consisting of 3, 4, 5, 6, 7, 8, 9, 10, 11, 12, 13, 14, 15, 16, 17, 18, 19, and 20. Preferred ranges for total number of carbon atoms in the linker X are from about 3 to about 20, or from about 4 to about 12, or from about 4 to about 10, or from about 5 to about 8 atoms.

The linker X in formula II may possess any of a number of structural features. In one embodiment, X is a linear saturated acyclic hydrocarbon chain. In yet another embodiment, X is a branched saturated acyclic hydrocarbon chain and can contain one or even two substituents, at any one or more of the carbon positions in the chain. For example, X can be branched at the carbon α to the maleimidyl group, or at the carbon β to the maleimidyl group, or at the carbon γ to the maleimidyl group. For hydrocarbon chains having up to 19 carbon atoms, any one of positions 1 to 19 (with position 1 being the one proximal to the maleimide ring) may be branched. For instance, for an exemplary saturated hydrocarbon chain having from 2 to 19 carbon atoms designated $C_1$-$C_2$-$C_3$-$C_4$-$C_5$-$C_6$-$C_7$-$C_8$-$C_9$-$C_{10}$-$C_{11}$-$C_{12}$-$C_{13}$-$C_{14}$-$C_{15}$-$C_{16}$-$C_{17}$-$C_{18}$-$C_{19}$-, any one or more of carbons $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, or $C_{19}$, depending on the total number of carbons in the chain, may be branched. Preferably, in any given saturated hydrocarbon chain or alicyclic linker, 4 or fewer carbon atoms are branched, with the overall number of branching positions preferably equal to 1, 2, 3, or 4. Embodiments wherein the "branch" points taken together form a saturated ring or ring system (e.g., bicyclic, tricyclic, etc.) are discussed separately below.

Representative polymers in accordance with different embodiments of the invention are provided below.

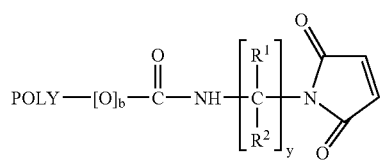

III

For example, in structure III, y is an integer from 1 to about 20; and $R^1$ and $R^2$ in each occurrence are each independently H or an organic radical that is selected from the group consisting of alkyl, substituted alkyl, cycloalkyl, substituted cycloalkyl, alkylenecycloalkyl, and substituted alkylenecycloalkyl.

Preferably, in structure III above, $R^1$ and $R^2$ in each occurrence are each independently H or an organic radical selected from the group consisting of lower alkyl and lower cycloalkyl. Y is preferably selected from the group consisting of 3, 4, 5, 6, 7, 8, 9, and 10. In a particular embodiment of structure III, $R^1$ and $R^2$ are both H.

Various embodiments of structure III include the following.

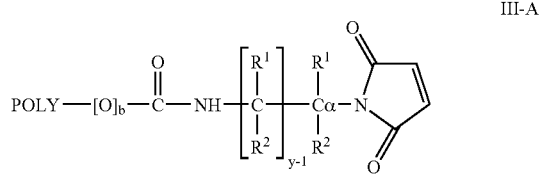

III-A

In illustrative structure III-A, at least one of $R^1$ or $R^2$ on $C_\alpha$ is selected from the group consisting of alkyl, substituted alkyl, cycloalkyl, substituted cycloalkyl, alkylenecycloalkyl, and substituted alkylenecycloalkyl, and y is at least one and may possess any of the above-described specific values.

Particular embodiments of structure III-A include those where:

(i) each of $R^1$ and $R^2$ on $C_\alpha$ is independently selected from the group consisting of alkyl, substituted alkyl, cycloalkyl, substituted cycloalkyl, alkylenecycloalkyl, and substituted alkylenecycloalkyl, and/or (ii) all other non-$C_\alpha$ $R^1$ and $R^2$ variables are H, and/or (iii) at least one of $R^1$ or $R^2$ on $C_\alpha$ is lower alkyl or lower cycloalkyl, and/or (iv) $R^2$ on $C_\alpha$ is H, and/or (v) $R^1$ on $C_\alpha$ is selected from the group consisting of methyl, ethyl, propyl, isopropyl, butyl, isobutyl, pentyl, cyclopentyl, hexyl, and methylenecyclohexyl.

Yet another particular embodiment of this aspect of the invention is provided as structure III-B below.

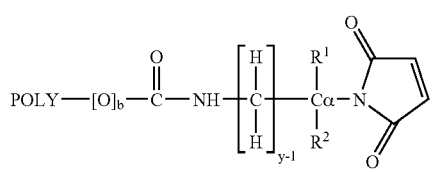

III-B wherein $R^1$ and $R^2$ are each independently alkyl or cycloalkyl. Alternatively, $R^1$ is alkyl or cycloalkyl and $R^2$ is H. Additional embodiments of structure III-B are those where (i) $R^1$ and $R^2$ are each independently either methyl or ethyl, and/or $R^1$ and $R^2$ are the same.

In yet another embodiment of structure III, a polymer of the invention possesses the following structure:

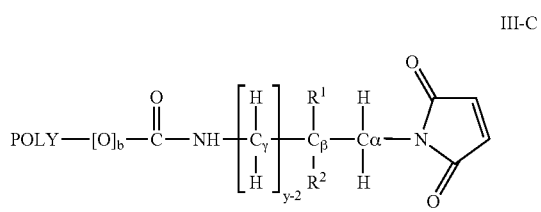

III-C where $R^1$ and $R^2$ are each independently selected from the group consisting of H, alkyl, substituted alkyl, cycloalkyl, substituted cycloalkyl, alkylenecycloalkyl, and substituted alkylenecycloalkyl, but are not both H, and y is at least 2.

Particular embodiments of this structure include those where (i) $R^1$ and $R^2$ are each independently H, lower alkyl or lower cycloalkyl, and/or (ii) $R^1$ and $R^2$ are each independently selected from the group consisting of H, methyl, ethyl, propyl, isopropyl, butyl, isobutyl, pentyl, cyclopentyl, hexyl, and cyclohexyl, and/or $R^2$ is H.

In yet another embodiment of structure III,

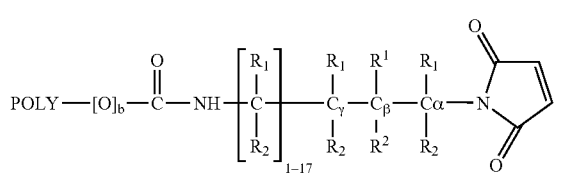

III-D at least one of $R^1$ and $R^2$ attached to $C_\gamma$ is selected from the group consisting of alkyl, substituted alkyl, cycloalkyl, substituted cycloalkyl, alkylenecycloalkyl, and substituted alkylenecycloalkyl. Specific embodiments include those where: (i) at least one of $R^1$ and $R^2$ attached to $C_\gamma$ is alkyl or cycloalkyl and all other $R^1$ and $R^2$ variables are H, and/or (ii) one of the $R^1$ variables attached to $C_\alpha$ or $C_\beta$ is alkyl or cycloalkyl, and all other $R^1$ and $R^2$ variables are H.

As described previously, X can be a saturated cyclic or alicyclic hydrocarbon chain, that is to say, the linker X may contain one or more cyclic hydrocarbons. Generally, also provided herein are polymers having the structure:

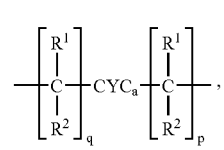

IV

In the preceding structure, $CYC_a$ is a cycloalkylene group having "a" ring carbons, where the value of "a" ranges from 3 to 12; and p and q are each independently 0 to 20, and p+q+a≦20. $R^1$ and $R^2$, in each occurrence, are each independently H or an organic radical that is selected from the group consisting of alkyl, substituted alkyl, cycloalkyl, substituted cycloalkyl, alkylenecycloalkyl, and substituted alkylenecycloalkyl.

$CYC_a$ in accordance with the invention encompasses unicyclic, bicyclic, tricyclic structures and the like.

Various embodiments of structure IV above include those where:

(i) p and q are each independently selected from the group consisting of 0, 1, 2, 3, 4, 5, 6, 7, and 8, and/or (ii) $R^1$, in each occurrence, is independently H or an organic radical that is either lower alkyl or lower cycloalkyl, and $R^2$, in each occurrence, is independently H or an organic radical that is either lower alkyl or lower cycloalkyl, and/or (iii) a is selected from the group consisting of 5, 6, 7, 8 and 9, and/or (iv) a is 6 and $CYC_a$ is a 1,1-, 1,2-, 1,3- or 1,4-substituted cyclohexyl ring, and/or (v) p and q each independently range from 0 to 4, and/or (vi) $R^1$ and $R^2$ are H in every occurrence.

For linkers comprising a cyclcoalkylene group and two substituents thereon, the substituents can be either cis or trans.

Specific embodiments of structure IV include:

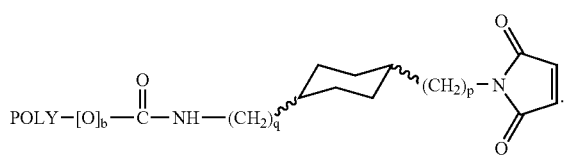

IV-A wherein q and p are as described above. In a particular embodiment, q and p each independently range from 0 to 6. In yet another embodiment, q ranges from 0 to 6 and p is zero.

Yet another exemplary polymer structure having a cycloalkylene ring in accordance with the invention is:

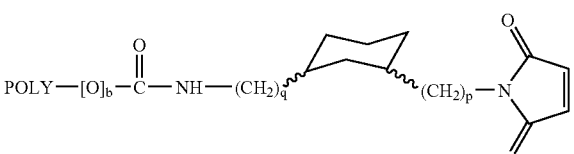

IV-B wherein q and p are as defined above, and more preferably, each independently range from 0 to 6.

Polymers of the invention include monofunctional, bifunctional, and multi-functional structures.

For instance, a polymer of the invention may be described generally by the following structure:

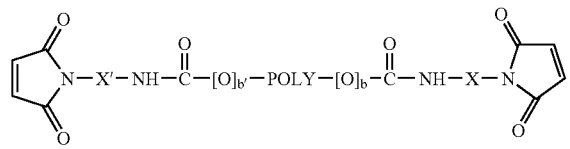

V where X and b are as previously defined, b' is 0 or 1, and X' is a hydrolytically stable linker comprising at least 3 contiguous saturated carbon atoms. In the above embodiment, b and b' may be the same of different, and X and X' may be the same or different. In one particular embodiment the polymer reagent is homo-bifunctional, that is to say, both reactive end groups are the same. In this instance, b equals b' and X equals X'.

Preferably, the water-soluble polymer segment in any of the polymer maleimides provided herein is a poly(alkylene oxide), a poly(vinyl pyrrolidone), a poly(vinyl alcohol), a polyoxazoline, a poly(acryloylmorpholine), or a poly(oxyethylated polyol). In a preferred embodiment, the polymer segment is a poly(alkylene oxide), preferably poly(ethylene glycol).

According to one embodiment, the poly(ethylene glycol) segment comprises the structure: $Z\text{-}(CH_2CH_2O)_n\text{--}CH_2CH_2\text{--}$, where n ranges from about 10 to about 4000 and Z is a moiety comprising a functional group selected from the group consisting of hydroxy, amino, ester, carbonate, aldehyde, alkenyl, acrylate, methacrylate, acrylamide, sulfone, thiol, carboxylic acid, isocyanate, isothiocyanate, hydrazide, maleimide, vinylsulfone, dithiopyridine, vinylpyridine, iodoacetamide, alkoxy, benzyloxy, silane, lipid, phospholipid, biotin, and fluorescein. In this embodiment, Z comprises a reactive functional group or an end-capping group.

In yet a more specific embodiment, POLY may be terminally capped with an end-capping moiety such as alkoxy, substituted alkoxy, alkenyloxy, substituted alkenyloxy, alkynyloxy, substituted alkynyloxy, aryloxy, substituted aryloxy, or phospholipid. Preferred end-capping groups include methoxy, ethoxy, and benzyloxy.

Generally, POLY possesses a nominal average molecular mass falling within one of the following ranges: from about 100 daltons to about 100,000 daltons, from about 1,000 daltons to about 50,000 daltons, or from about 2,000 daltons to about 30,000 daltons. Preferred molecular masses for POLY include 250 daltons, 500 daltons, 750 daltons, 1 kDa, 2 kDa, 5 kDa, 10 kDa, 15 kDa, 20 kDa, 30 kDa, 40 kDa, and 50 kDa, or even greater.

The polymer segment may possess any of a number of geometries, e.g., may be linear, branched or forked.

The polymer of the invention may be multi-armed. An exemplary multi-arm polymer in accordance with the invention has the structure:

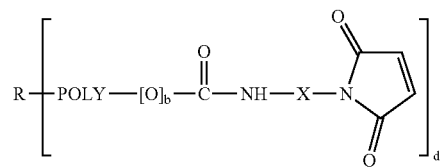

VI

In the above illustrative structure, d is an integer from 3 to about 100, and R is a residue of a central core molecule having 3 or more hydroxyl groups, amino groups, or combinations thereof. Preferably, d is an integer from 3 to about 12.

In an alternative multi-arm embodiment, the polymer corresponds to the structure:

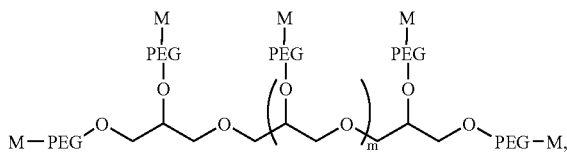

VII

In this structure,
PEG is $-(CH_2CH_2O)_n CH_2CH_2-$,
M is:

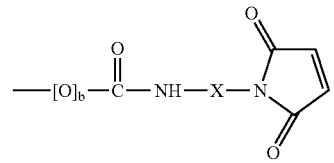

and m is selected from the group consisting of 3, 4, 5, 6, 7, and 8.

In yet another aspect, provided herein are polymers having the above described features and exemplary structures, with the exception that the maleimide group in the above-described polymers is replaced with an amino group, preferably a primary amino, $-NH_2$. Such polymers are useful not only as activated polymer reagents, e.g., for conjugation to an active agent, but are also precursors to the stabilized maleimide polymers of the invention.

For example, the invention encompasses a water-soluble polymer in accordance with the structure:

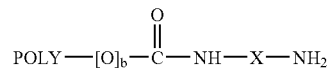

VIII where the variables X and b are as previously described, both generally and in specific embodiments. Preferably, the polymer is absent aromatic groups and ester linkages.

In yet another aspect, the invention provides a water soluble polymer having the structure:

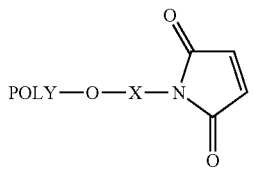

XIII where POLY is a water-soluble polymer segment, and X is a hydrolytically stable linker that is a saturated cyclic or alicyclic hydrocarbon chain having a total of about 3 to about 20 carbon atoms. Preferably, the polymer is absent aromatic groups and ester linkages.

Polymers in accordance with this aspect of the invention encompass, in various embodiments, those where X corresponds to the general and specific cyclic and alicyclic hydrocarbon structures described herein.

In one particular embodiment of structure XIII, the linker X has the structure:

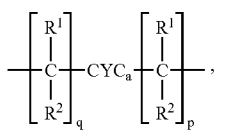

XIII-A where

CYC$_a$ is a cycloalkylene group having "a" ring carbons, where the value of "a" ranges from 3 to 12; p and q are each independently 0 to 20, and p+q+a≦20. In structure XIII-A, each of R$^1$ and R$^2$, in each occurrence, is independently H or an organic radical that is selected from the group consisting of alkyl, substituted alkyl, cycloalkyl, substituted cycloalkyl, alkylenecycloalkyl, and substituted alkylenecycloalkyl. In instances where CYC$_a$ possesses only two substituents, such substituents can be cis or trans.

In yet another embodiment of structure XIII-A, p and q are each independently selected from the group consisting of 0, 1, 2, 3, 4, 5, 6, 7, and 8.

In yet another embodiment of structure XIII-A, R$^1$, in each occurrence, is independently H or an organic radical that is selected from the group consisting of lower alkyl, lower cycloalkyl, and lower alkylenecycloalkyl, and R$^2$, in each occurrence, is independently H or an organic radical that is selected from the group consisting of lower alkyl, lower cycloalkyl, and lower alkylenecycloalkyl.

In yet another embodiment of structure XIII-A, a is selected from the group consisting of 5, 6, 7, 8 and 9.

In a preferred embodiment of structure XIII-A, a is 6 and CYC$_a$ is a 1,1-, 1,2-, 1,3- or 1,4-substituted cyclohexyl ring. Additional embodiments include those where p and q each independently range from 0 to 4, and/or where R$^1$ and R$^2$ are H in every occurrence.

Particularly, certain embodiments of structure XIII include:

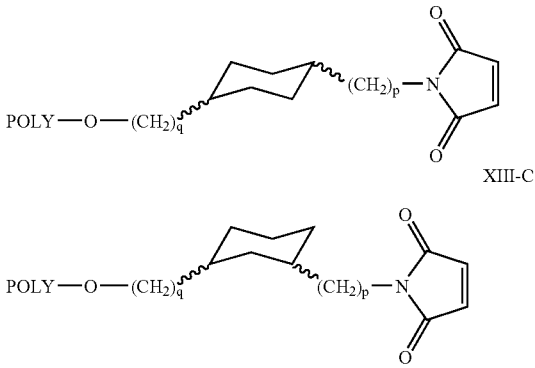

XIII-B

XIII-C wherein q and p each independently range from 0 to 6.

In yet another embodiment of structure XIII, CYC$_a$ is bicyclic or tricyclic.

In yet another aspect, the invention includes hydrogels prepared using any one or more of the polymers described herein.

In yet another aspect, provided is a method for forming a hydrolytically stable maleimide-terminated polymer. The method includes the steps of (a) reacting a polymer having the structure, POLY-[O]$_b$—C(O)-LG (IX), with a diamine having the structure, NH$_2$—X—NH$_2$ (XII), under conditions effective to form POLY-[O]$_b$—C(O)—HN—X—NH$_2$ (X), followed by (b) converting POLY-[O]$_b$—C(O)—HN—X—NH$_2$ (X) into POLY-[O]$_b$—C(O)—HN—X-MAL (II).

The variables POLY, b and X are as described previously, both generally and specifically, LG represents a leaving group, and MAL is maleimide. Preferably, the resulting product, POLY-[O]$_b$—C(O)—HN—X-MAL, is absent aromatic groups and ester linkages.

The method can be used to prepare any of the polymer-terminated maleimides described herein.

Preferred leaving groups include halide, N-hydroxysuccinimide, N-hydroxybenzotriazole, para-nitrophenolate.

In one embodiment of the method, one of the amino groups in said NH$_2$—X—NH$_2$ reagent is in protected form. In this instance, the method will generally comprise, after the reacting step, deprotecting the amino group in POLY-[O]$_b$—C(O)—H$_2$N—X—NH$_2$.

The reacting step is typically carried out in an organic solvent. Typical solvents include acetonitrile, chlorinated hydrocarbons, aromatic hydrocarbons, tetrahydrofuran (THF), dimethylformamide (DMF), and dimethylsulfoxide.

In another embodiment of the method, the reacting step is conducted under an inert atmosphere such as nitrogen or argon.

Temperatures for carrying out the reacting step range from about 0 to 100° C.

In a further embodiment, the reacting step is carried out in the presence of a base. Examplary bases include triethyl amine and other similar tertiary amines, pyridine, 4-(dimethylamino)pyridine, and inorganic bases such as sodium carbonate.

In a preferred embodiment, the method further includes the step of purifying the product from step (a) prior to the converting step, for example, by column chromatography, preferably by ion exchange chromatography.

In yet another specific embodiment, the converting step comprises reacting POLY-[O]$_b$—C(O)—H$_2$N—X—NH$_2$ with a reagent selected from the group consisting of N-methoxycarbonylmaleimide, exo-7-oxa[2.2.1]bicycloheptane-2,3-dicarboxylic anhydride, and maleic anhydride, under conditions suitable for forming POLY-[O]$_b$—C(O)—H$_2$N—X-MAL in a reaction mixture.

In an embodiment where the reagent is N-methoxycarbonylmaleimide, the converting step is preferably carried out in water or an aqueous mixture of water and a water miscible solvent such as acetone or acetonitrile.

In an embodiment of the above method where the reagent is maleic anhydride, the converting step comprises reacting POLY-[O]$_b$—C(O)—H$_2$N—X—NH$_2$ with maleic anhydride under conditions effective to form POLY-[O]$_b$—C(O)—NH—X—NH—C(O)CH=CHCOOH (XI) as an intermediate, followed by heating POLY-[O]$_b$—C(O)—H$_2$N—X—NH—C(O)CH=CHCOOH under conditions effective to promote cyclization by elimination of water to form POLY-[O]$_b$—C(O)—NH—X-MAL.

Generally, the method further comprises the step of recovering the product, POLY-[O]$_b$—C(O)—H$_2$N—X-MAL, from the reaction mixture.

Preferably, the recovered product has a purity of greater than about 80%, and is absent polymeric impurities other than the desired product.

Exemplary diamines for carrying out the method include

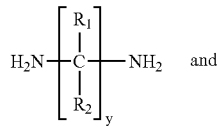

XII-A and

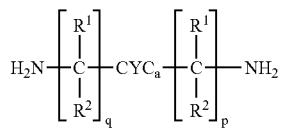

XII-B where the variables encompass those both generally and specifically described above.

In yet another aspect, provided herein is an alternative method for preparing a hydrolytically stable maleimide-terminated polymer of the invention. The method includes the steps of reacting POLY-[O]$_b$—C(O)-LG (IX) with H$_2$N—X-MAL (XIV) under conditions effective to form POLY-[O]$_b$—C(O)—HN—X-MAL (II), where the variables POLY, b, X, LG, and MAL are as previously defined, both generally and specifically, regardless of the subject embodiment used for exemplification purposes.

In yet another aspect, the invention provides a conjugate formed by reaction of a biologically active agent with any of the herein described hydrolytically stable maleimide- or amino-terminated polymers.

More particularly, one embodiment of this aspect of the invention includes a conjugate comprising the following structure:

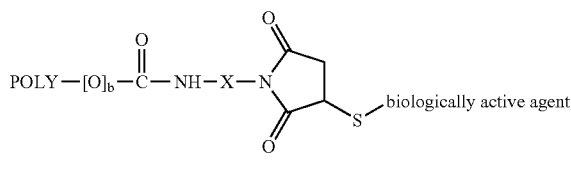

XV where the variables POLY, b and X are as previously defined, both generally and specifically, regardless of the subject exemplifying embodiment, "POLY-[O]$_b$—C(O)—NH—X—" is absent aromatic groups and ester linkages, and "—S-biologically active agent" represents a biologically active agent comprising a thiol (—SH) group.

In one embodiment, provided is a composition comprising the above conjugate. In a more particular embodiment, the conjugate composition comprises a single polymer conjugate species.

In yet another embodiment, the invention is directed to a conjugate comprising the following structure:

XVI

POLY—[O]$_b$—C(O)—NH—X—N(succinimide with biologically active agent via NH)

wherein POLY, b, and X are as defined above, both generally and specifically, "POLY-[O]$_b$—C(O)—NH—X—" is absent aromatic groups and ester linkages, and "—NH—biologically active agent" represents a biologically active agent comprising an amino group.

In yet another related aspect, the invention provides a method for forming a polymer conjugate, where the method includes the step of contacting a biologically active agent comprising a reactive thiol group, "HS-biologically active agent", with a hydrolytically ring stable maleimide terminated polymer of the invention, under conditions effective to promote formation of a polymer conjugate having the structure:

POLY—[O]$_b$—C(O)—NH—X—N(succinimide with S-biologically active agent)

These and other objects and features of the invention will become more fully apparent when read in conjunction with the following figures and detailed description.

DETAILED DESCRIPTION OF THE INVENTION

Figure 1A:
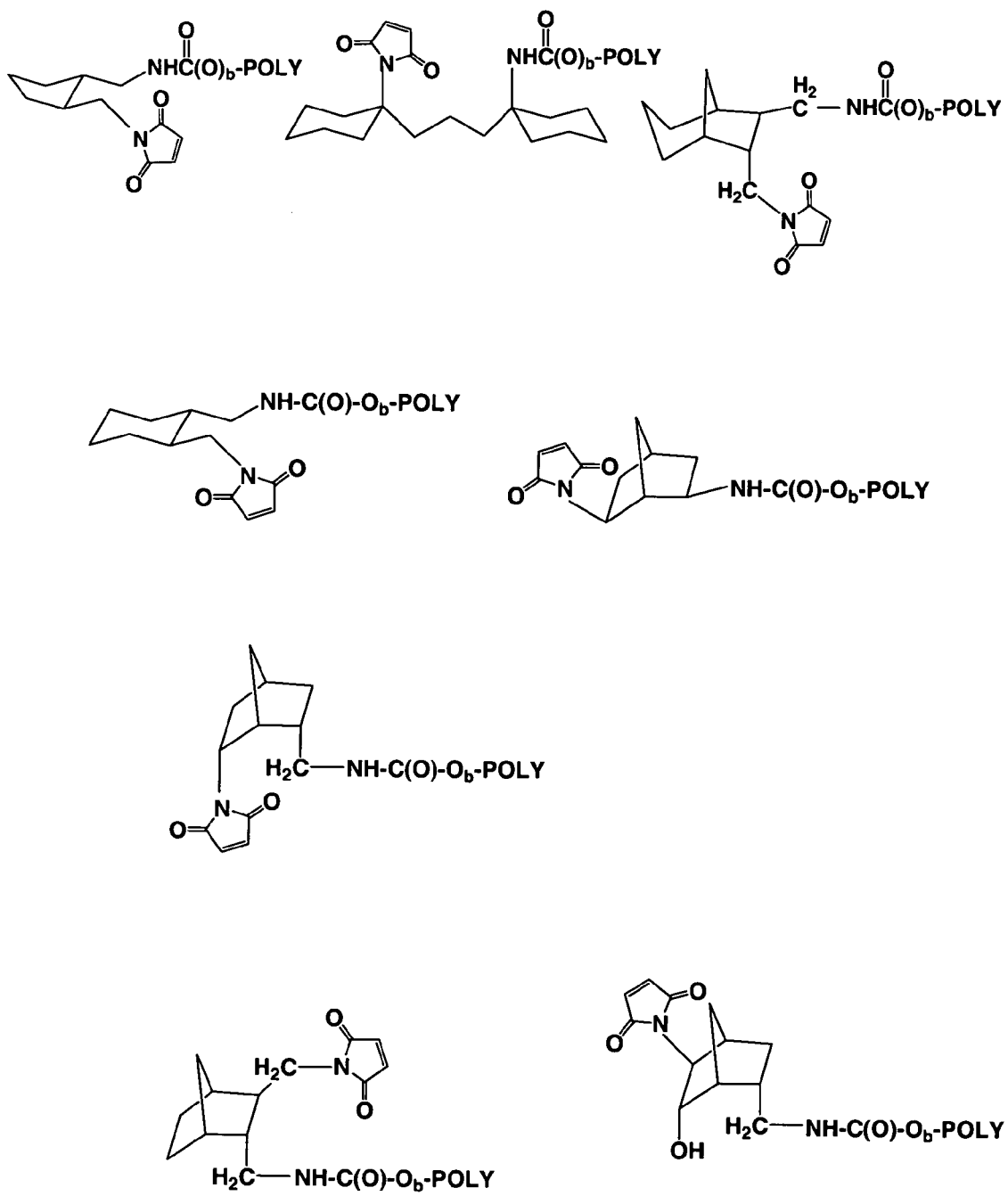
FIGS. 1A and 1B provide structures of exemplary polymer maleimides of the invention containing hydrolytically stable cyclic (including bicyclic and tricyclic) linkers, and FIG. 2 provides structures of exemplary diamines useful in preparing certain stabilized polymer maleimides of the invention.

Before describing the present invention in detail, it is to be understood that this invention is not limited to the particular polymers, synthetic techniques, active agents, and the like as such may vary. It is also to be understood that the terminology used herein is for describing particular embodiments only, and is not intended to be limiting.

In describing and claiming the present invention, the following terminology will be used in accordance with the definitions described below.

Definitions

The following terms as used herein have the meanings indicated.

As used in the specification, and in the appended claims, the singular forms "a", "an", "the", include plural referents unless the context clearly dictates otherwise.

"PEG" or "poly(ethylene glycol)" as used herein, is meant to encompass any water-soluble poly(ethylene oxide). Typically, PEGs for use in the present invention will comprise one of the two following structures: "—(CH$_2$CH$_2$O)$_n$—" or "—(CH$_2$CH$_2$O)$_{n-1}$CH$_2$CH$_2$—," depending upon whether or not the terminal oxygen(s) has been displaced, e.g., during a synthetic transformation. The variable (n) ranges from 3 to 3000, and the terminal groups and architecture of the overall PEG may vary. When PEG further comprises a linker moiety (to be described in greater detail below), the atoms comprising the linker, when covalently attached to a PEG segment, do not result in formation of (i) an oxygen-oxygen bond (—O—O—, a peroxide linkage), or (ii) a nitrogen-oxygen bond (N—O, O—N). "PEG" means a polymer that contains a majority, that is to say, greater than 50%, of subunits that are —CH$_2$CH$_2$O—. PEGs for use in the invention include PEGs having a variety of molecular weights, structures or geometries (e.g., branched, linear, forked PEGs, dendritic, and the like), to be described in greater detail below.

"PEG diol", also known as alpha-, omega-dihydroxylpoly (ethylene glycol), can be represented in brief form as HO-PEG-OH, where PEG is as defined above.

"Water-soluble", in the context of a polymer of the invention or a "water-soluble polymer segment" is any segment or polymer that is soluble in water at room temperature. Typically, a water-soluble polymer or segment will transmit at least about 75%, more preferably at least about 95% of light, transmitted by the same solution after filtering. On a weight basis, a water-soluble polymer or segment thereof will preferably be at least about 35% (by weight) soluble in water, more preferably at least about 50% (by weight) soluble in water, still more preferably about 70% (by weight) soluble in water, and still more preferably about 85% (by weight) soluble in water. It is most preferred, however, that the water-soluble polymer or segment is about 95% (by weight) soluble in water or completely soluble in water.

An "end-capping" or "end-capped" group is an inert or non-reactive group present on a terminus of a polymer such as PEG. An end-capping group is one that does not readily undergo chemical transformation under typical synthetic reaction conditions. An end capping group is generally an alkoxy group, —OR, where R is an organic radical comprised of 1-20 carbons and is preferably lower alkyl (e.g., methyl, ethyl) or benzyl. "R" may be saturated or unsaturated, and includes aryl, heteroaryl, cyclo, heterocyclo, and substituted forms of any of the foregoing. For instance, an end capped PEG will typically comprise the structure "RO—(CH$_2$CH$_2$O)$_n$—", where R is as defined above. Alternatively, the end-capping group can also advantageously comprise a detectable label. When the polymer has an end-capping group comprising a detectable label, the amount or location of the polymer and/or the moiety (e.g., active agent) to which the polymer is coupled, can be determined by using a suitable detector. Such labels include, without limitation, fluorescers, chemiluminescers, moieties used in enzyme labeling, colorimetric (e.g., dyes), metal ions, radioactive moieties, and the like. The end-capping group can also advantageously comprise a phospholipid. When the polymer has an end-capping group such as a phospholipid, unique properties (such as the ability to form organized structures with similarly end-capped polymers) are imparted to the polymer. Exemplary phospholipids include, without limitation, those selected from the class of phospholipids called phosphatidylcholines. Specific phospholipids include, without limitation, those selected from the group consisting of dilauroylphosphatidylcholine, dioleylphosphatidylcholine, dipalmitoylphosphatidylcholine, disteroylphosphatidylcholine, behenoylphosphatidylcholine, arachidoylphosphatidylcholine, and lecithin.

"Non-naturally occurring" with respect to a polymer of the invention means a polymer that in its entirety is not found in nature. A non-naturally occurring polymer of the invention may however contain one or more subunits or segments of subunits that are naturally occurring, so long as the overall polymer structure is not found in nature.

"Molecular mass" in the context of a water-soluble polymer of the invention such as PEG, refers to the nominal average molecular mass of a polymer, typically determined by size exclusion chromatography, light scattering techniques, or intrinsic velocity determination in 1,2,4-trichlorobenzene. The polymers of the invention are typically polydisperse, possessing low polydispersity values of less than about 1.20.

The term "reactive" or "activated" refers to a functional group that reacts readily or at a practical rate under conventional conditions of organic synthesis. This is in contrast to those groups that either do not react or require strong catalysts or impractical reaction conditions in order to react (i.e., a "nonreactive" or "inert" group).

"Not readily reactive" or "inert" with reference to a functional group present on a molecule in a reaction mixture, indicates that the group remains largely intact under conditions effective to produce a desired reaction in the reaction mixture.

A "protecting group" is a moiety that prevents or blocks reaction of a particular chemically reactive functional group in a molecule under certain reaction conditions. The protecting group will vary depending upon the type of chemically reactive group being protected as well as the reaction conditions to be employed and the presence of additional reactive or protecting groups in the molecule. Functional groups which may be protected include, by way of example, carboxylic acid groups, amino groups, hydroxyl groups, thiol groups, carbonyl groups and the like. Representative protecting groups for carboxylic acids include esters (such as a p-methoxybenzyl ester), amides and hydrazides; for amino groups, carbamates (such as tert-butoxycarbonyl) and amides; for hydroxyl groups, ethers and esters; for thiol groups, thioethers and thioesters; for carbonyl groups, acetals and ketals; and the like. Such protecting groups are well-known to those skilled in the art and are described, for example, in T. W. Greene and G. M. Wuts, *Protecting Groups in Organic Synthesis*, Third Edition, Wiley, New York, 1999, and references cited therein.

A functional group in "protected form" refers to a functional group bearing a protecting group. As used herein, the term "functional group" or any synonym thereof is meant to encompass protected forms thereof.

The term "linker" is used herein to refer to an atom or a collection of atoms optionally used to link interconnecting moieties, such as a polymer segment and a maleimide. The linkers of the invention are generally hydrolytically stable.

A "physiologically cleavable" or "hydrolyzable" or "degradable" bond is a relatively weak bond that reacts with water (i.e., is hydrolyzed) under physiological conditions. The tendency of a bond to hydrolyze in water will depend not only on the general type of linkage connecting two central atoms but also on the substituents attached to these central atoms. Appropriate hydrolytically unstable or weak linkages include but are not limited to carboxylate ester, phosphate ester, anhydrides, acetals, ketals, acyloxyalkyl ether, imines, orthoesters, peptides and oligonucleotides, thioesters, thiolesters, and carbonates.

An "enzymatically degradable linkage" means a linkage that is subject to degradation by one or more enzymes.

A "hydrolytically stable" linkage or linker, for the purposes of the present invention, and in particular in reference to the polymers of the invention, refers to an atom or to a collection of atoms, that is hydrolytically stable under normal physiological conditions. That is to say, a hydrolytically stable linkage does not undergo hydrolysis under physiological conditions to any appreciable extent over an extended period of time. Examples of hydrolytically stable linkages include but are not limited to the following: carbon-carbon bonds (e.g., in aliphatic chains), ethers, amides, urethanes, amines, and the like. Hydrolysis rates of representative chemical bonds can be found in most standard chemistry textbooks.

A "hydrolytically stabilized maleimide ring", in reference to a polymer of the invention, is one that resists hydrolysis of the maleimide ring in comparison to the ring opening-stability of its linkerless polymer maleimide counterpart. For example, if a subject water soluble maleimide has a structure $CH_3O$—$(CH_2CH_2O)_{5K}$—$CH_2CH_2$—$C(O)$—$NH$—$CH_2$-1, 3-$C_6H_{10}$—$CH_2$-MAL, where the linker is —$C(O)$—$NH$—$CH_2$-1,3-$C_6H_{10}$—$CH_2$—, then the corresponding linkerless version to form a basis for comparison is $CH_3O$—$(CH_2CH_2O)_{5K}$—$CH_2CH_2$-MAL. Typically, such hydrolysis evaluations are carried out at pH 7.5 in phosphate buffer at room temperature and are measured by observing the UV absorption of the maleimide ring. So, a hydrolytically stabilized maleimide ring contained in a polymer reagent of the invention is one that has a degree of hydrolytic stability that is improved over that of its linkerless counterpart. Preferably, a hydrolytically stabilized maleimide ring in accordance with the invention results in a stabilized polymer maleimide having a hydrolysis half-life under the above-described conditions of at least about 16 hours, and more preferably of at least about 20 hours.

"Branched" in reference to the geometry or overall structure of a polymer refers to polymer having 2 or more polymer "arms". A branched polymer may possess 2 polymer arms, 3 polymer arms, 4 polymer arms, 6 polymer arms, 8 polymer arms or more. One particular type of highly branched polymer is a dendritic polymer or dendrimer, that for the purposes of the invention, is considered to possess a structure distinct from that of a branched polymer.

"Branch point" refers to a bifurcation point comprising one or more atoms at which a polymer splits or branches from a linear structure into one or more additional polymer arms.

A "dendrimer" is a globular, size monodisperse polymer in which all bonds emerge radially from a central focal point or core with a regular branching pattern and with repeat units that each contribute a branch point. Dendrimers exhibit certain dendritic state properties such as core encapsulation, making them unique from other types of polymers.

"Substantially" or "essentially" means nearly totally or completely, for instance, 95% or greater of some given quantity.

An "alkyl" or "alkylene" group, depending upon its position in a molecule and the number of points of attachment of the group to atoms other than hydrogen, refers to a hydrocarbon chain or moiety, typically ranging from about 1 to 20 atoms in length. Such hydrocarbon chains are preferably but not necessarily saturated unless so indicated and may be branched or straight chain, although typically straight chain is preferred. Exemplary alkyl groups include methyl, ethyl, propyl, butyl, pentyl, 1-methylbutyl, 1-ethylpropyl, 3-methylpentyl, hexyl, heptyl, and the like.

"Lower alkyl" or "lower alkylene" refers to an alkyl or alkylene group as defined above containing from 1 to 6 carbon atoms, and may be straight chain or branched, as exemplified by methyl, ethyl, n-butyl, i-butyl, t-butyl.

"Cycloalkyl" or "cycloalkylene", depending upon its position in a molecule and the number of points of attachment to atoms other than hydrogen, refers to a saturated or unsaturated cyclic hydrocarbon chain, including polycyclics such as bridged, fused, or spiro cyclic compounds, preferably made up of 3 to about 12 carbon atoms, more preferably 3 to about 8.

"Lower cycloalkyl" or "lower cycloalkylene" refers to a cycloalkyl group containing from 1 to 6 carbon atoms.

"Alicyclic" refers to any aliphatic compound that contains a ring of carbon atoms. An alicyclic group is one that contains a "cycloalkyl" or "cycloalkylene" group as defined above that is substituted with one or more alkyl or alkylenes.

"Non-interfering substituents" are those groups that, when present in a molecule, are typically non-reactive with other functional groups contained within the molecule.

The term "substituted" as in, for example, "substituted alkyl," refers to a moiety (e.g., an alkyl group) substituted with one or more non-interfering substituents, such as, but not limited to: $C_3$—$C_8$ cycloalkyl, e.g., cyclopropyl, cyclobutyl, and the like; halo, e.g., fluoro, chloro, bromo, and iodo; cyano; alkoxy, lower phenyl; substituted phenyl; and the like. For substitutions on a phenyl ring, the substituents may be in any orientation (i.e., ortho, meta, or para).

"Alkoxy" refers to an —O—R group, wherein R is alkyl or substituted alkyl, preferably $C_1$—$C_{20}$ alkyl (e.g., methoxy, ethoxy, propyloxy, benzyl, etc.), preferably $C_1$—$C_7$.

As used herein, "alkenyl" refers to a branched or unbranched hydrocarbon group of 1 to 15 atoms in length, containing at least one double bond, such as ethenyl, n-propenyl, isopropenyl, n-butenyl, isobutenyl, octenyl, decenyl, tetradecenyl, and the like.

The term "alkynyl" as used herein refers to a branched or unbranched hydrocarbon group of 2 to 15 atoms in length, containing at least one triple bond, ethynyl, n-propynyl, isopropynyl, n-butynyl, isobutynyl, octynyl, decynyl, and so forth.

"Aryl" means one or more aromatic rings, each of 5 or 6 core carbon atoms. Aryl includes multiple aryl rings that may be fused, as in naphthyl or unfused, as in biphenyl. Aryl rings may also be fused or unfused with one or more cyclic hydrocarbon, heteroaryl, or heterocyclic rings. As used herein, "aryl" includes heteroaryl.

"Heteroaryl" is an aryl group containing from one to four heteroatoms, preferably N, O, or S, or a combination thereof. Heteroaryl rings may also be fused with one or more cyclic hydrocarbon, heterocyclic, aryl, or heteroaryl rings.

"Heterocycle" or "heterocyclic" means one or more rings of 5-12 atoms, preferably 5-7 atoms, with or without unsaturation or aromatic character and having at least one ring atom which is not a carbon. Preferred heteroatoms include sulfur, oxygen, and nitrogen.

"Substituted heteroaryl" is heteroaryl having one or more non-interfering groups as substituents.

"Substituted heterocycle" is a heterocycle having one or more side chains formed from non-interfering substituents.

"Electrophile" refers to an ion, atom, or collection of atoms that may be ionic, having an electrophilic center, i.e., a center that is electron seeking, capable of reacting with a nucleophile.

"Nucleophile" refers to an ion or atom or collection of atoms that may be ionic, having a nucleophilic center, i.e., a center that is seeking an electrophilic center, and capable of reacting with an electrophile.

"Active agent" as used herein means any agent, drug, compound, composition of matter or mixture which provides some pharmacologic, often beneficial, effect that can be demonstrated in-vivo or in vitro. This includes foods, food supplements, nutrients, nutriceuticals, drugs, vaccines, antibodies, vitamins, and other beneficial agents. As used herein, these terms further include any physiologically or pharmacologically active substance that produces a localized or systemic effect in a patient.

"Pharmaceutically acceptable excipient" or "pharmaceutically acceptable carrier" refers to an excipient that can be included in the compositions of the invention and that causes no significant adverse toxicological effects to the patient.

"Pharmacologically effective amount," "physiologically effective amount," and "therapeutically effective amount" are used interchangeably herein to mean the amount of a PEG-active agent conjugate present in a pharmaceutical preparation that is needed to provide a desired level of active agent and/or conjugate in the bloodstream or in the target tissue. The precise amount will depend upon numerous factors, e.g., the particular active agent, the components and physical characteristics of pharmaceutical preparation, intended patient population, patient considerations, and the like, and can readily be determined by one skilled in the art, based upon the information provided herein and available in the relevant literature.

"Multi-functional" in the context of a polymer of the invention means a polymer backbone having 3 or more functional groups contained therein, where the functional groups may be the same or different, and are typically present on the polymer termini. Multi-functional polymers of the invention will typically contain from about 3-100 functional groups, or from 3-50 functional groups, or from 3-25 functional groups, or from 3-15 functional groups, or from 3 to 10 functional groups, or will contain 3, 4, 5, 6, 7, 8, 9 or 10 functional groups within the polymer backbone.

A "difunctional" polymer means a polymer having two functional groups contained therein, typically at the polymer termini. When the functional groups are the same, the polymer is said to be homodifunctional. When the functional groups are different, the polymer is said to be heterobifunctional A basic or acidic reactant described herein includes neutral, charged, and any corresponding salt forms thereof.

"Polyolefinic alcohol" refers to a polymer comprising an olefin polymer backbone, such as polyethylene, having multiple pendant hydroxyl groups attached to the polymer backbone. An exemplary polyolefinic alcohol is polyvinyl alcohol.

As used herein, "non-peptidic" refers to a polymer backbone substantially free of peptide linkages. However, the polymer may include a minor number of peptide linkages spaced along the repeat monomer subunits, such as, for example, no more than about 1 peptide linkage per about 50 monomer units.

The term "patient," refers to a living organism suffering from or prone to a condition that can be prevented or treated by administration of a polymer of the invention, typically but not necessarily in the form of a polymer-active agent conjugate, and includes both humans and animals.

"Optional" or "optionally" means that the subsequently described circumstance may or may not occur, so that the description includes instances where the circumstance occurs and instances where it does not.

By "residue" is meant the portion of a molecule remaining after reaction with one or more molecules. For example, a biologically active molecule residue in the polymer conjugate of the invention is the portion of a biologically active molecule remaining following covalent linkage to a polymer backbone.

The term "conjugate" is intended to refer to the entity formed as a result of covalent attachment of a molecule, e.g., a biologically active molecule or any reactive surface, to a reactive polymer molecule, preferably a reactive poly(ethylene glycol).

The term "electron withdrawing group" refers to a chemical moiety that brings electron density towards itself and away from other areas of a molecule through either mesomeric mechanisms (i.e., adding or removing local electron density through $\pi$ bonds) or inductive mechanisms (i.e., an electronegative moiety withdrawing electron density along a $\sigma$ bond, thereby polarizing the bond).

The term "steric hindrance" refers to spatial, mechanical interference between two chemical groups.

Stabilized Polymer Maleimides—General Features

The present invention provides water-soluble and non-peptidic polymers whose maleimide rings are hydrolytically stable in comparison to their linkerless maleimide counterparts. Generally, the feature of resistance to hydrolysis, i.e., with regard to the maleimide ring, is imparted by the introduction of a linker between the polymer segment and the maleimide. Typically, the linker comprises a saturated acyclic, cyclic, or alicyclic hydrocarbon chain covalently attached to, and immediately adjacent to, the nitrogen atom of the maleimide. The structure and size of the hydrocarbon chain, which may comprise alkylene groups, cycloalkyl groups, or combinations thereof, in either substituted or non-substituted form, is designed to retard ring opening of the maleimide by i) providing sufficient distance between the maleimide and any electron withdrawing groups in the linker or the polymer segment, thereby enabling electron release to the maleimide ring, and/or ii) providing steric hindrance to the hydrolytic process. In this manner, the linkers described herein stabilize the maleimide ring against hydrolysis and resultant ring-opening. Thus, the maleimide-terminated polymers of the invention exhibit greater stability, e.g., upon synthesis, isolation, and storage, and can be conjugated to biologically active molecules over a wider range of pH values without producing significant amounts of open-ring conjugates. Hydrolysis data provided herein is indicative of this point. The synthesis of representative stabilized polymer maleimides is described in Examples I, II, III, IV, V, IX, X, XI, and XII. As can be seen, linear acyclic, branched acyclic, and alicyclic linkers are all effective in enhancing the stability of the adjacent maleimide ring. Hydrolysis data illustrative of this feature for both the polymer reagents and their corresponding conjugates is provided in Examples VII, VII, and XIII.

The linkers as described in greater detail below may also include one or more non-hydrocarbon yet hydrolytically stable and non-reactive atoms or collection of atoms, such as hydroxyl, sulfur, oxygen, and the like.

The maleimide-functionalized polymers of the invention are preferably hydrolytically stable over a wide pH range, such as from about 5 to about 10. In particular, most preferably, the reactive polymer maleimides of the invention are hydrolytically stable at pHs suitable for conjugation to thiol or amino groups on biologically active molecules, such as proteins. For example, the polymers of the invention are preferably resistant to hydrolysis-induced maleimide ring opening (i.e., are not prone to formation of maleimic acid if unconjugated or formation of succinamidic acid if conjugated) at pHs ranging from about 7 to about 10, and more preferably at pHs from about 7 to about 8.5. As defined herein, a hydrolytically stable maleimide is one in which the half-life of the maleimide at 25° C. and a pH of 7.5 in an aqueous medium (e.g., phosphate buffer) is at least about 16 hours, more preferably at least about 20 hours, most preferably at least about 28 hours.

The half-life of a polymer maleimide can be determined by measuring the concentration of the maleimide-terminated polymer over time using HPLC or by observing the UV absorption of the maleimide ring.

The saturated acyclic, cyclic, or alicyclic hydrocarbon linker adjacent to the maleimide group preferably has a chain length of at least 3 carbon atoms and contains at least 3 contiguous carbon atoms. More preferably, the linker possesses at least about 4 carbon atoms, most preferably at least about 5 or 6 carbon atoms. The chain length is measured as the number of carbon atoms forming the shortest atom chain linking the nitrogen atom of the maleimide to the polymer segment. Typically, the total number of carbon atoms in the linker including chain substituents, ranges from 4 to about 20 atoms, preferably 4 to about 12 atoms, more preferably 4 to about 10 atoms and most preferably 5 to about 8 atoms. The invention includes linkers having, for example, 4, 5, 6, 7, 8, 9, 10, 11, and 12 total carbon atoms.

General Structural Features of the Polymer Maleimide

Generally speaking, the reactive polymers of the invention possesses a water soluble polymer segment that is connected to a maleimide ring via a hydrolytically stable linker. The hydrolytically stable linker is effective to impart hydrolytic stability to the maleimide ring to which it is directly covalently attached. More particularly, the polymer segment, referred to herein generally as POLY, is covalently attached to the hydrolytically stable linker, X, via an intervening —O—, —C(O)—NH—, or O—C(O)—NH— group. X typically contains at least 3 contiguous saturated carbon atoms. Preferably although not necessarily, the resultant polymer maleimide is absent aromatic groups and ester linkages.

Also provided herein are polymers having both the generalized and specific illustrative structural features described for the stabilized polymer maleimides, with the exception that the maleimide ring is replaced by an amino group, preferably a primary amino group. Thus, all structures and descriptions herein directed towards maleimide-terminated polymer reagents should be extended to their amino-terminated counterparts as described above.

The linker, X, typically contains from about 1 to about 20 carbon atoms. Generally, X is a hydrocarbon chain possessing only carbon and hydrogen atoms, however, in certain embodiments, X may contain additional non-reactive atoms or functional groups such as hydroxyl groups, ethers, thioethers, or other non-reactive groups. Preferably, such groups or atoms are positioned remote from the maleimide ring. More preferably, such non-reactive atoms or groups are positioned a distance of at least 4 carbons from the maleimide nitrogen. Even more preferably, such additional non-reactive atoms or groups contained in X are positioned at least 4 carbons, at least 5 carbons or at least 6 carbons or more distant from the maleimide nitrogen. Such groups are more likely to be contained within cycloalkyl or alicyclic X's than in their acyclic counterparts, simply due to their presence in many commercially available starting materials.

A polymer maleimide of the invention is generally characterized by the following formula:

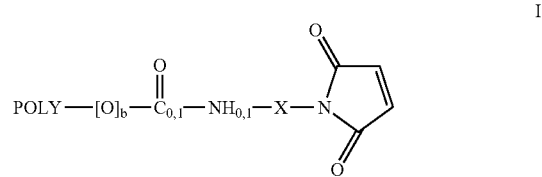

I where b is 0 or 1. In structure I, when both the carbonyl and —NH groups are absent (i.e., each subscript is equal to zero), b is equal to 1. Features of the linker X are described and exemplified in greater detail in the section that follows.

The Linker Moiety

As mentioned previously, the linker, X, comprises a saturated acyclic or cyclic or alicyclic hydrocarbon moiety adjacent to the nitrogen atom of the maleimide ring. The size and structure of X is designed to improve the hydrolytic stability of the maleimide ring, generally by increasing the distance between the maleimide ring and electron withdrawing groups present in the molecule or by providing steric hindrance to the maleimide hydrolysis reaction. Typically, X contains a total of about 3 to about 20 carbon atoms. More particularly, X can possess a total number of carbon atoms selected from the group consisting of 3, 4, 5, 6, 7, 8, 9, 10, 11, 12, 13, 14, 15, 16, 17, 18, 19, and 20. Preferred ranges for total number of carbon atoms in the linker X are from about 3 to about 20, or from about 4 to about 12, or from about 4 to about 10, or from about 5 to about 8 atoms.

Exemplary hydrocarbon linkages include straight chain saturated acyclic hydrocarbons comprising at least 3 contiguous carbon atoms, such as trimethylene, tetramethylene, pentamethylene, and hexamethylene, and so forth. That is to say, in its simplest form, X equals —$(CH_2)_y$—, where y ranges from 3 to about 20. That is to say, Y may possess any of the following values: 3, 4, 5, 6, 7, 8, 9, 10, 11, 12, 13, 14, 15, 16, 17, 18, 19, or 20. Alternatively, X can be branched, i.e., can contain one or even two substituents, at any one or more of the carbon positions in the chain. That is to say, X can be branched at the carbon α to the maleimidyl group, or at the carbon β to the maleimidyl group, or at the carbon γ to the maleimidyl group. For hydrocarbon chains having up to 19 carbon atoms, any one of positions 1 to 19 (with position 1 being the one proximal to the maleimide ring) may be branched. For instance, for an exemplary saturated hydrocarbon chain having from 2 to 19 carbon atoms designated $C_1$-$C_2$-$C_3$-$C_4$-$C_5$-$C_6$-$C_7$-$C_8$-$C_9$-$C_{10}$-$C_{11}$-$C_{12}$-$C_{13}$-$C_{14}$-$C_{15}$-$C_{16}$-$C_{17}$-$C_{18}$-$C_{19}$-, any one or more of carbons $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, or $C_{19}$, depending on the total number of carbons in the chain, may be branched, that is to say, may possess one or even two substituents. Typically, a branching group is an alkyl group, substituted alkyl, cycloalkyl, substituted cycloalkyl, alkylene cycloalkyl, or substituted cycloalkyl. Particularly preferred cycloalkyls are cyclopentyl, cyclohexyl, cycloheptyl, and the like, and any of the previous cycloalkyls having one or more methylene groups (e.g., methylene, dimethylene, trimethylene, tetramethylene, etc.) connecting the cycloalkyl ring to the branching carbon. Preferably, in any given saturated hydrocarbon chain or alicyclic linker, 4 or fewer carbon atoms are branched, with the overall number of branching positions preferably equal to 1, 2, 3, or 4. Embodiments wherein the "branch" points taken together form a saturated ring or ring system (e.g., bicyclic, tricyclic, etc.) are discussed separately below. Most preferably, when X is branched, the branching carbon is singly branched, i.e., has one rather than two branching substituents.

For example, the linkage may possess the structure —$(CR_1R_2)_y$—, wherein $R_1$ and $R_2$ are each independently H, alkyl, substituted alkyl, cycloalkyl, substituted cycloalkyl, alkylenecycloalkyl, and substituted alkylenecycloalkyl, and y is an integer from about 1 to about 20, preferably from about 3 to about 20, and even more preferably from 4 to about 12. When X is branched, preferably the branching is at one or more of C1, C1, C3, or C4, that is to say, the carbon atom positions closest to the maleimide ring, in order to provide maximal steric hindrance to the maleimide ring hydrolysis reaction. (When discussing carbon atom positions within the linker, X, C1 refers to the carbon atom adjacent to the maleimide nitrogen, and so on). When X is branched, the branching groups (e.g., alkyl, substituted alkyl, cycloalkyl, substituted cycloalkyl, alkylenecycloalkyl, and substituted alkylenecycloalkyl) typically contain fewer than 8 or so carbon atoms. When the branching group is alkyl or cycloalkyl, preferably the alkyl group is lower alkyl such as methyl, ethyl, propyl, isopropyl, butyl, isobutyl, penyl, cyclopentyl, hexyl, and cyclohexyl.

As dicussed above, the linker X itself can be cyclic or alicyclic. Specifically, X may possess the form:

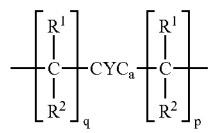

IV where $CYC_a$ is a cycloalkylene group having "a" ring carbons, where the value of "a" ranges from 3 to 12; p and q are each independently 0 to 20, and p+q+a≦20, $R^1$, in each occurrence, is independently H or an organic radical that is selected from the group consisting of alkyl, substituted alkyl, cycloalkyl, substituted cycloalkyl, alkylenecycloalkyl, and substituted alkylenecycloalkyl, and $R^2$, in each occurrence, is independently H or an organic radical that is selected from the group consisting of alkyl, substituted alkyl, cycloalkyl, substituted cycloalkyl, alkylenecycloalkyl, and substituted alkylenecycloalkyl. In a preferred embodiment, $R_1$ and $R_2$, in each occurrence, are both H. Preferably, p and q each independently are 0, 1, 2, 3, 4, 5, 6, 7, 8, 9, or 10. Even more preferably, p and q each independently range from 0 to 6 or 0 to 4. Preferably, the cycloalkyl ring represented by $CYC_a$ contains from 5 to about 12 ring carbon atoms, and even more preferably from about 6 to about 10 ring carbon atoms. Representative cycloalkyl groups include C3-C8 cycloalkylene, such as cyclopropylene, cyclobutylene, cyclopentylene, cyclohexylene, and cycloheptylene, and cyclooctylene. $CYC_a$ may optionally be substituted with one or more alkyl groups, preferably lower alkyl groups, which can be at any position within the ring. In instances where $CYC_a$ is substituted with only two substituents, i.e., $(CR_1R_2)_p$ and $(CR_1R_2)_q$ as shown in structure IV above, the substituents can similarly be positioned on any one or more carbons in the ring. For instance, for a cyclopenylene, the substituents can be at either the 1,1-, 1,2-, or 1,3-positions. For a cyclohexylene ring, the substituents can be at the 1,1-, 1,2-, 1,3-, or 1,4-positions. Particularly preferred embodiments are those where $R_1$ and $R_2$ are H in all instances, and p and q are each independently selected from 0, 1, 2, and 3. Illustrative linkers include 1,2-$(CH_2)_{0,1,2,3}$—$C_6H_4$—$(CH_2)_{0,1,2,3}$, and 1,3-$(CH_2)_{0,1,2,3}$—$C_6H_4$—$(CH_2)_{0,1,2,3}$, and 1,4-$(CH_2)_{0,1,2,3}$—$C_6H_4$—$(CH_2)_{0,1,2,3}$—. In instances in which $CYC_a$ possesses only two substituents, the substituents may be either cis or trans. When $CYC_a$ contains more than two substituents, the substituents may be in any relative orientation to one another.

$CYC_a$ also encompasses bicyclic rings. Exemplary bicyclic rings corresponding to $CYC_a$ include rings such as bicyclo[1.1.1]pentane, bicyclo[2.2.1]hexane, bicyclo[2.2.1]heptane, bicycle[2.2.2]octane, bicyclo[3.1.0]hexane, bicyclo[3.1.1]heptane, bicyclo[3.2.1]octane, bicyclo[3.3.1]nonane, bicyclo[3.3.2]decane, bicyclo[3.3.3]undecane and the like. CYC also encompasses tricyclic ring systems such as adamantane. Some of these bi- and tricyclic systems are shown below:

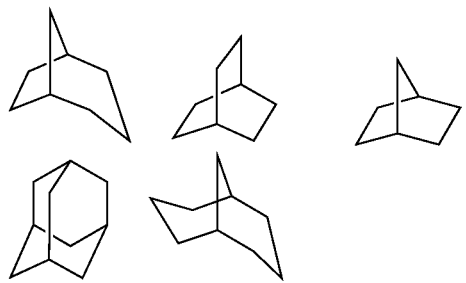

Figure 1B:
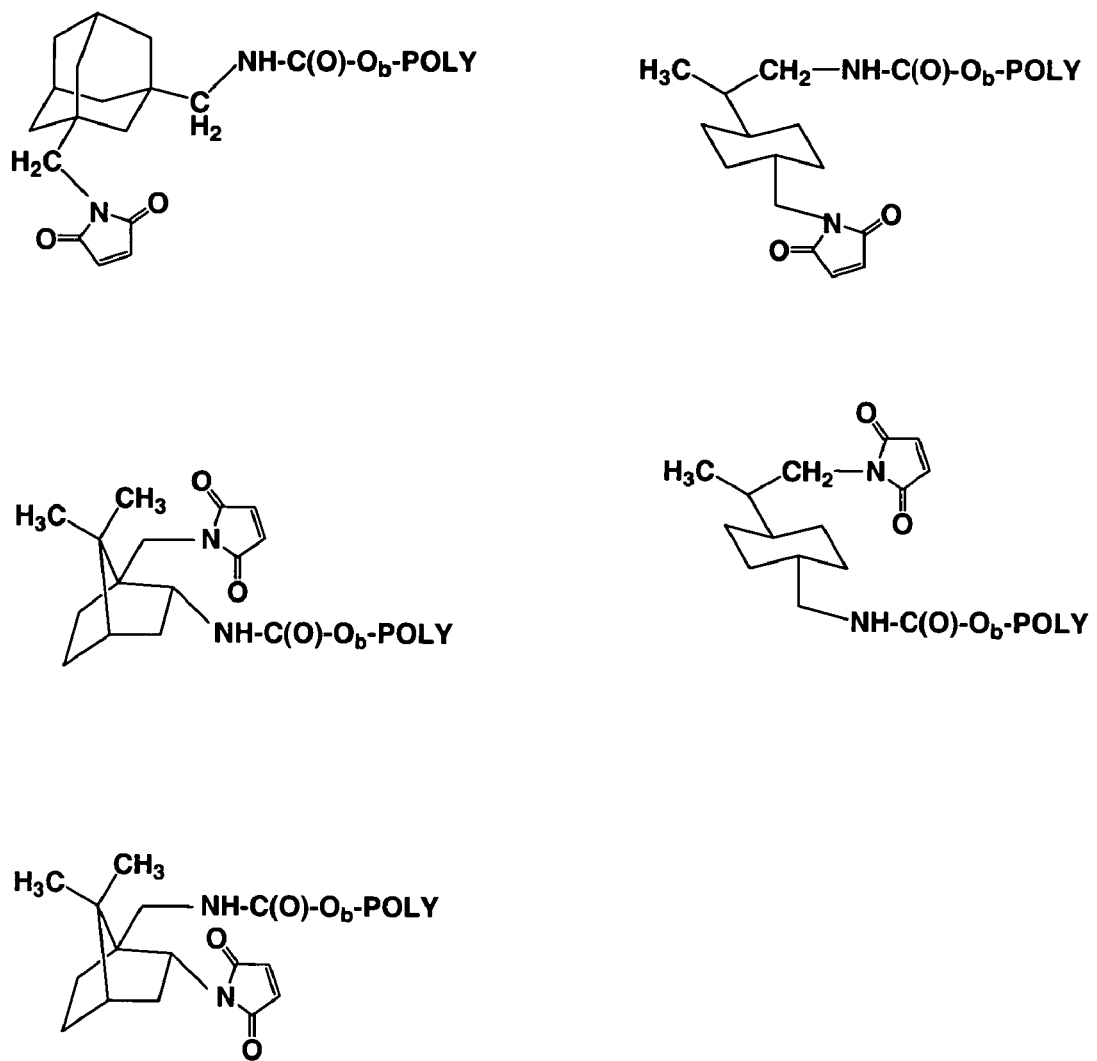

These rings may possess alkylene or substituted alkylene groups corresponding to —$[C(R_1)(R_2)]_p$ and —$[C(R_1)(R_2)]_q$ in any available position within the ring system. Moreover, the bicyclic or tricyclic ring may also possess additional substituents in addition to —$[C(R_1)(R_2)]_p$ and —$[C(R_1)(R_2)]_q$. Preferably, such substituents are lower alkyl, hydroxyl, sulfhydryl, or halide. Representative polymer maleimides having bi- and tricyclic ring systems are provided in FIGS. 1A and 1B.

The linkage, L, in structure I may further include a non-hydrocarbon portion adjacent to the polymer segment and interconnected to X as described above. Exemplary non-hydrocarbon portions adjacent to the polymer segment include —O—, —O—C(O)—NH—, —C(O)—NH—, —$CH_2$—C(O)—NH—, —NH—C(O)—O—, NH—C(O)—NH—, —NH—, and —S—, and are preferably hydrolytically stable. Particularly preferred non-hydrocarbon portions include —O—, —O—C(O)—NH—, —C(O)—NH—. In a less preferred embodiment, the nitrogen amide of the amide or carbamate function is a tertiary nitrogen, e.g., having a methyl or ethyl or similar group in place of the hydrogen as shown.

Exemplary linkages including a hydrocarbon chain according to the present invention are shown in Table 1 below.

TABLE 1

Exemplary linkers for Maleimide-Terminated Polymers

POLY—L—N(maleimide)

| | |
|---|---|
| $L_1 =$ | —NH—C(O)—P— |

| Designation | P |
|---|---|
| L1-AMDE | ethylene, —(CH$_2$)$_2$— |
| L1-AMPE | pentamethylene, —(CH$_2$)$_5$— |

L1-MCH: cyclohexyl-CH$_2$—

L1-TEPE: CH$_3$CH$_2$—O—(CH$_2$CH$_2$O)$_4$—C(O)—NH—CH$_2$—CH(CH$_3$)—CH$_2$—

| | |
|---|---|
| $L_2 =$ | —NH—Q— |

| Designation | Q |
|---|---|
| L2-TEME | tetramethylene, —(CH$_2$)$_4$— |
| L2-HEXA | hexamethylene, —(CH$_2$)$_6$— |

L2-EPEN: —CH(CH$_2$CH$_3$)—CH$_2$— (branched, with H$_3$C group)

| | |
|---|---|
| $L_3 =$ | —O—Z |

| Designation | Z |
|---|---|
| L3-ET | ethylene, —(CH$_2$)$_2$— |
| L3-TME | trimethylene, —(CH$_2$)$_3$— |
| L3-TEME | tetramethylene, —(CH$_2$)$_4$— |
| L3-PENT | pentamethylene, —(CH$_2$)$_5$— |
| L3-HEXA | hexamethylene, —(CH$_2$)$_6$— |

| | |
|---|---|
| $L_4 =$ | —CH$_2$—W— |

| Designation | W |
|---|---|
| L4-PAHE | —C(O)NH—(CH$_2$)$_6$— |
| L4-BAHE | —CH$_2$—C(O)NH—(CH$_2$)$_6$— |

L4-TMPA: —C(O)NH—C(CH$_3$)$_2$—CH$_2$—C(CH$_3$)$_2$—

L4-ETPA: —C(O)NH—CH$_2$—CH$_2$—CH(CH$_3$)—CH$_2$CH$_3$

TABLE 1-continued

Exemplary linkers for Maleimide-Terminated Polymers

POLY—L—N(maleimide)

L4-HEDA: —C(O)NH—cyclohexyl—

L4-CMEN: —C(O)—NH—(menthane-derived cyclohexyl with H$_3$C and C(CH$_3$)$_2$CH$_3$ substituents)

—C(O)—NH—CH$_2$—cyclohexyl—CH$_2$—

—C(O)—NH—CH$_2$—cyclohexyl

—C(O)—NH—cyclohexyl

—C(O)—NH—CH$_2$—cyclohexyl—CH$_2$—

| | |
|---|---|
| $L_5 =$ | —O—C(O)—NH—V— |

| Designation | V |
|---|---|
| L5-TMPE | —C(CH$_3$)$_2$—CH$_2$—C(CH$_3$)$_2$—CH$_2$— (neopentyl-type) |
| L5-HEXA | —(CH$_2$)$_6$— |

Many of the linkages in Table 1 are effective to retard hydrolysis of the maleimide ring, although some are more effective than others. Several linkages in Table 1 provide steric hindrance to attack of the maleimide ring nitrogen by water, making the maleimide resistant to hydrolysis. These linkers include those comprising L4-TMPA, L4-CMEN, L5-TMPE, L1-TEPE, L2-EPEN, L4-ETPA and L4-HEDA. Linkers comprising L4-TMPA and L5-TMPE, which are based on the readily available corresponding symmetrical tertiary diamine, and L4-CMEN, which is based on the commercially available diamine derivative of naturally occurring p-menthane, are exemplary linkages that reduce the rate of hydrolysis of the maleimide ring by providing both steric hindrance and adequate spacing between the ring and electron withdrawing groups. Particularly preferred are linkers containing a cyclohexylene ring, as can be seen from the hydrolysis data provided in Table 4. As can be seen from the hydrolysis data, the 1,3-dimethylene-cyclohexylene linker imparts to the resultant PEG-maleimide a particular stability towards hydrolysis. In fact, its hydrolysis half life is 8 times longer than that of its linkerless maleimide counterpart. The 1,4-dimethylene-cyclohexylene linker also results in a stable maleimide polymer having a hydrolysis half life that is over two and half times longer that that of its linkerless maleimide counterpart.

The Polymer Segment

As shown in the illustrative structures above, a maleimide terminated polymer of the invention contains a water-soluble polymer segment. Representative POLYs include poly(alkylene glycols) such as poly(ethylene glycol), poly(propylene glycol) ("PPG"), copolymers of ethylene glycol and propylene glycol, poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazoline, and poly(N-acryloylmorpholine). POLY can be a homopolymer, an alternating copolymer, a random copolymer, a block copolymer, an alternating tripolymer, a random tripolymer, or a block tripolymer of any of the above. The water-soluble polymer segment is preferably, although not necessarily, a poly(ethylene glycol) "PEG" or a derivative thereof.

The polymer segment can have any of a number of different geometries, for example, POLY can be linear, branched, or forked. Most typically, POLY is linear or is branched, for example, having 2 polymer arms. Although much of the discussion herein is focused upon PEG as an illustrative POLY, the discussion and structures presented herein can be readily extended to encompass any of the water-soluble polymer segments described above.

Any water-soluble polymer having at least one reactive terminus can be used to prepare a polymer maleimide in accordance with the invention and the invention is not limited in this regard. Although water-soluble polymers bearing only a single reactive terminus can be used, polymers bearing two, three, four, five, six, seven, eight, nine, ten, eleven, twelve or more reactive termini suitable for conversion to a stabilized polymer maleimide as set forth herein can be used. Advantageously, as the number of hydroxyl or other reactive moieties on the water-polymer segment increases, the number of available sites for introducing a linkered maleimido group increases. Nonlimiting examples of the upper limit of the number of hydroxyl and/or reactive moieties associated with the water-soluble polymer segment include from about 1 to about 500, from 1 to about 100, from about 1 to about 80, from about 1 to about 40, from about 1 to about 20, and from about 1 to about 10.

In turning now to the preferred POLY, PEG encompasses poly(ethylene glycol) in any of its linear, branched or multi-arm forms, including end-capped PEG, forked PEG, branched PEG, pendant PEG, and less preferably, PEG containing one or more degradable linkage separating the monomer subunits, to be more fully described below. In one embodiment of the invention, the polymer segment is absent an ester linkage.

A PEG polymer segment comprises the following: —(CH$_2$CH$_2$O)$_n$—CH$_2$CH$_2$—, where (n) typically ranges from about 3 to about 4,000, or from about 3 to about 3,000, or more preferably from about 20 to about 1,000.

POLY can also be end-capped, for example an end-capped PEG where PEG is terminally capped with an inert end-capping group. Preferred end-capped PEGs are those having as an end-capping moiety such as alkoxy, substituted alkoxy, alkenyloxy, substituted alkenyloxy, alkynyloxy, substituted alkynyloxy, aryloxy, substituted aryloxy. Preferred end-capping groups are methoxy, ethoxy, and benzyloxy. The end-capping group can also advantageously comprise a phospholipid, although the polymer may also be absent a lipid. Exemplary phospholipids include phosphatidylcholines, such as dilauroylphosphatidylcholine, dioleylphosphatidylcholine, dipalmitoylphosphatidylcholine, disteroylphosphatidylcholine, behenoylphosphatidylcholine, arachidoylphosphatidylcholine, and lecithin.

Referring now to any of the structures containing a polymer segment, POLY, POLY may correspond or comprise the following:

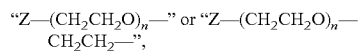

where n ranges from about 3 to about 4000, or from about 10 to about 4000, and Z is or includes a functional group, which may be a reactive group or an end-capping group. Examples of Z include hydroxy, amino, ester, carbonate, aldehyde, acetal, aldehyde hydrate, ketone, ketal, ketone hydrate, alkenyl, acrylate, methacrylate, acrylamide, sulfone, thiol, carboxylic acid, isocyanate, isothiocyanate, hydrazide, urea, maleimide, vinylsulfone, dithiopyridine, vinylpyridine, iodoacetamide, alkoxy, benzyloxy, silane, lipid, phospholipid, biotin, and fluorescein, including activated and protected forms thereof where applicable. Preferred are functional groups such as N-hydroxysuccinimidyl ester, benzotriazolyl carbonate, amine, vinylsulfone, maleimide, N-succinimidyl carbonate, hydrazide, succinimidyl propionate, succinimidyl butanoate, succinimidyl succinate, succinimidyl ester, glycidyl ether, oxycarbonylimidazole, p-nitrophenyl carbonate, aldehyde, orthopyridyl-disulfide, and acrylol.

These and other functional groups, Z, are described in the following references, all of which are incorporated by reference herein: N-succinimidyl carbonate (see e.g., U.S. Pat. Nos. 5,281,698, 5,468,478), amine (see, e.g., Buckmann et al. Makromol. Chem. 182:1379 (1981), Zalipsky et al. Eur. Polym. J. 19:1177 (1983)), hydrazide (See, e.g., Andresz et al. Makromol. Chem. 179:301 (1978)), succinimidyl propionate and succinimidyl butanoate (see, e.g., Olson et al. in Poly(ethylene glycol) Chemistry & Biological Applications, pp 170-181, Harris & Zalipsky Eds., ACS, Washington, D.C., 1997; see also U.S. Pat. No. 5,672,662), succinimidyl succinate (See, e.g., Abuchowski et al. Cancer Biochem. Biophys. 7:175 (1984) and Joppich et al., Makromol. Chem. 180:1381 (1979), succinimidyl ester (see, e.g., U.S. Pat. No. 4,670, 417), benzotriazole carbonate (see, e.g., U.S. Pat. No. 5,650, 234), glycidyl ether (see, e.g., Pitha et al. Eur. J. Biochem. 94:11 (1979), Elling et al., Biotech. Appl. Biochem. 13:354 (1991), oxycarbonylimidazole (see, e.g., Beauchamp, et al., Anal. Biochem. 131:25 (1983), Tondelli et al. J. Controlled Release 1:251 (1985)), p-nitrophenyl carbonate (see, e.g., Veronese, et al., Appl. Biochem. Biotech., 11:141 (1985); and Sartore et al., Appl. Biochem. Biotech., 27:45 (1991)), aldehyde (see, e.g., Harris et al. J. Polym. Sci. Chem. Ed. 22:341 (1984), U.S. Pat. No. 5,824,784, U.S. Pat. No. 5,252,714), maleimide (see, e.g., Goodson et al. Bio/Technology 8:343 (1990), Romani et al. in Chemistry of Peptides and Proteins 2:29 (1984)), and Kogan, Synthetic Comm. 22:2417 (1992)), orthopyridyl-disulfide (see, e.g., Woghiren, et al. Bioconj. Chem. 4:314 (1993)), acrylol (see, e.g., Sawhney et al., Macromolecules, 26:581 (1993)), vinylsulfone (see, e.g., U.S. Pat. No. 5,900,461).

Again, the POLY structures shown immediately above may represent linear polymer segments, or may form part of a branched or forked polymer segment. In an instance where the polymer segment is branched, the POLY structures immediately above may, for example, correspond to the polymer arms forming part of the overall POLY structure. Alternatively, in an instance where POLY possesses a forked structure, the above POLY structure may, for example, correspond to the linear portion of the polymer segment prior to the branch point.

POLY may also correspond to a branched PEG molecule having 2 arms, 3 arms, 4 arms, 5 arms, 6 arms, 7 arms, 8 arms or more. Branched polymers used to prepare the polymer maleimides of the invention may possess anywhere from 2 to 300 or so reactive termini. Preferred are branched polymer segments having 2 or 3 polymer arms. An illustrative branched POLY, as described in U.S. Pat. No. 5,932,462, corresponds to the structure:

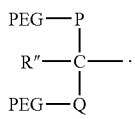

In this representation, R" is a nonreactive moiety, such as H, methyl or a PEG, and P and Q are nonreactive linkages. In a preferred embodiment, the branched PEG polymer segment is methoxy poly(ethylene glycol) disubstituted lysine.

In the above particular branched configuration, the branched polymer segment possesses a single reactive site extending from the "C" branch point for positioning of the reactive maleimide group via a linker as described herein. Branched PEGs such as these for use in the present invention will typically have fewer than 4 PEG arms, and more preferably, will have 2 or 3 PEG arms. Such branched PEGs offer the advantage of having a single reactive site, coupled with a larger, more dense polymer cloud than their linear PEG counterparts.

One particular type of branched PEG maleimide corresponds to the structure: (MeO-PEG-)$_i$G-[O]$_b$—C(O)—NH—X-MAL, where MAL represents maleimide, i equals 2 or 3, and G is a lysine or other suitable amino acid residue.

An illustrative branched polymer maleimide of the invention has the structure shown below, where X is any of the herein described hydrolytically stable linkers.

XVII

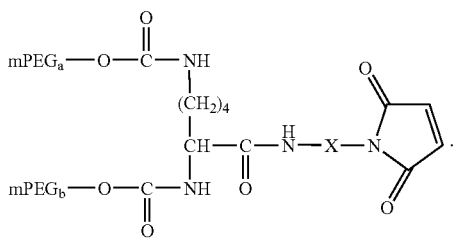

The synthesis of a polymer of the invention having the structural features embodied in XVIII above is provided in Example 1. Branched PEGs for use in preparing a polymer maleimide of the invention additionally include those represented more generally by the formula R(PEG)$_n$, where R is a central or core molecule from which extends 2 or more PEG arms. The variable n represents the number of PEG arms, where each of the polymer arms can independently be end-capped or alternatively, possess a reactive functional group at its terminus, such as a maleimide or other reactive functional group. In such multi-armed embodiments of the invention, each PEG arm typically possesses a maleimide group at its terminus. Branched PEGs such as those represented generally by the formula, R(PEG)$_d$, above possess 2 polymer arms to about 300 polymer arms (i.e., n ranges from 2 to about 300). Branched PEGs such as these preferably possess from 2 to about 25 polymer arms, more preferably from 2 to about 20 polymer arms, and even more preferably from 2 to about 15 polymer arms or fewer. Most preferred are multi-armed polymers having 3, 4, 5, 6, 7 or 8 arms.

Preferred core molecules in branched PEGs as described above are polyols. Such polyols include aliphatic polyols having from 1 to 10 carbon atoms and from 1 to 10 hydroxyl groups, including ethylene glycol, alkane diols, alkyl glycols, alkylidene alkyl diols, alkyl cycloalkane diols, 1,5-decalin-diol, 4,8-bis(hydroxymethyl)tricyclodecane, cycloalkylidene diols, dihydroxyalkanes, trihydroxyalkanes, and the like. Cycloaliphatic polyols may also be employed, including straight chained or closed-ring sugars and sugar alcohols, such as mannitol, sorbitol, inositol, xylitol, quebrachitol, threitol, arabitol, erythritol, adonitol, dulcitol, facose, ribose, arabinose, xylose, lyxose, rhamnose, galactose, glucose, fructose, sorbose, mannose, pyranose, altrose, talose, tagitose, pyranosides, sucrose, lactose, maltose, and the like. Additional aliphatic polyols include derivatives of glyceraldehyde, glucose, ribose, mannose, galactose, and related stereoisomers. Other core polyols that may be used include crown ether, cyclodextrins, dextrins and other carbohydrates such as starches and amylose. Preferred polyols include glycerol, pentaerythritol, sorbitol, and trimethylolpropane.

A representative multi-arm polymer structure of the type described above is:

VI

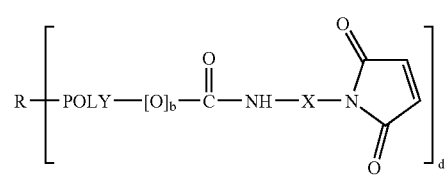

where d is an integer from 3 to about 100, and R is a residue of a central core molecule having 3 or more hydroxyl groups, amino groups, or combinations thereof.

Multi-armed PEGs for use in preparing a polymer maleimide of the invention include multi-arm PEGs available from Nektar, Huntsville, Ala. In a preferred embodiment, a multi-armed polymer maleimide of the invention corresponds to the following, where the specifics of the linkered maleimide portion of the molecule are provided elsewhere herein.

VII

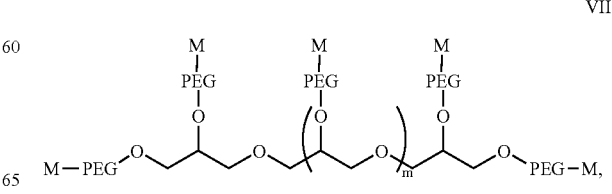

where

PEG is —(CH$_2$CH$_2$O)$_n$CH$_2$CH$_2$—,

M is:

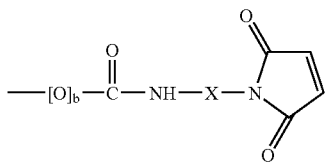

and m is selected from the group consisting of 3, 4, 5, 6, 7, and 8.

Alternatively, the polymer maleimide may possess an overall forked structure. An example of a forked PEG corresponds to the structure:

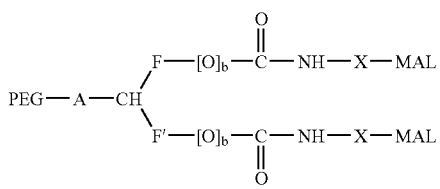

XVIII where PEG is any of the forms of PEG described herein, A is a linking group, preferably a hydrolytically stable linkage such as oxygen, sulfur, or —C(O)—NH—, F and F' are hydrolytically stable spacer groups that are optionally present, and the other variables corresponding to the hydrolytically stable linker, X, and maleimide (MAL) portion are as defined above. Both the general and specific descriptions of possible values for X are applicable to the embodiment above, structure XVIII. Examplary linkers and spacer groups corresponding to A, F and F' are described in International Application No. PCT/US99/05333, and are useful in forming polymer segments of this type for use in the present invention. F and F' are spacer groups that may be the same of different. In one particular embodiment of the above, PEG is mPEG, A corresponds to —C(O)—NH—, and F and F' are both methylene or —CH$_2$—. This type of polymer segment is useful for reaction with two active agents, where the two active agents are positioned a precise or predetermined distance apart, depending upon the selection of F and F'.

Another version of a polymer reagent of the invention having a forked polymer segment corresponds to:

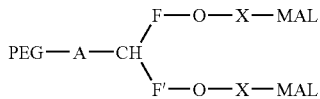

XIX where the variables are as described above. Preferably, X in this embodiment is a saturated cyclic or alicyclic hydrocarbon chain having a total of 3 to about 20 carbon atoms.

An exemplary branched PEG corresponding to "PEG" in the above formula is mPEG disubstituted lysine, where "PEG" corresponds to:

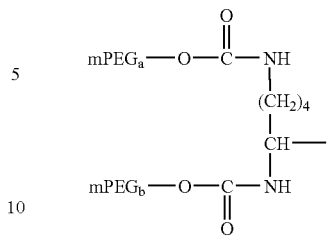

Alternatively, the PEG polymer segment for use in preparing a polymer maleimide of the invention may be a PEG molecule having pendant reactive groups along the length of the PEG chain rather than at the end(s), to yield a stabilized polymer maleimide having one or more pendant maleimide groups attached to the PEG chain by a linker, X.

Further, in a less preferred embodiment, the polymer segment itself may possess one or more weak or degradable linkages that are subject to hydrolysis. Illustrative degradable linkages that may be present in the polymer segment include but are not limited to carbonate, imine, phosphate ester, and hydrazone.

Generally, the nominal average molecular mass of the water-soluble polymer segment, POLY will vary. The nominal average molecular mass of POLY typically falls in one or more of the following ranges: about 100 daltons to about 100,000 daltons; from about 500 daltons to about 80,000 daltons; from about 1,000 daltons to about 50,000 daltons; from about 2,000 daltons to about 25,000 daltons; from about 5,000 daltons to about 20,000 daltons. Exemplary nominal average molecular masses for the water-soluble polymer segment POLY include about 1,000 daltons, about 5,000 daltons, about 10,000 daltons, about 15,000 daltons, about 20,000 daltons, about 25,000 daltons, about 30,000 daltons, and about 40,000 daltons. Low molecular weight POLYs possess molecular masses of about 250, 500, 750, 1000, 2000, or 5000 daltons.

Polymer Amines

The present invention also extends to amine counterparts of any and all of the above-described structures, with the exception that the heretofore described maleimide ring is replaced with an amino group, preferably —NH$_2$.

More particularly, the invention extends to a water-soluble polymer having the structure:

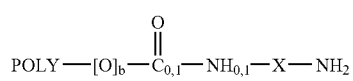

VIII where POLY, b and X are as described above.

Representative polymer amines include those having the generalized structures shown below:

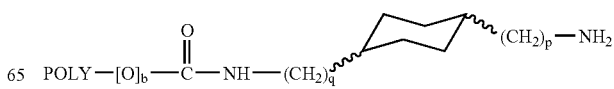

VIII-C wherein q and p each independently range from 0 to 6, and the substituents on said cyclohexylene ring are either cis or trans.

VIII-D

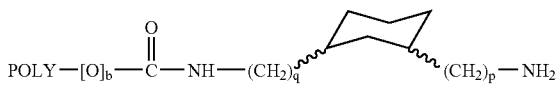

wherein q and p each independently range from 0 to 6, and the substituents on said cyclohexylene ring are either cis or trans.

The amine-terminated polymers represented generally by VIII have a number of uses to be described in greater detail below. For instance, they can be converted to the corresponding maleimide-terminated polymers of the invention, or alternatively, used without further modification for covalent attachment to active agents or surfaces, or for forming hydrogels.

Hyrolytic Stability and Methods of Preparation

As described above, the polymer maleimides provided herein are resistant to hydrolysis, as demonstrated for both the polymer reagents themselves (Examples VII and XIII) and for their corresponding conjugates (Example VIII). A polymer maleimide of the invention has a hydrolysis half-life that is longer than that of its linkerless polymer maleimide counterpart, when measured under the same conditions. That is to say, a Tinkered polymer maleimide of the invention possesses a rate of hydrolysis that is slower than that of its corresponding linkerless version, meaning that the maleimide ring remains intact longer under essentially the same conditions. For instance, in looking at the hydrolysis data in Examples 7 and 14, Tables 2 and 4, each of the representative linkers has a hydrolysis half-life that is extended over that of the linkerless maleimide ("3-ET").

The polymer maleimides of the invention can be prepared by a number of alternative routes including the following. In one approach, a maleimide-terminated polymer of the invention is prepared by reacting a functional group attached to a polymer segment (i.e., an activated polymer segment) with a functional group attached to a bifunctional linker. Reacting the polymer segment with a bifunctional linker reagent results in covalent attachment, through a hydrolytically stable linkage, of the linker to the polymer segment. The remaining functional group on the bifunctional linker reagent is either a maleimide or a functional group that can be readily converted to a maleimide.

For example, the linker reagent may possess the structure A-L-B, wherein A is a first functional group that is reactive with a second functional group on the polymer segment to thereby form a hydrolytically stable linkage, L, to form POLY-L-B, where B is a maleimide or a functional group that can be readily converted to a maleimide (e.g., an amine that can be converted to a maleimide by reaction with methoxycarbonylmaleimide). In the above approach, A can be any of a number of functional groups such as halo, hydroxyl, active ester such as N-succinimidyl ester, active carbonate, acetal, aldehyde, aldehyde hydrate, alkenyl, acrylate, methacrylate, acrylamide, active sulfone, thiol, carboxylic acid, isocyanate, isothiocyanate, maleimide, vinylsulfone, dithiopyridine, vinylpyridine, iodoacetamide, and epoxide. Particular examples of linker reagents include 1,4-dibromobutane, 1,5-dibromopentane, 1,6-dibromohexane, N-succinimidyl ϵ-maleimidohexanoate), N-succinimidyl(ϵ-maleimidopentanoate), N-(γ-maleimidobutryloxy)succinimide ester, N-(γ-maleimidocaproyloxy)succinimide ester, 4,7,10-trioxa-1,3-tridecanediamine, 4-(maleimidomethyl)-1-cyclohexanecarboxylic acid—NHS ester, tetramethylenediamine, pentamethylenediamine, hexamethylenediamine, 2,5-diamino-2,5-dimethylhexane, 1,3-cyclohexylbis(methylamine), and 1,4-cyclohexylbis(methylamine). Such linker reagents are either commercially available, for example from Pierce Chemical Company, or can be prepared from commercially available starting materials using methodology known in the art.

This approach is shown more particularly as method 1 below, as it relates to the formation of polymer malemides containing an amide or urethane bond connecting the polymer segment to the linker, X.

Method 1.

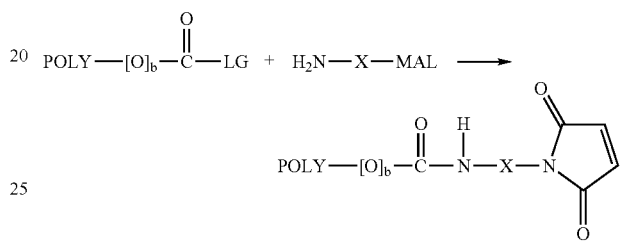

In a method similar to the above, designated method 2, the reactive polymer starting material, POLY-[O]$_b$—C(O)-LG, is reacted with a diamine reagent, H$_2$N—X—NH$_2$, to form the corresponding polymer amine intermediate, POLY-[O]$_b$—C(O)—HN—X—NH. This intermediate is then converted to the corresponding stabilized maleimide-terminated polymer. This method is advantageous in that many diamine reagents suitable for forming a stabilized polymer maleimide as described herein are commercially available. Moreover, polymer-amine intermediates can be more easily purified than their maleimide counterparts, e.g., by column chromatography, to thereby provide a polymer maleimide product that is significantly absent other undesirable polymer-derived sideproducts, such as PEG-diol and PEG-diol derived impurities. Method 2 is shown below.

Method 2.

Generalized Reaction Scheme.

Step a.

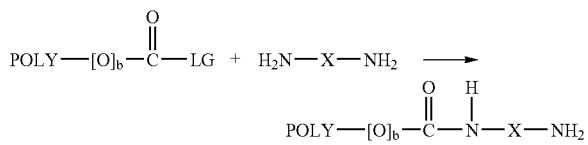

Step b.

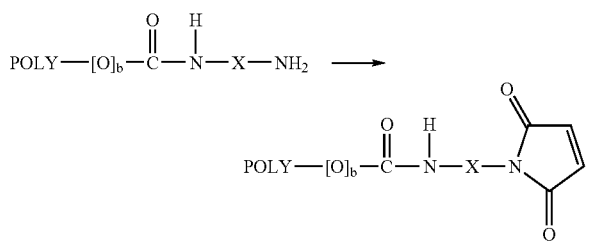

In methods 1 and 2, LG represents a leaving group, while the other variables are as described previously. The reactive polymer starting material, POLY-$[O]_b$—C(O)-LG, may be, for example, an acyl halide, a haloformate, an anhydride, or an active ester. Leaving groups useful in the methods include halides (e.g., chloro, bromo, and iodo), N-hydroxysuccinimide, N-hydroxybenzotriazole, and para-nitrophenolate. The coupling reaction to form the amide or urethane bond is generally carried out in a dry organic solvent, preferably under an inert atmosphere such as nitrogen or argon. Suitable solvents include acetonitrile, chlorinated hydrocarbons such as chloroform and dichloromethane, aromatic hydrocarbons such as benzene, toluene, and xylene, and solvents such as acetone, and tetrahydrofuran. The reaction is typically carried out at temperatures ranging from about 0 to 100° C., depending upon the type of solvent employed and the reactivity of the particular reagents themselves. The coupling is generally conducted in the presence of a base. Bases include trialkylamines such as triethyl amine, pyridine, 4-(dimethylamino) pyridine, and inorganic bases such as sodium carbonate.

Figure 2:
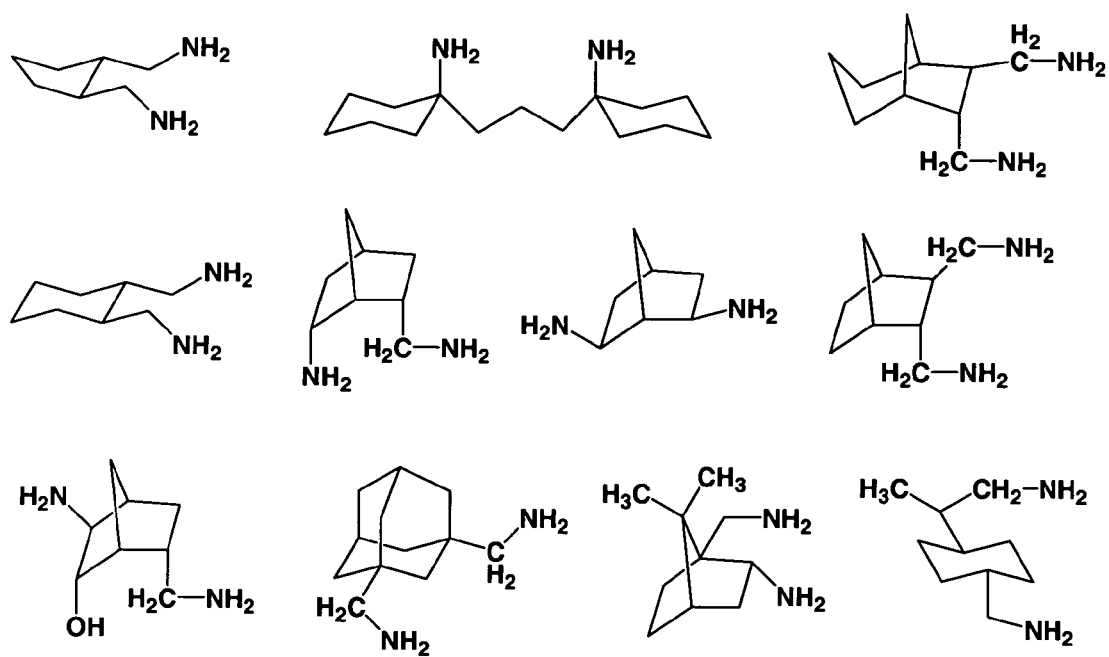

Representative bicyclic and tricyclic diamine reactants corresponding to $H_2N$—X—$NH_2$ in method 2 above are provided in FIG. 2. In method 2, it may be necessary in certain instances to protect one of the amino groups in $H_2N$—X—$NH_2$ using, for example, a conventional amino-protecting group such as t-BOC or FMOC. The protecting group in POLY-$[O]_b$—C(O)—HN—X—NH is then typically removed prior to further purification or transformation. See for example, Examples 10 and 11. In instances where purification of the intermediate polymer amine is undertaken, any of a number of purification approaches can be used such as precipitation or chromatography, although preferred is ion exchange chromatography due to the presence of an amino group on the intermediate polymer amine.

In continuing with the approach in method 2, the intermediate polymer amine is then converted to the corresponding maleimide. Generally, this conversion is carried out by reacting POLY-$[O]_b$—C(O)—$H_2N$—X—$NH_2$ with a reagent such as N-methoxycarbonylmaleimide, exo-7-oxa[2.2.1]bicycloheptane-2,3-dicarboxylic anhydride, or maleic anhydride, under conditions suitable for forming POLY-$[O]_b$—C(O)—$H_2N$—X-MAL.

A preferred reagent is N-methoxycarbonylmaleimide, and in this instance, the conversion to the maleimide is carried out in water or an aqueous mixture of water and a water miscible solvent such as acetonitrile or acetone. The conversion reaction is generally carried out at temperatures ranging from about 0 to 80° C., at pHs ranging from about 6.5 to 9

When the reagent is maleic anhydride, POLY-$[O]_b$—C(O)—$H_2N$—X—$NH_2$ is reacted with maleic anhydride under conditions effective to form POLY-$[O]_b$—C(O)—NH—X—NH—C(O)CH═CHCOOH (XI) as an intermediate. This intermediate is then heated under conditions effective to promote cyclization by elimination of water to form POLY-$[O]_b$—C(O)—NH—X-MAL. The efficiency of the cyclization reaction to form the maleimide ring typically ranges from about 15 to about 80 percent.

Generally, the product, POLY-$[O]_b$—C(O)—$H_2N$—X-MAL is recovered from the reaction mixture, and optionally further purified. In instances where the product is formed by method 2, further purification, for example, to remove polymer-derived impurities, may be unnecessary if purification is carried out on the amine-precursor, for example, by ion exchange chromatography. Preferably, the recovered product, POLY-$[O]_b$—C(O)—$H_2N$—X-MAL has a polymer purity of greater than about 80%.

Examples 1 and 5 illustrate a method of forming a reactive polymer of the invention using a linker that comprises a terminal maleimide group. In Example 1, a polymer segment modified to contain a reactive amino group is reacted with bifunctional linker comprising an activated ester and a maleimide group. A similar approach is utilized in Example 5 to prepare a polymer maleimide having a cyclohexylene containing linker. Examples 2, 3, and 4 demonstrate formation of a polymer amine intermediate that is then converted to the corresponding maleimide. Examples 9, 10, 11, and 12 demonstrate the synthesis of cycloalkylene-containing linkers by method 2 above, where a reactive polymer starting material, POLY-$[O]_b$—C(O)-LG, is reacted with a diamine reagent to form POLY-$[O]_b$—C(O)—$H_2N$—X—$NH_2$, which is then converted to the corresponding maleimide-terminated product.

Storage of Polymer Maleimide Reagents

Preferably, the polymer maleimides of the invention, as well as their amino counterparts, are stored under an inert atmosphere, such as under argon or under nitrogen. Due to the potential of the maleimide portion of the molecule for reaction with water (e.g., by exposure to moisture to form the corresponding ring-opened form), it is also preferable to minimize exposure of the polymer maleimides of the invention to moisture. Thus, preferred storage conditions are under dry argon or another dry inert gas at temperatures below about −15° C. Storage under low temperature conditions is preferred, since rates of undesirable side reactions, such as maleimide ring opening, are slowed at lower temperatures. In instances where the polymer segment of the polymer product is PEG, the PEG portion can react slowly with oxygen to form peroxides along the PEG portion of the molecule. Formation of peroxides can ultimately lead to chain cleavage, thus increasing the polydispersity of the PEG reagents provided herein. In view of the above, it is additionally preferred to store the PEG maleimides and related polymers of the invention in the dark.

Biologically Active Conjugates

Coupling Chemistry, Separation, Storage

The Conjugates

The present invention also encompasses conjugates formed by reaction of any of the herein described stabilized polymer maleimides or their corresponding polymer amine counterparts. In particular, the herein-described polymer maleimides are useful for conjugation to active agents or surfaces bearing at least one thiol or amino group available for reaction, while the herein-described polymer amines are useful for conjugation to active agents or surfaces bearing at least one carboxylic group available for reaction.

For instance, a conjugate of the invention may possess the following structure:

XV

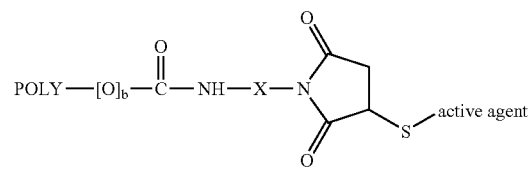

where "—S-active agent" represents an active agent, preferably a biologically active agent, comprising a thiol (—SH)

group, and the other variables are as described previously. In instances where the active agent is a biologically active agent or small molecule containing only one reactive thiol group, the resulting composition may advantageously contain only a single polymer conjugate species, due to the relatively low number of sulfhydryl groups typically contained within a protein and accessible for conjugation. In some instances, a protein or small molecule or other active agent is engineered to possess a thiol group in a known position, and will similarly result in a composition comprising only a single polymer conjugate species.

Alternatively, a conjugate of the invention may possess the following structure:

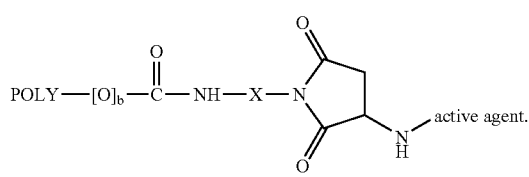

XVI

In structure XVI, "—NH-active agent" represents an active agent or surface comprising an amino group, preferably a biologically active agent, and the other variables are as previously described.

The polymer amines of the invention, when used directly, can be used to provide conjugates of the following type:

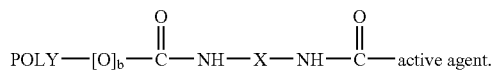

The polymer conjugates provided herein, particularly those derived from the stabilized polymer maleimides of the invention, similarly possess the feature of improved hydrolytic stability to maleimide ring opening. This feature is demonstrated in Example VIII. The synthesis of exemplary conjugates, using both the model compound, 2-mercaptoethanol, and an illustrative protein, is described in Examples 6, 14, 15, 16, and 17.

Methods of Conjugation

Suitable conjugation conditions are those conditions of time, temperature, pH, reagent concentration, solvent, and the like sufficient to effect conjugation between a polymeric reagent and an active agent. As is known in the art, the specific conditions depend upon, among other things, the active agent, the type of conjugation desired, the presence of other materials in the reaction mixture and so forth. Sufficient conditions for effecting conjugation in any particular case can be determined by one of ordinary skill in the art upon a reading of the disclosure herein, reference to the relevant literature, and/or through routine experimentation.

Exemplary conjugation conditions include carrying out the conjugation reaction at a pH of from about 6 to about 10, and at, for example, a pH of about 6.0, 6.5, 7.0, 7.5, 8.0, 8.5, 9.0, 9.5, or 10. The reaction is allowed to proceed from about 5 minutes to about 72 hours, preferably from about 30 minutes to about 48 hours, and more preferably from about 4 hours to about 24 hours or less. Temperatures for conjugation reactions are typically, although not necessarily, in the range of from about 0° C. to about 40° C.; conjugation is often carried out at room temperature or less. Conjugation reactions are often carried out in a buffer such as a phosphate or acetate buffer or similar system.

With respect to reagent concentration, an excess of the polymeric reagent is typically combined with the active agent. In some cases, however, it is preferred to have stoichiometic amounts of the number of reactive groups on the polymeric reagent to the amount of active agent. Exemplary ratios of polymeric reagent to active agent include molar ratios of about 1:1 (polymeric reagent:active agent), 1.5:1, 2:1, 3:1, 4:1, 5:1, 6:1, 8:1, or 10:1. The conjugation reaction is allowed to proceed until substantially no further conjugation occurs, which can generally be determined by monitoring the progress of the reaction over time.

Progress of the reaction can be monitored by withdrawing aliquots from the reaction mixture at various time points and analyzing the reaction mixture by SDS-PAGE or MALDI-TOF mass spectrometry or any other suitable analytical method. Once a plateau is reached with respect to the amount of conjugate formed or the amount of unconjugated polymer remaining, the reaction is assumed to be complete. Typically, the conjugation reaction takes anywhere from minutes to several hours (e.g., from 5 minutes to 24 hours or more). The resulting product mixture is preferably, but not necessarily purified, to separate out excess reagents, unconjugated reactants (e.g., active agent) undesired multi-conjugated species, and free or unreacted polymer. The resulting conjugates can then be further characterized using analytical methods such as MALDI, capillary electrophoresis, gel electrophoresis, and/or chromatography.

More preferably, a polymer maleimide of the invention is typically conjugated to a sulfhydryl-containing active agent at pHs ranging from about 6-9 (e.g., at 6, 6.5, 7, 7.5, 8, 8.5, or 9), more preferably at pHs from about 7-9, and even more preferably at pHs from about 7 to 8. Generally, a slight molar excess of polymer maleimide is employed, for example, a 1.5 to 15-fold molar excess, preferably a 2-fold to 10 fold molar excess. Reaction times generally range from about 15 minutes to several hours, e.g., 8 or more hours, at room temperature. For sterically hindered sulfhydryl groups, required reaction times may be significantly longer. The stabilized maleimides of the invention are thiol-selective, and thiol-selective conjugation is preferably conducted at pHs around 7.

Reactions with amino groups proceed at higher pHs, but are relatively slow. Protein PEGylation reaction conditions vary depending on the protein, the desired degree of PEGylation, and the particular polymer maleimide reagent.

Illustrative Reaction Scheme

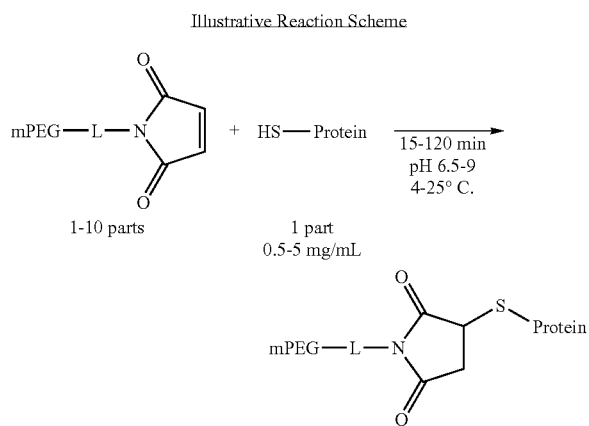

Separation

Optionally, conjugates produced by reacting a PEG maleimide or PEG amine of the invention with a biologically active agent are purified to obtain/isolate different PEGylated species. Alternatively, and more preferably for lower molecular weight PEGs, e.g., having molecular weights less than about 20 kilodaltons, preferably less than or equal to about 10 kilodaltons, a product mixture can be purified to obtain a distribution around a certain number of PEGs per protein molecule, where applicable. For example, a product mixture can be purified to obtain an average of anywhere from one to five PEGs per protein, typically an average of about 3 PEGs per protein. The strategy for purification of the final conjugate reaction mixture will depend upon a number of factors—the molecular weight of the polymer employed, the particular protein, the desired dosing regimen, and the residual activity and in vivo properties of the individual conjugate(s) species.

If desired, PEG conjugates having different molecular weights can be isolated using gel filtration chromatography. While this approach can be used to separate PEG conjugates having different molecular weights, this approach is generally ineffective for separating positional isomers having different pegylation sites within a protein. For example, gel filtration chromatography can be used to separate from each other mixtures of PEG 1-mers, 2-mers, 3-mers, etc., although each of the recovered PEG-mer compositions may contain PEGs attached to different reactive amino groups (e.g., lysine residues) within the protein.

Gel filtration columns suitable for carrying out this type of separation include Superdex™ and Sephadex™ columns available from Amersham Biosciences. Selection of a particular column will depend upon the desired fractionation range desired. Elution is generally carried out using a non-amine based buffer, such as phosphate, acetate, or the like. The collected fractions may be analysed by a number of different methods, for example, (i) OD at 280 nm for protein content, (ii) BSA protein analysis, (iii) iodine testing for PEG content (Sims G. E. C., et al., *Anal. Biochem*, 107, 60-63, 1980), or alternatively, (iv) by running an SDS PAGE gel, followed by staining with barium iodide.

Separation of positional isomers is carried out by reverse phase chromatography using an RP-HPLC C18 column (Amersham Biosciences or Vydac) or by ion exchange chromatography using an ion exchange column, e.g., a Sepharose™ ion exchange column available from Amersham Biosciences. Either approach can be used to separate PEG-biomolecule isomers having the same molecular weight (positional isomers).

Depending upon the intended use for the resulting PEG-conjugates, following conjugation, and optionally additional separation steps, the conjugate mixture may be concentrated, sterile filtered, and stored at low temperatures from about $-20°$ C. to about $-80°$ C. Alternatively, the conjugate may be lyophilized, either with or without residual buffer and stored as a lyophilized powder. In some instances, it is preferable to exchange a buffer used for conjugation, such as sodium acetate, for a volatile buffer such as ammonium carbonate or ammonium acetate, that can be readily removed during lyophilization, so that the lyophilized protein conjugate powder formulation is absent residual buffer. Alternatively, a buffer exchange step may be used using a formulation buffer, so that the lyophilized conjugate is in a form suitable for reconstitution into a formulation buffer and ultimately for administration to a mammal.

Target Molecules and Surfaces

The stabilized polymer maleimides (amines) of the invention may be attached, either covalently or non-covalently, to a number of entities including films, chemical separation and purification surfaces, solid supports, metal/metal oxide surfaces such as gold, titanium, tantalum, niobium, aluminum, steel, and their oxides, silicon oxide, macromolecules, and small molecules. Additionally, the polymers of the invention may also be used in biochemical sensors, bioelectronic switches, and gates. The polymer maleimides (amines) of the invention may also be employed as carriers for peptide synthesis, for the preparation of polymer-coated surfaces and polymer grafts, to prepare polymer-ligand conjugates for affinity partitioning, to prepare cross-linked or non-cross-linked hydrogels, and to prepare polymer-cofactor adducts for bioreactors.

A biologically active agent for use in coupling to a polymer of the invention may be any one or more of the following. Suitable agents may be selected from, for example, hypnotics and sedatives, psychic energizers, tranquilizers, respiratory drugs, anticonvulsants, muscle relaxants, antiparkinson agents (dopamine antagonists), analgesics, anti-inflammatories, antianxiety drugs (anxiolytics), appetite suppressants, antimigraine agents, muscle contractants, anti-infectives (antibiotics, antivirals, antifungals, vaccines) antiarthritics, antimalarials, antiemetics, anepileptics, bronchodilators, cytokines, growth factors, anti-cancer agents, antithrombotic agents, antihypertensives, cardiovascular drugs, antiarrhythmics, antioxicants, anti-asthma agents, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents.

More particularly, the active agent may fall into one of a number of structural classes, including but not limited to small molecules (preferably insoluble small molecules), peptides, polypeptides, proteins, antibodies, polysaccharides, steroids, nucleotides, oligonucleotides, polynucleotides, fats, electrolytes, and the like. Preferably, an active agent for coupling to a polymer maleimide of the invention possesses a native amino or a sulfydryl group, or alternatively, is modified to contain at least one reactive amino or sulfhydryl group suitable for coupling to a polymer maleimide of the invention.

Specific examples of active agents suitable for covalent attachment to a polymer of the invention include but are not limited to aspariginase, amdoxovir (DAPD), antide, becaplermin, calcitonins, cyanovirin, denileukin diftitox, erythropoietin (EPO), EPO agonists (e.g., peptides from about 10-40 amino acids in length and comprising a particular core sequence as described in WO 96/40749), dornase alpha, erythropoiesis stimulating protein (NESP), coagulation factors such as Factor V, Factor VII, Factor VIIa, Factor VIII, Factor IX, Factor X, Factor XII, Factor XIII, von Willebrand factor; ceredase, cerezyme, alpha-glucosidase, collagen, cyclosporin, alpha defensins, beta defensins, exedin-4, granulocyte colony stimulating factor (GCSF), thrombopoietin (TPO), alpha-1 proteinase inhibitor, elcatonin, granulocyte macrophage colony stimulating factor (GMCSF), fibrinogen, filgrastim, growth hormones human growth hormone (hGH), growth hormone releasing hormone (GHRH), GRO-beta, GRO-beta antibody, bone morphogenic proteins such as bone morphogenic protein-2, bone morphogenic protein-6, OP-1; acidic fibroblast growth factor, basic fibroblast growth factor, CD-40 ligand, heparin, human serum albumin, low molecular weight heparin (LMWH), interferons such as interferon alpha, interferon beta, interferon gamma, interferon omega, interferon tau, consensus interferon; interleukins and interleukin receptors such as interleukin-1 receptor, interluekin-2, interluekin-2 fusion proteins, interleukin-1 receptor antagonist, interleukin-3, interleukin-4, interleukin-4 receptor, interleukin-6, interleukin-8, interleukin-12, interleukin-13 receptor, interleukin-17 receptor; lactoferrin and lactoferrin fragments, luteinizing hormone releasing hormone (LHRH), insulin, pro-insulin, insulin analogues (e.g., mono-acylated insulin as described in U.S. Pat. No. 5,922,675), amylin, C-peptide, somatostatin, somatostatin analogs including octreotide, vasopressin, follicle stimulating hormone (FSH), influenza vaccine, insulin-like growth factor (IGF), insulintropin, macrophage colony stimulating factor (M-CSF), plasminogen activators such as alteplase, urokinase, reteplase, streptokinase, pamiteplase, lanoteplase, and teneteplase; nerve growth factor (NGF), osteoprotegerin, platelet-derived growth factor, tissue growth factors, transforming growth factor-1, vascular endothelial growth factor, leukemia inhibiting factor, keratinocyte growth factor (KGF), glial growth factor (GGF), T Cell receptors, CD molecules/antigens, tumor necrosis factor (TNF), monocyte chemoattractant protein-1, endothelial growth factors, parathyroid hormone (PTH), glucagon-like peptide, somatotropin, thymosin alpha 1, thymosin alpha 1 IIb/IIIa inhibitor, thymosin beta 10, thymosin beta 9, thymosin beta 4, alpha-1 antitrypsin, phosphodiesterase (PDE) compounds, VLA-4 (very late antigen-4), VLA-4 inhibitors, bisphosponates, respiratory syncytial virus antibody, cystic fibrosis transmembrane regulator (CFTR) gene, deoxyreibonuclease (Dnase), bactericidal/permeability increasing protein (BPI), and anti-CMV antibody. Exemplary monoclonal antibodies include etanercept (a dimeric fusion protein consisting of the extracellular ligand-binding portion of the human 75 kD TNF receptor linked to the Fc portion of IgG1), abciximab, afeliomomab, basiliximab, daclizumab, infliximab, ibritumomab tiuexetan, mitumomab, muromonab-CD3, iodine 131 tositumomab conjugate, olizumab, rituximab, and trastuzumab (herceptin).

Additional agents suitable for covalent attachment to a polymer of the invention include but are not limited to amifostine, amiodarone, aminocaproic acid, aminohippurate sodium, aminoglutethimide, aminolevulinic acid, aminosalicylic acid, amsacrine, anagrelide, anastrozole, asparaginase, anthracyclines, bexarotene, bicalutamide, bleomycin, buserelin, busulfan, cabergoline, capecitabine, carboplatin, carmustine, chlorambucin, cilastatin sodium, cisplatin, cladribine, clodronate, cyclophosphamide, cyproterone, cytarabine, camptothecins, 13-cis retinoic acid, all trans retinoic acid; dacarbazine, dactinomycin, daunorubicin, deferoxamine, dexamethasone, diclofenac, diethylstilbestrol, docetaxel, doxorubicin, epirubicin, estramustine, etoposide, exemestane, fexofenadine, fludarabine, fludrocortisone, fluorouracil, fluoxymesterone, flutamide, gemcitabine, epinephrine, L-Dopa, hydroxyurea, idarubicin, ifosfamide, imatinib, irinotecan, itraconazole, goserelin, letrozole, leucovorin, levamisole, lisinopril, lovothyroxine sodium, lomustine, mechlorethamine, medroxyprogesterone, megestrol, melphalan, mercaptopurine, metaraminol bitartrate, methotrexate, metoclopramide, mexiletine, mitomycin, mitotane, mitoxantrone, naloxone, nicotine, nilutamide, octreotide, oxaliplatin, pamidronate, pentostatin, pilcamycin, porfimer, prednisone, procarbazine, prochlorperazine, ondansetron, raltitrexed, sirolimus, streptozocin, tacrolimus, tamoxifen, temozolomide, teniposide, testosterone, tetrahydrocannabinol, thalidomide, thioguanine, thiotepa, topotecan, tretinoin, valrubicin, vinblastine, vincristine, vindesine, vinorelbine, dolasetron, granisetron; formoterol, fluticasone, leuprolide, midazolam, alprazolam, amphotericin B, podophylotoxins, nucleoside antivirals, aroyl hydrazones, sumatriptan; macrolides such as erythromycin, oleandomycin, troleandomycin, roxithromycin, clarithromycin, davercin, azithromycin, flurithromycin, dirithromycin, josamycin, spiromycin, midecamycin, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin; aminoglycosides such as gentamicin, netilmicin, paramecin, tobramycin, amikacin, kanamycin, neomycin, and streptomycin, vancomycin, teicoplanin, rampolanin, mideplanin, colistin, daptomycin, gramicidin, colistimethate; polymixins such as polymixin B, capreomycin, bacitracin, penems; penicillins including penicllinase-sensitive agents like penicillin G, penicillin V; penicllinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefinetazole, ceftazidime, loracarbef, and moxalactam, monobactams like aztreonam; and carbapenems such as imipenem, meropenem, pentamidine isethiouate, albuterol sulfate, lidocaine, metaproterenol sulfate, beclomethasone diprepionate, triamcinolone acetamide, budesonide acetonide, fluticasone, ipratropium bromide, flunisolide, cromolyn sodium, and ergotamine tartrate; taxanes such as paclitaxel; SN-38, and tyrphostines.

Preferred peptides or proteins for coupling to a polymer maleimide of the invention include EPO, IFN-α, IFN-β, IFN-γ, consensus IFN, Factor VII, Factor VIII, Factor IX, IL-2, remicade (infliximab), Rituxan (rituximab), Enbrel (etanercept), Synagis (palivizumab), Reopro (abciximab), Herceptin (trastuzimab), tPA, Cerizyme (imiglucerase), Hepatitus-B vaccine, rDNAse, alpha-1 proteinase inhibitor, GCSF, GMCSF, hGH, insulin, FSH, and PTH.

The above exemplary biologically active agents are meant to encompass, where applicable, analogues, agonists, antagonists, inhibitors, isomers, and pharmaceutically acceptable salt forms thereof. In reference to peptides and proteins, the invention is intended to encompass synthetic, recombinant, native, glycosylated, and non-glycosylated forms, as well as biologically active fragments thereof. The above biologically active proteins are additionally meant to encompass variants having one or more amino acids substituted (e.g., cysteine), deleted, or the like, as long as the resulting variant protein possesses at least a certain degree of activity of the parent (native) protein.

Pharmaceutical Compositions

The present invention also includes pharmaceutical preparations comprising a conjugate as provided herein in combination with a pharmaceutical excipient. Generally, the conjugate itself will be in a solid form (e.g., a precipitate), which can be combined with a suitable pharmaceutical excipient that can be in either solid or liquid form.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The preparation may also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the preparation as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant may be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; and chelating agents, such as EDTA, zinc and other such suitable cations.

Acids or bases may be present as an excipient in the preparation. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The pharmaceutical preparations encompass all types of formulations and in particular those that are suited for injection, e.g., powders that can be reconstituted as well as suspensions and solutions. The amount of the conjugate (i.e., the conjugate formed between the active agent and the polymer described herein) in the composition will vary depending on a number of factors, but will optimally be a therapeutically effective dose when the composition is stored in a unit dose container (e.g., a vial). In addition, the pharmaceutical preparation can be housed in a syringe. A therapeutically effective dose can be determined experimentally by repeated administration of increasing amounts of the conjugate in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, preferably from about 5%-98% by weight, more preferably from about 15-95% by weight of the excipient, with concentrations less than 30% by weight most preferred.

These foregoing pharmaceutical excipients along with other excipients are described in "Remington: The Science & Practice of Pharmacy", $19^{th}$ ed., Williams & Williams, (1995), the "Physician's Desk Reference", $52^{nd}$ ed., Medical Economics, Montvale, N.J. (1998), and Kibbe, A. H., Handbook of Pharmaceutical Excipients, $3^{rd}$ Edition, American Pharmaceutical Association, Washington, D.C., 2000.

The pharmaceutical preparations of the present invention are typically, although not necessarily, administered via injection and are therefore generally liquid solutions or suspensions immediately prior to administration. The pharmaceutical preparation can also take other forms such as syrups, creams, ointments, tablets, powders, and the like. Other modes of administration are also included, such as pulmonary, rectal, transdermal, transmucosal, oral, intrathecal, subcutaneous, intra-arterial, and so forth.

As previously described, the conjugates can be administered injected parenterally by intravenous injection, or less preferably by intramuscular or by subcutaneous injection. Suitable formulation types for parenteral administration include ready-for-injection solutions, dry powders for combination with a solvent prior to use, suspensions ready for injection, dry insoluble compositions for combination with a vehicle prior to use, and emulsions and liquid concentrates for dilution prior to administration, among others.

Methods of Administering

The invention also provides a method for administering a conjugate as provided herein to a patient suffering from a condition that is responsive to treatment with conjugate. The method comprises administering, generally via injection, a therapeutically effective amount of the conjugate (preferably provided as part of a pharmaceutical preparation). The method of administering may be used to treat any condition that can be remedied or prevented by administration of the particular conjugate. Those of ordinary skill in the art appreciate which conditions a specific conjugate can effectively treat. The actual dose to be administered will vary depend upon the age, weight, and general condition of the subject as well as the severity of the condition being treated, the judgment of the health care professional, and conjugate being administered. Therapeutically effective amounts are known to those skilled in the art and/or are described in the pertinent reference texts and literature. Generally, a therapeutically effective amount will range from about 0.001 mg to 100 mg, preferably in doses from 0.01 mg/day to 75 mg/day, and more preferably in doses from 0.10 mg/day to 50 mg/day.

The unit dosage of any given conjugate (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted.

One advantage of administering the conjugates of the present invention is that individual water-soluble polymer portions can be cleaved off. Such a result is advantageous when clearance from the body is potentially a problem because of the polymer size. Optimally, cleavage of each water-soluble polymer portion is facilitated through the use of physiologically cleavable and/or enzymatically degradable linkages such as urethane, amide, carbonate or ester-containing linkages. In this way, clearance of the conjugate (via cleavage of individual water-soluble polymer portions) can be modulated by selecting the polymer molecular size and the type functional group that would provide the desired clearance properties. One of ordinary skill in the art can determine the proper molecular size of the polymer as well as the cleavable functional group. For example, one of ordinary skill in the art, using routine experimentation, can determine a proper molecular size and cleavable functional group by first preparing a variety of polymer derivatives with different polymer weights and cleavable functional groups, and then obtaining the clearance profile (e.g., through periodic blood or urine sampling) by administering the polymer derivative to a patient and taking periodic blood and/or urine sampling. Once a series of clearance profiles have been obtained for each tested conjugate, a suitable conjugate can be identified.

All articles, books, patents, patent publications and other publications referenced herein are incorporated by reference in their entireties.

EXAMPLES

It is to be understood that while the invention has been described in conjunction with certain preferred specific embodiments thereof, the foregoing description as well as the examples that follow are intended to illustrate and not limit the scope of the invention. Other aspects, advantages and modifications within the scope of the invention will be apparent to those skilled in the art to which the invention pertains.

Abbreviation.
DCM: dichloromethane
NMR: nuclear magnetic resonance
DI: deionized
r.t. room temperature
anh. Anhydrous
Da Daltons
GPC gel permeation chromatography Materials and Methods.

All chemical reagents referred to in the appended examples are commercially available unless otherwise indicated.

All PEG reagents referred to in the appended examples are available from Nektar, Huntsville, Ala. All $^1$HNMR data was generated by a 300 or 400 MHz NMR spectrometer manufactured by Bruker.

Example 1

Branched PEG2-amidopentamethylene-maleimide (40 kDa) (L1-AMPE)

Overview of Synthesis:

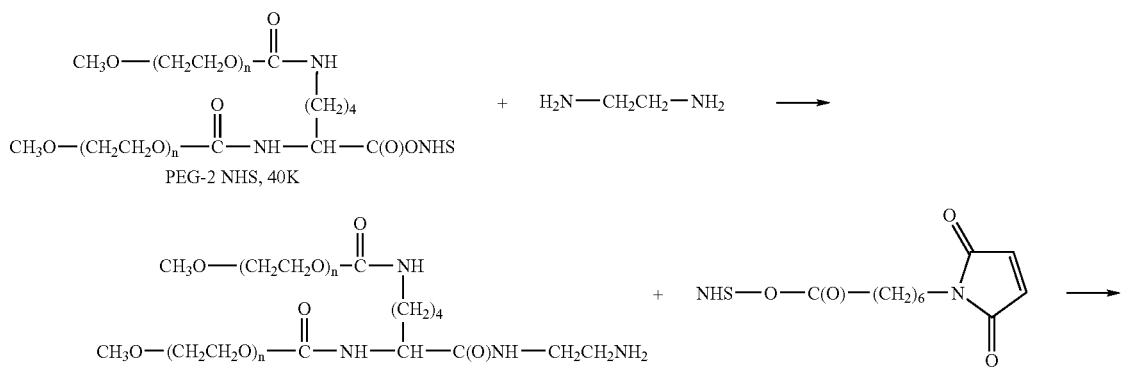

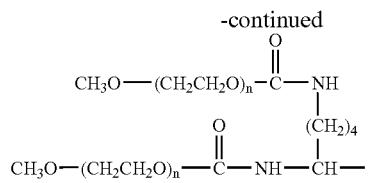

A. Branched PEG2(40K)Amine

To a solution of branched PEG2(40,000)-N-hydroxysuccinimide ester (20 g, 0.00050 moles) (Nektar, Huntsville Ala.) in methylene chloride (250 ml), ethylenediamine (0.68 ml, 0.01017 moles) was added and the reaction mixture was stirred overnight at room temperature under argon atmosphere. Next the solvent was evaporated to dryness. The crude product was dissolved in small amount of methylene chloride and precipitated with isopropyl alcohol. The wet product was dried under reduced pressure. Yield 17.2 g.

NMR ($d_6$-DMSO): 2.65 ppm (t, —$\underline{CH_2}$—$NH_2$), 3.24 ppm (s, —$OCH_3$), 3.51 ppm (s, PEG backbone).

B. Branched PEG2-amidopentamethylene-maleimide-40 kDa

To a solution of N-succinimidyl(ε-maleimidohexanoate) (0.1 g, 0.000324 moles, Pierce Chemical Company), in methylene chloride (10 ml), was added over a period of 3 minutes a solution of branched PEG2 (40K) amine from Step A (12.2 g, 0.000305 moles) in methylene chloride (20 ml). Next, 0.045 ml of triethylamine was added and the mixture was stirred overnight at room temperature under an argon atmosphere. The solvent was then distilled and the crude product that remained was dissolved in 30 ml of methylene chloride and then precipitated by the addition of 450 ml of isopropyl alcohol at room temperature. The yield was 11.5 g.

Proton NMR analysis indicated main signals at: 3.24 ppm (s, —$OCH_3$), 3.51 ppm (s, PEG backbone), 7.01 ppm (s, CH═CH, maleimide), which are indicative of the correct product. On the basis of the NMR, the substitution was estimated to be approximately 89%. GPC analysis revealed the main product to be 98.3% desired compound, with 1.7% dimer. The product also possessed required ultraviolet absorption.

Example 2 mPEG(5,000 Da)-butylmalemide (L3-TEME)

Overview of Synthesis:

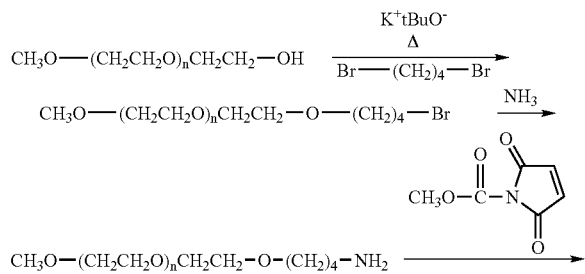

-continued

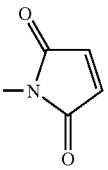

A. mPEG(5,000 Da)-butylamine

A solution of mPEG-5,000 Da (2.0 g, 0.0004 moles) (NOF Corporation) in toluene (30 ml) was azeotropically dried by distilling off 15 ml toluene. 1.0 M solution of potassium tert-butoxide in tert-butanol (2.0 ml, 0.002 moles) and 1,4-dibromobutane (0.43 g, 0.002 moles) were added and the mixture was stirred overnight at 75° C. under argon atmosphere. The mixture was filtered and the solvents were distilled off under reduced pressure. The residue was dissolved in dichloromethane (3 ml) and isopropyl alcohol (50 ml) was added. The precipitated product was filtered off and dried under reduced pressure. Next it was dissolved in concentrated ammonia (20 ml) and the resulting solution was stirred 20 h at room temperature. The product was extracted with dichloromethane. The extract was dried with anhydrous magnesium sulfate and the solvent was distilled off under reduced pressure giving 1.5 g of M-PEG(5,000)-butylamine.

NMR ($D_2O$): 1.53 ppm (m, —$\underline{CH_2}$—$\underline{CH_2}$—$\underline{CH_2}$—$NH_2$) 2.75 ppm (t, —$\underline{CH_2}$—$NH_2$), 3.27 ppm (s, —$OCH_3$), 3.53 ppm (s, PEG backbone).

B. mPEG(5000 Da)-butylmaleimide mPEG(5,000)-butylamine (1.0 g, 0.0002 moles) from Step A was dissolved in saturated aqueous $NaHCO_3$ (5 ml) and the mixture was cooled to ° C. N-methoxycarbonylmaleimide (0.25 g) was added with vigorous stirring. After stirring for 15 minutes, water (8 ml) was added and the mixture was stirred an additional 65 minutes. NaCl (0.5 g) was added and the pH was adjusted to 3.0 with 10% phosphoric acid. The product was extracted with dichloromethane. The extract was dried with anhydrous $MgSO_4$ and the solvent was distilled off under reduced pressure giving 0.9 g of white, solid product.

NMR ($d_6$-DMSO): 1.48 ppm (bm, —$CH_2$—$\underline{CH_2}$—$CH_2$-Mal), 3.24 ppm (s, —$OCH_3$), 3.51 ppm (s, PEG backbone), 7.00 ppm (s, —CH═CH—).

The product had 82% substitution of the maleimidyl group on the PEG moiety.

Example 3 mPEG(5000 Da)-hexylmaleimide (L3-HEXA)

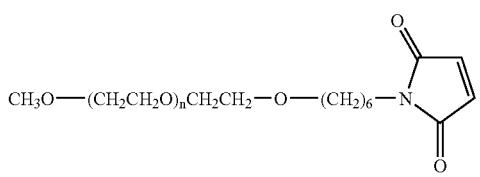

This synthesis is essentially equivalent to that described in Example 2 above, with the exception that the dibromo-reagent utilized possesses two additional methylenes, i.e., Br—$(CH_2)_6$—Br.

A. mPEG(20,000 Da)-hexylamine

A solution of mPEG-5,000 Da (2.0 g, 0.0004 moles) (NOF Corporation) in toluene (30 ml) was azeotropically dried by distilling off 15 ml toluene. 1.0M solution of potassium tert-butoxide in tert-butanol (2.0 ml, 0.002 moles) and 1,6-dibromohexane (0.49 g, 0.002 moles) were added and the mixture was stirred overnight at 80° C. under argon atmosphere. The mixture was filtered and the solvents were distilled off under reduced pressure. The residue was dissolved in dichloromethane (3 ml) and isopropyl alcohol (50 ml) was added. The precipitated product was filtered off and dried under reduced pressure. Next it was dissolved in concentrated ammonia (20 ml) and the resulting solution was stirred 20 h at room temperature. The product was extracted with dichloromethane. The extract was dried with anhydrous magnesium sulfate and the solvent was distilled off under reduced pressure giving 1.6 g of M-PEG(5,000)-hexylamine.

NMR (D$_2$O): 1.28 ppm (m, —CH$_2$—CH$_2$—CH$_2$—CH$_2$—NH$_2$), 1.47 ppm (m, —CH$_2$—CH$_2$—CH$_2$—CH$_2$—NH$_2$), 2.71 ppm (t, —CH$_2$—NH$_2$), 3.27 ppm (s, —OCH$_3$), 3.53 ppm (s, PEG backbone).

B. mPEG(5000 Da)-hexylmaleimide mPEG(5,000 Da)-hexylamine (1.0 g, 0.0002 moles) from Step A was dissolved in saturated aqueous NaHCO$_3$ (5 ml) and the mixture was cooled to ° C. N-methoxycarbonylmaleimide (0.25 g) was added with vigorous stirring. After stirring for 15 minutes, water (8 ml) was added and the mixture was stirred an additional 65 minutes. NaCl (0.5 g) was added and the pH was adjusted to 3.0 with 10% phosphoric acid. The product was extracted with dichloromethane. The extract was dried with anhydrous MgSO$_4$ and the solvent was distilled off under reduced pressure giving 0.9 g of white, solid product.

NMR (d$_6$-DMSO): 1.24 ppm (bm, —CH$_2$—CH$_2$—CH$_2$—CH$_2$-Mal), 1.45 ppm (bm, —CH$_2$—CH$_2$—CH$_2$—CH$_2$—CH$_2$-Mal), 3.24 ppm (s, —OCH$_3$), 3.51 ppm (s, PEG backbone), 7.01 ppm (s, —CH=CH—).

The product had 80% substitution of the maleimidyl group on the PEG moiety.

Example 4 mPEG (5K Da)-propylmaleimide (L3-TME)

Overview of Synthesis:

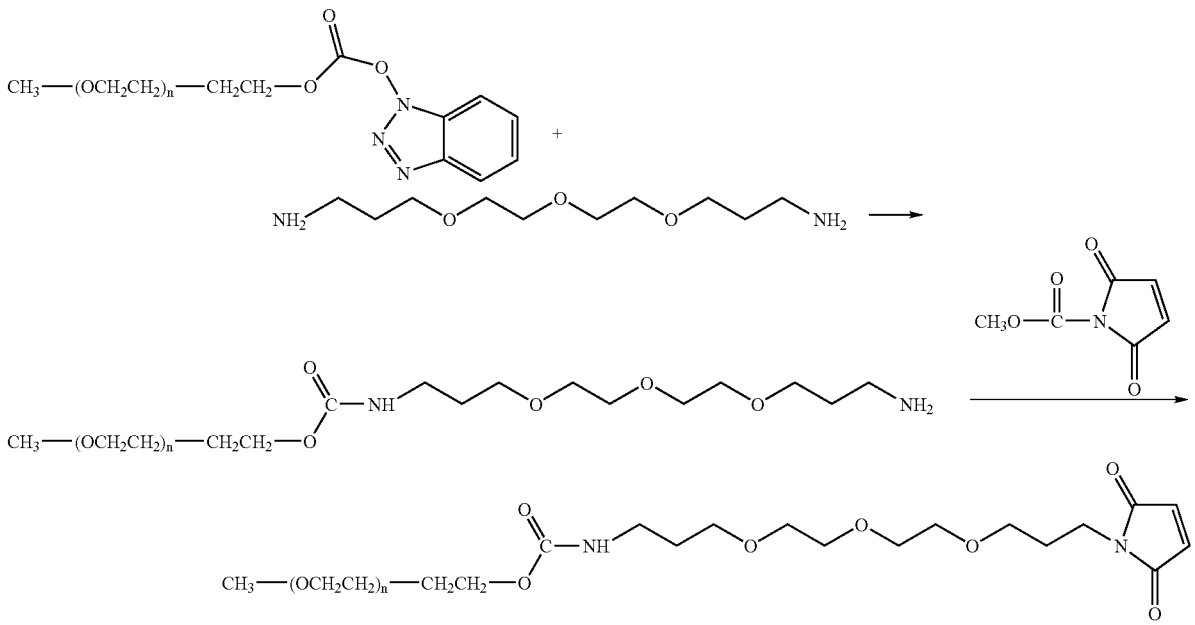

A. mPEG (5K Da)-Propylamine

To a solution of 4,7,10-trioxa-1,13-tridecanediamine (4.2 g) in anh. acetonitrile (100 ml) was added mPEG-benzotriazolylcarbonate (5 g) (Shearwater Corp.) in anh. acetonitrile (60 ml) during 20 min and the mixture was stirred overnight at room temperature under argon atmosphere. Next the solvent was distilled off. The product was dissolved in 100 ml DI H$_2$O. NaCl (5 g) was added and the pH was adjusted to 3.0 with 10% H$_3$PO$_4$. The product was extracted with CH$_2$Cl$_2$.

The extract was washed with 50 ml 2% KOH solution, then it was dried (MgSO$_4$) and the solvent was distilled off. Next the product was dissolved in 10 ml CH$_2$Cl$_2$ and reverse precipitated with 200 ml isopropyl alcohol at 0-5° C. Yield after drying 4.2 g.

NMR: Desired product, substitution 85.0%, GPC (buffer, 25° C.) substitution 97.02%.

B. mPEG (5K Da)-PA-Maleimide mPEG (5K Da)-propylamine (4.0 g in 20 ml deionized water, pH of 8.93) from Step A was cooled to 0-5° C. on an ice bath and a solution of N-methoxycarbonylmaleimide (0.5 g in 3.5 ml of anh. acetonitrile) was added and the mixture was stirred 15 min at 0-5° C. The ice bath was removed and DI H$_2$O (16 ml) was added and the mixture was stirred 45 min at room temperature. NaCl (2 g) was added and the pH of the mixture was adjusted to 3.0 with 10% H$_3$PO$_4$. The product was extracted with CH$_2$Cl$_2$. The extract was dried with MgSO$_4$ and the solvent was distilled off. The crude product was dissolved in CH$_2$Cl$_2$ (10 ml) and precipitated with isopropyl alcohol (200 ml) at 0-5° C. Yield 3.7 g.

NMR: Confirmed synthesis of desired product; substitution 83.5%.

Example 5 mPEG (5K Da)-amidocyclohexylmethyl-maleimide (L1-MCH)

Overview of Synthesis:

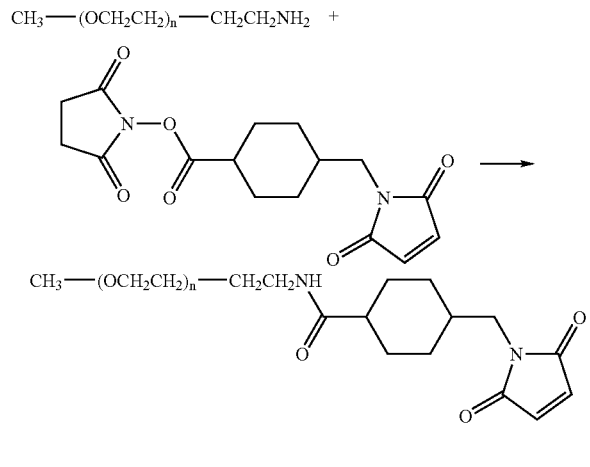

To a solution of 4-(maleimidomethyl)-1-cyclohexanecarboxylic acid, NHS ester (0.100 g) (Pierce Chemical Company) in CH$_2$Cl$_2$ (10 ml) was added a solution of mPEG (5K Da)-amine (1.5 g) (Shearwater Corp.) in CH$_2$Cl$_2$ (20 ml). TEA (0.042 ml) was added and the mixture was stirred overnight at room temperature under argon atmosphere. The solvent was distilled off. The crude product was dissolved in 2 ml CH$_2$Cl$_2$ and precipitated with isopropyl alcohol (60 ml) at 0-5° C. Yield 1.35 g.

NMR: Desired compound, substitution 79.7%. GPC (nitrate buffer, 25° C.): dimer: 3.98%; Main compound: 96.02%.

Example 6

Conjugate of mPEG (5K Da)-propylmaleimide (L3-TME)

To illustrate reaction of a reactive polymer of the invention with a molecule bearing a thiol group, to a solution of MPEG-PA-MAL from Example 4 (1.0 g) in phosphate buffer was added 25 μl of 2-mercaptoethanol. The mixture was stirred overnight at room temperature under argon atmosphere. The product was extracted with CH$_2$Cl$_2$ (3×20 ml). The extract was dried (MgSO4) and the solvent was distilled off. The crude product was dissolved in 2 ml CH$_2$Cl$_2$ and precipitated with 40 ml isopropyl alcohol at 0-5° C. Yield 0.78 g NMR: Formation of the desired product was confirmed by NMR; substitution: 64.9%

Example 7

Hydrolysis Rate Study of Reactive Polymers

Using HPLC analysis, the rate of hydrolytic degradation of the maleimide ring of several exemplary maleimide-terminated MPEG polymers (average molecular weight 5000 Da) was explored.

The following linkages between the maleimide and the PEG polymer segment were evaluated: amidoethylene (L1-AMDE), amidopentamethylene (L1-AMPE), amidocyclohexylmethyl (L1-MCH), oxybutyl (L3-TEME), oxyhexyl (L3-HEXA), oxyethyl (L3-ET), and oxypropyl (L3-TME). Complete structures are provided below for ease of reference.

TABLE 2

Hydrolysis Rates of mPEG (5 k-Da) Maleimides (5 mg/ml) in 50 mM Phosphate Buffer (pH~7.5) as Measured by UV Absorption at 297 nm mPEG-AMDE-MAL $CH_3-O(CH_2CH_2)_nCH_2CH_2-NH-\overset{O}{\underset{\|}{C}}-CH_2CH_2-N\begin{pmatrix}O\\O\end{pmatrix}$

TABLE 2-continued

Hydrolysis Rates of mPEG (5 k-Da) Maleimides (5 mg/ml) in 50 mM
Phosphate Buffer (pH~7.5) as Measured by UV Absorption at 297 nm

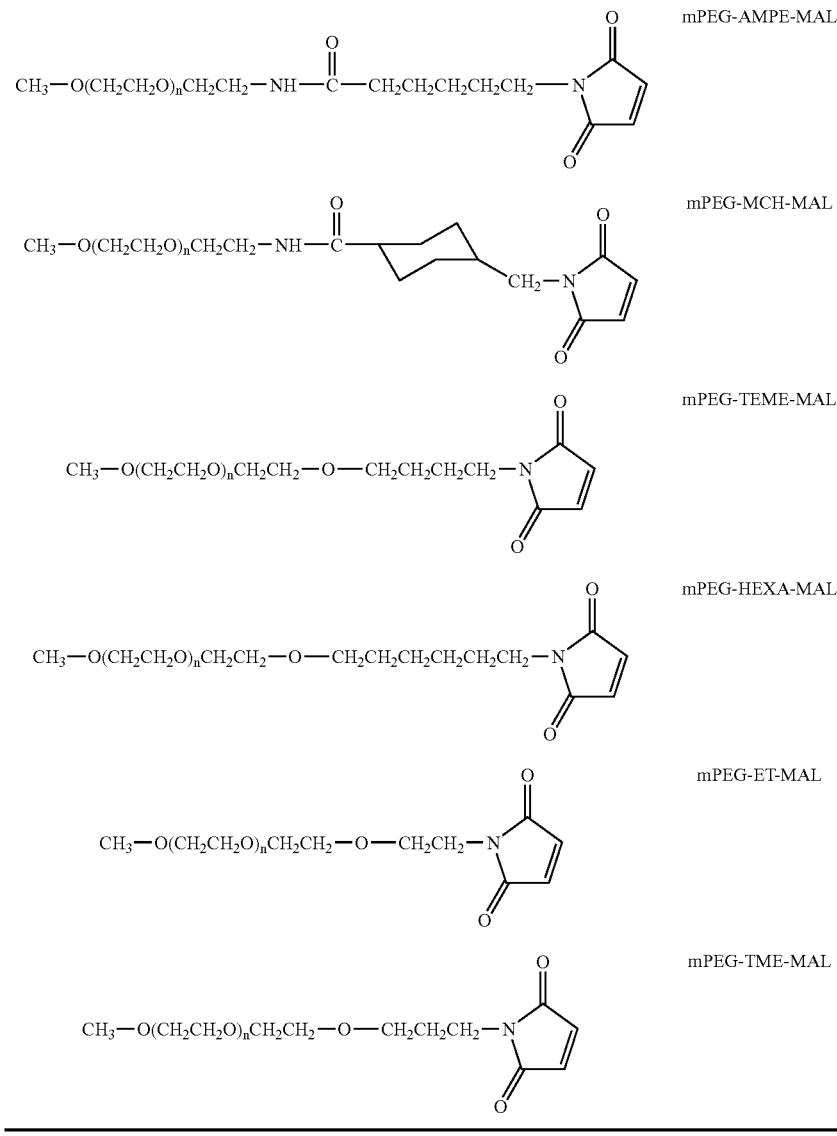

| Polymer | Structure (Table 1) | Half-life (hrs) | Relative Hydrolysis Rate |
| --- | --- | --- | --- |
| mPEG-AMDE-MAL | L1-AMDE | 8.8 | 3.66 |
| mPEG-AMPE-MAL | L1-AMPE | 19.4 | 1.66 |
| mPEG-MCH-MAL | L1-MCH | 16.3 | 1.98 |
| mPEG-TEME-MAL | L3-TEME | 19.6 | 1.65 |
| mPEG-HEXA-MAL | L3-HEXA | 32.3 | 1.00 |
| mPEG-ET-MAL | L3-ET | 8.1 | 4.01 |
| mPEG-TME-MAL | L3-TME | 11.5 | 2.82 |

As can be shown by the data in Table 2 above, the hydrolysis rates of these illustrative polymeric maleimides to form their respective maleamic acids varies with changes in the structure of the hydrocarbon portion adjacent to the maleimide ring. The data in column three demonstrates rates of hydrolysis relative to the hexamethylene-maleimide polymer. As can be seen, for the polymers examined, the L3-HEXA polymer was the most stable, that is to say, had the slowest hydrolysis rate, and thus, the longest half life. The data above indicates that an increase in the length of the hydrocarbon chain separating the polymer and the maleimide increases the half-life of the maleimide-terminated polymer itself.

Example 8

Hydrolysis Rate Study of Polymer Conjugates

The hydrolysis rates of representative protein and small molecule model conjugates were investigated to examine the correlation between the ring opening tendencies of the polymer-terminated maleimides themselves versus their conjugates.

Since large biomolecular components such as proteins have a dramatic effect on the retention of conjugated molecules on common liquid chromatography columns, it is generally more difficult to measure kinetics of maleimide conjugates than it is for the polymers themselves. In this analysis, the open acid form of the maleamic acid was not distinctly separable from the unopened or closed ring form. However, a combination analysis based upon size exclusion chromatography (HPLC-SE) and analytical protein electrophoresis (SDS-PAGE) was successfully employed to estimate the ring opening characteristics of polymeric maleimide protein conjugates, as well as conjugates prepared using model non-protein compounds.

In this study, two PEG-globular protein conjugates represented generally below were studied to examine their ring opening characteristics.

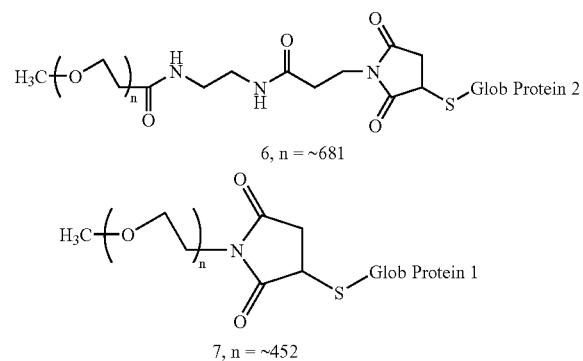

The top structure is a PEG-maleimide conjugate of Glob Protein 2, where Glob Protein 2 is a protein having a molecular weight of approximately 48 kDa. Glob Protein 2 was conjugated to a PEG maleimide derived from a PEG propionic acid, MW 30 kDa, which further included a medium-length linker interposed between the propionic acid derived portion of the polymer and the maleimide terminus. The linker in the top structure is —C(O)—NH(CH$_2$)$_2$—NH—C(O)—CH$_2$CH$_2$—.

The bottom structure is a PEG-maleimide conjugate of Glob Protein 1, where the protein possesses a molecular weight of about 11 kDa. The conjugate was prepared using a linkerless maleimide (mPEG-ET-MAL) having a molecular weight of about 20 kDa. The corresponding PEG maleimide structure is L3-ET, discussed in Example 7.

The bottom structure (Glob Protein 2) is completely ring opened after 24 hours at pH 8.5 at room temperature, thus indicating the instability of this type of maleimidyl terminated polymer absent a stabilizing linker separating the polymer and the maleimide ring. Relative to the linkerless form, however, the linker in the top structure (Glob Protein 1) retards the ring opening, since the ring structure in the top conjugate is not completely ring-opened until 17 hours, at pH 9, upon heating to 50° C. for 17 hours.

Similarly, hydrolysis rates of the stabilized polymer maleimides of the invention conjugated to a model compound, 2-mercaptoethanol, were determined to assess the tendency of the conjugates towards ring-opening. The study revealed that the present stabilized polymer maleimides are superior to those used to form conjugates of Glob Protein 1 and Glob Protein 2. That it to say, in both free and in conjugated form, the polymer maleimides of the invention exhibited superior stability and resistance against ring opening in comparison to linkerless PEG maleimide and, for example, the PEG-maleimide above, shown attached to Glob Protein 2.

Hydrolysis rate studies of conjugates of 8-TRI, 8-PEN, and 8-MCH (structures provided below in Table 3) were conducted as described above for the unconjugated maleimides. The half-lives shown were calculated from data taken at two different pH values. Similar to the unconjugated maleimides, the data indicate a slowing in reaction rate as the pHs drifted lower with increased ring opening. The linkage with the shortest hydrocarbon chain adjacent to the succinimide ring (i.e., 8-TRI) was the fastest to open in comparison to the other conjugates studied. The data indicate that longer/larger hydrocarbon chains provide superior resistance to hydrolysis-induced ring opening.

TABLE 3

Hydrolysis Half-lives of mPEG (5 k-Da) Maleimide Conjugates

| Linker, D | Experimentally Determined Half-lives | |
|---|---|---|
| | pH 9.06 | pH 8.11 |
| 8-TRI; D = trimethylene | 31.4 hours | 17.6 days |
| 8-PEN; D = pentamethylene | — | 28.5 days |
| 8-MCH; D = –⟨cyclohexyl⟩–CH$_2$– | 43.3 hours | — |

Example 9

Synthesis of 1-(N-maleimidomethyl)-4-(methoxy-poly(Ethylene Glycol)Propionamidomethyl)Cyclohexane(Mixture of CIS and Trans isomers)

Step 1.

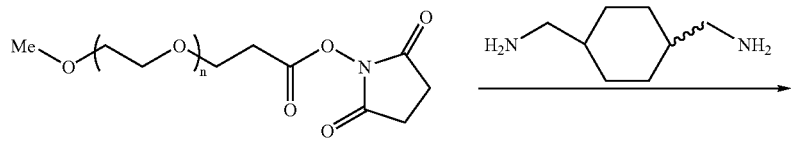

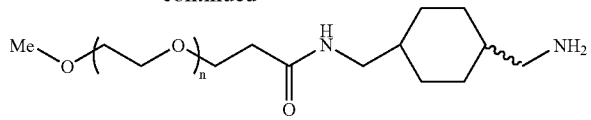

9A. Preparation of 1-aminomethyl-4-(methoxypoly(ethylene glycol)propionamidomethyl)cyclohexane (mixture of cis and trans isomers): N-hydroxysuccimidyl ester of methoxypoly(ethylene glycol)propionic acid, MW 5,000 (20.0 g, 4.0 mmol, Nektar Therapeutics) in acetonitrile (200 mL) was added dropwise to a solution of 1,4-cyclohexane(bismethylamine) (11.34 g, 79.7 mmol) in acetonitrile (200 mL) containing triethylamine (20 mL). This mixture was stirred at room temperature for 3 days. The solvent was removed in vacuo leaving a white solid. The solid was stirred with ether (100 mL), collected by filtration and dried to yield 20.23 g of a crude product. This crude mixture was taken up in $CH_2Cl_2$ (30 mL) and precipitated with IPA (500 mL)/ether (250 mL). The solid was collected by filtration and dried under vacuum (16.3 g).

$^1$H NMR (dmso-$d_6$) δ 7.76 (1H, d, NHC=O), 3.51 (br s, O—$CH_2CH_2$—, PEG backbone), 2.98 and 2.88 (2H, t, C$\underline{H}_2$—NH—C=O), 2.43 and 2.36 (2H, d, C$\underline{H}_2$—$NH_2$), 2.30 (2H, $CH_2C$=O), 1.78-1.68 (1H, m, ring CH), 1.45-1.21 (6H, m, ring methylene protons), 0.90-0.73 (1H, m, ring CH).

Step 2.

9.B. Preparation of 1-(N-maleimidomethyl)-4-(methoxypoly(ethylene glycol)propionamidomethyl)cyclohexane (mixture of cis and trans isomers): A solution of 1-aminomethyl-4-(methoxypoly(ethylene glycol)propionamidomethyl)cyclohexane (mixture of cis and trans isomers) (3.68 g, 0.74 mmol) in $NaHCO_3$ (sat'd, 19 mL) was cooled in an ice/salt/water bath. To this was added N-methoxycarbonylmaleimide (116 mg, 0.82 mmol). This mixture was stirred in the ice bath for 15 minutes and $H_2O$ (29 mL) was added. After stirring in the ice bath for 1 h, the reaction mixture was removed from the bath and stirred at RT for 3 h. The reaction mixture was diluted with brine (30 mL). The pH was adjusted to 3 with 10% phosphoric acid and extracted with $CH_2Cl_2$ (3×50 mL). The combined organic extracts were dried ($Na_2SO_4$) and concentrated in vacuo. The residue was taken up in $CH_2Cl_2$ (10 mL) and precipitated with IPA (60 mL)/ether (100 mL). The product was collected by filtration and dried under vacuum overnight (3.14 g).

$^1$H NMR (dmso-$d_6$) δ 7.79 (1H, d, NHC=O), 7.01 (2H, s, CH=CH), 3.51 (br s, O—$CH_2CH_2$—, PEG backbone), 2.32 (2H, $CH_2C$=O), 1.78-1.45 (2H, m, ring methylene), 1.45-1.21 (5H, m, ring methylene protons and CH), 0.90-0.73 (1H, m, ring protons).

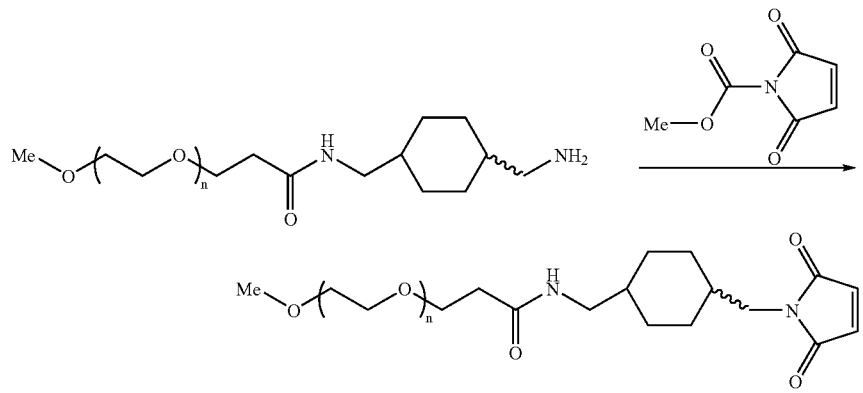

Example 10

Synthesis of Trans-4-(Methoxypoly(Ethylene Glyocol)Propionamidomethyl)-N-cyclohexylmaleimide.

Step 1.

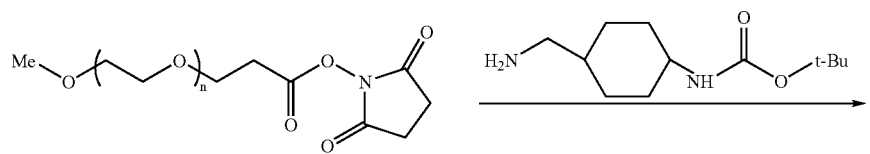

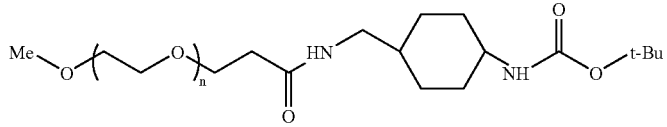

10.A. Preparation of trans-4-(methoxypoly(ethylene glycol)propionamidomethyl)cyclohexyl-t-BOC amine: To a solution of trans-4-aminomethylcyclohexyl-t-BOC-amine (1.0 g, 4.67 mmol, Albany Molecular) and N-hydroxysuccimidyl ester of methoxypoly(ethylene glycol)propionic acid, MW 5,000 (22.9 g, 4.20 mmol, Nektar Therapeutics) in Acetonitrile (200 mL) was added triethylamine (1.2 mL, 8.6 mmol) under Argon. This mixture was stirred at room temperature under an argon atmosphere for 24 h. NMR did not show any remaining protons from the SPA group. The solvent was removed in vacuo to give a white residue which was taken up in CH$_2$Cl$_2$ (60 mL) and precipitated with IPA (500 mL)/ether (1 L). The solid was collected by filtration and dried under vacuum to yield the product as a white solid (22.2 g).

$^1$H NMR (dmso-d$_6$) δ 7.80 (1H, s, CH—NH), 6.70 (1H, d, CH—NH), 3.55 (br s, O—CH$_2$CH$_2$—, PEG backbone), 3.28 (3H, s, CH$_3$), 3.15 (1H, br s, CH), 2.90 (2H, t, CH—CH$_2$—NH), 2.33 (3 H, t, CH$_2$—C=O), 1.74-1.65 (4H, M, ring protons), 1.37 (9 H, s, C(CH$_3$)$_3$), 1.25 (1H, br s, CH), 1.14-0.83 (4 H, m, ring protons).

Step 2.

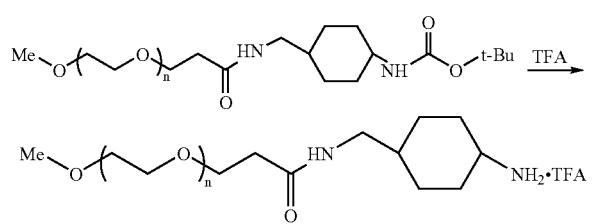

10.B. Preparation of trans-4-(methoxypoly(ethylene glycol)propionamidomethyl)cyclohexylamine, trifluoroacetate. To a solution of trans-4-(methoxypoly(ethylene glycol)propionamidomethyl)cyclohexyl-t-BOC amine (1.20 g, 0.24 mmol) in anhydrous CH$_2$Cl$_2$ (5.0 mL) was added trifluoroacetic acid (2.5 mL, 32.5 mmol). This mixture was stirred at 25° C. for 18 h. The solvent was removed in vacuo leaving an oily residue which was dried overnight under vacuum. The residue was stirred with anhydrous ether (20 mL). The product was collected by filtration followed by drying (0.99 g).

$^1$H NMR (dmso-d$_6$) δ 8.13 (1H, br s, NH), 7.80 (3 H, d, NH$_3$), 3.51 (br s, O—CH$_2$CH$_2$—, PEG backbone and CH), 3.24 (3 H, s, CH$_3$), 2.97 (1 H, br s, CH), 2.27 (2H, t, CH$_2$C=O), 1.95-1.35 (2H, m, cyclohexane protons), 1.34-1.25 (2H, m, cyclohexane protons), 1.40-1.25 (2H, m, cyclohexane protons), 1.25-1.13 (2H, m, cyclohexane protons).

Step 3.

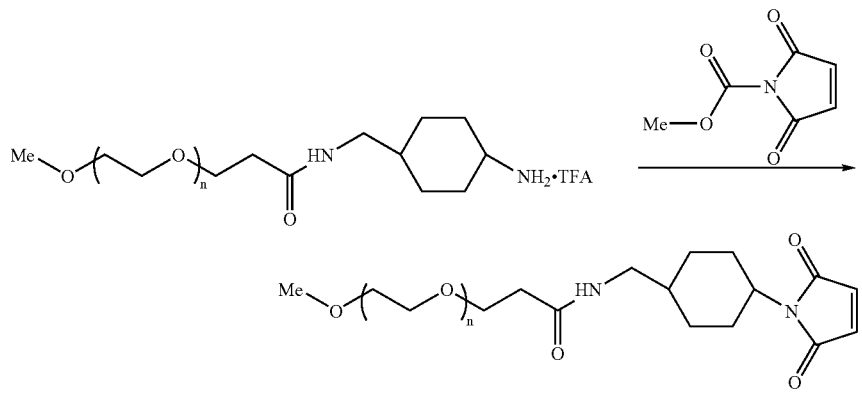

10.B. Preparation of trans-4-(Methoxypoly(ethylene glycol)propionamidomethyl)-N-cyclohexylmaleimide. trans-4-(Methoxypoly(ethylene glycol)propionamidomethyl)cyclohexylamine, trifluoroacetate (3.0 g, 0.60 mmol) was taken up in NaHCO$_3$ (aq, sat'd, 16 mL) and cooled to 2° C. in an ice/salt bath. To this was added N-methoxycarbonyl maleimide (100 mg, 0.70 mmol). After stirring at 2° C. for 15 minutes, H$_2$O (24 mL) was added to the reaction mixture and stirring was continued for 4 h. Brine (50 mL) was added followed by pH adjustment to 3 using 10% Phosphoric acid. This mixture was extracted with CH$_2$Cl$_2$ (3×50 mL). The combined organic extracts were dried (Na$_2$SO$_4$), concentrated in vacuo, and dried under vacuum. $^1$H NMR showed the product to be ca. 50% maleimide/50% ring-opened material, from incomplete ring closure.

$^1$H NMR (dmso-d$_6$) δ 7.80 (1H, d, NH), 6.96 (2 H, s, maleimide CH=CH), 3.51 (474, br s, PEG backbone and CH), 3.24 (3H, s, CH$_3$), 2.89 (2H, t, CH$_2$), 2.30 (2H, t, CH$_2$C=O), 1.85-1.73 (2H, m, cyclohexane protons), 1.73-1.63 (2H, m, cyclohexane protons), 1.32 (1H, br s, CH), 1.15-1.05 (2H, m, cyclohexane protons), 1.00-0.85 (2H, m, cyclohexane protons).

Example 11

Synthesis of Trans-4-(Methoxypoly(Ethyene Glyol)Propionamido)-N-Cyclohexylmaleimide.

Step 1.

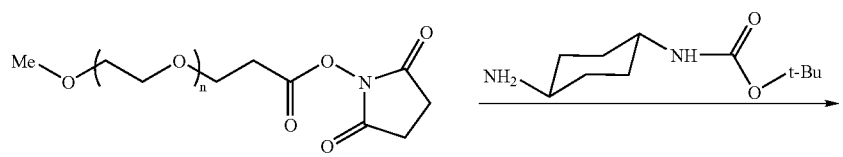

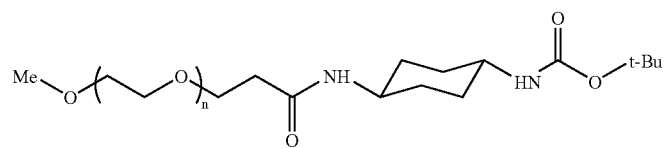

11.A. Preparation of trans-4-(methoxypoly(ethylene glycol)propionamido)cyclohexyl-t-BOC amine: To a solution of mono-t-BOC-trans-1,4-diaminocyclohexane (1.0 g, 4.38 mmol, Albany Molecular) and N-hydroxysuccimidyl ester of methoxypoly(ethylene glycol)propionic acid, MW 5,000 (21.5 g, 4.30 mmol, Nektar Therapeutics) in acetonitrile (200 mL) was added triethylamine (1.2 mL, 8.6 mmol) under Argon. This mixture was stirred at room temperature under an argon atmosphere for 24 h. $^1$H NMR did not show any remaining protons from the N-hydroxysuccinimidyl ester group. The solvent was removed in vacuo to give a white residue which was stirred with ether (50 mL) for 30 minutes. The solid was collected by filtration and dried under vacuum to yield the product as a white solid (1.95 g).

$^1$H NMR (dmso-$d_6$) δ 7.70 (1H, d, CH—NH), 6.69 (1H, d, CH—NH), 3.51 (br s, O—CH$_2$CH$_2$—, PEG backbone and CH), 3.24 (3 H, s, CH$_3$), 3.15 (1H, br s, CH), 2.26 (3 H, t, CH$_2$—C=O), 1.74 (4 H, br d, ring protons), 1.37 (9 H, s, C(CH$_3$)$_3$), 1.17-1.07 (4 H, m, ring protons).

Step 2.

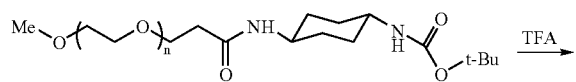

-continued

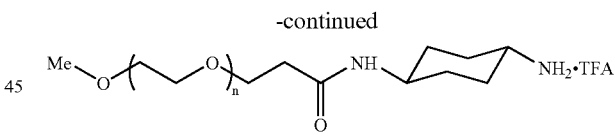

11.B. Preparation of trans-4-(methoxypoly(ethylene glycol)propionamido)cyclohexylamine, trifluoroacetate. To a solution of trans-4-(methoxypoly(ethylene glycol)propionamido)cyclohexyl-t-BOC amine (12.0 g, 2.4 mmol) in anhydrous CH$_2$Cl$_2$ (55 mL) was added trifluoroacetic acid (25 mL, 325 mmol). This mixture was stirred at 25° C. for 18 h. The solvent was removed in vacuo leaving an oily residue which was dried overnight under vacuum. The residue was taken up in CH$_2$Cl$_2$ (30 mL) and precipitated with IPA (750 mL)/ether (500 mL). The product was collected by filtration followed by drying to give the product as a white solid (10.2 g).

$^1$H NMR (dmso-$d_6$) δ 8.13 (1H, br s, NH), 7.80 (3 H, d, NH$_3$), 3.51 (br s, O—CH$_2$CH$_2$—, PEG backbone and CH), 3.24 (3 H, s, CH$_3$), 2.97 (1 H, br s, CH), 2.27 (2H, t, CH$_2$C=O), 1.95-1.35 (2H, m, cyclohexane protons), 1.34-1.25 (2H, m, cyclohexane protons), 1.40-1.25 (2H, m, cyclohexane protons), 1.25-1.13 (2H, m, cyclohexane protons).

Step 3.

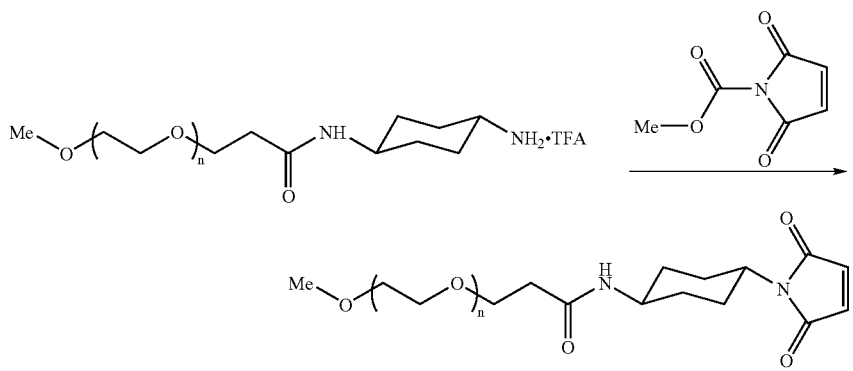

11.C. Preparation of trans-4-(Methoxypoly(ethylene glycol)propionamido)-N-cyclohexylmaleimide. trans-4-(Methoxypoly(ethylene glycol)propionamido)cyclohexylamine, trifluoroacetate (3.0 g, 0.60 mmol) was taken up in NaHCO$_3$ (aq, sat'd, 16 mL) and cooled to 2° C. in an ice/salt bath. To this was added N-methoxycarbonyl maleimide (100 mg, 0.70 mmol). After stirring at 2° C. for 15 minutes, H$_2$O (24 mL) was added to the reaction mixture and stirring was continued for 5 h. Brine (20 mL) was added followed by pH adjustment to 3 using 10% Phosphoric acid. This mixture was extracted with CH$_2$Cl$_2$ (3×50 mL). The combined organic extracts were dried (Na$_2$SO$_4$), concentrated in vacuo, and dried under vacuum to give the product as a white solid (2.75 g). $^1$H NMR showed the product to be 26% maleimide/74% opened material, from incomplete ring closure.

$^1$H NMR (dmso-d$_6$) δ 7.77 (1H, d, NH), 6.96 (2 H, s, maleimide CH=CH), 3.51 (br s, O—CH$_2$CH$_2$—, PEG backbone), 3.24 (3H, s, CH$_3$), 2.28 (2H, t, CH$_2$C=O), 2.06-1.92 (1H, m, cyclohexane proton), 1.88-1.73 (3H, m, cyclohexane protons), 1.59-1.65 (1H, m, cyclohexane proton), 1.28-1.13 (3H, m, cyclohexane protons).

Example 12

Synthesis of 1-N-maleimidomethyl-3-(Methoxypoly(Ethylene Glyol)Propionamidomethyl)Cyclohexane(Mixture of CIS and Trans isomers)

Step 1.

12.A. Preparation of 1-aminomethyl-3-(methoxypoly(ethylene glycol)propionamidomethyl)cyclohexane (mixture of cis and trans isomers): N-hydroxysuccimidyl ester of methoxypoly(ethylene glycol)propionic acid, MW 5,000 (10.0 g, 2.0 mmol, Nektar Therapeutics) in acetonitrile (100 mL) was added dropwise to a solution of 1,3-cyclohexane(bismethylamine) (6.0 mL, 39.9 mmol, Albany Molecular) in acetonitrile (100 mL) containing triethylamine (10 mL). This mixture was stirred at room temperature for 3 days. The insoluble solids were filtered and the filtrate was concentrated in vacuo leaving a white solid. The crude mixture was taken up in CH$_2$Cl$_2$ (50 mL) and precipitated with IPA (375 mL)/ether (300 mL). The solid was filtered to give a white solid which was dried under vacuum (9.5 g). $^1$H NMR showed some remaining 1,3-cyclohexane(bismethylamine) which was removed by dissolving the solid in CH$_2$Cl$_2$ and washing through Amberlyst 15 (15 g). The solvent was removed to give 1-methylamino-3-(methoxypoly(ethylene glycol)propionamidomethyl)cyclohexane (8.62 g).

$^1$H NMR (dmso-d$_6$) δ 7.78 (1H, d, NHC=O), 3.51 (br s, PEG backbone), 3.24 (3H, s, OCH$_3$), 2.95 and 2.89 (2H, m, CH$_2$—NH—C=O), 2.49 and 2.37 (2H, d, CH$_2$—NH$_2$), 2.30 (2H, CH$_2$C=O), 1.75-1.65 (4H, m, ring protons), 1.63-1.21 (2H, m, ring protons), 1.21-1.03 (2H, m, ring protons), 0.80-0.70 (1H, m, ring proton), 0.50-0.30 (1H, m, ring proton).

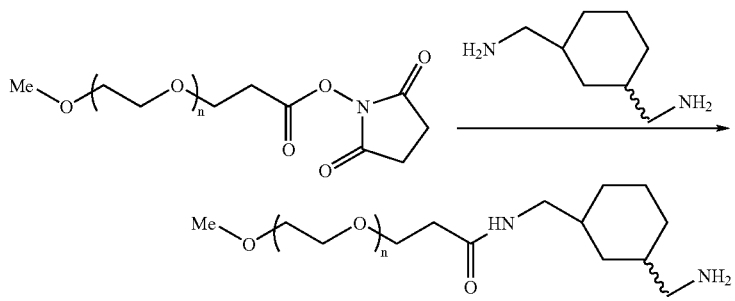

Step 2.

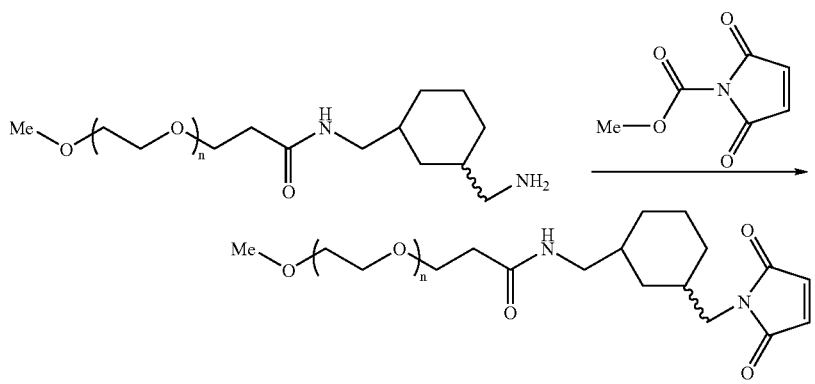

12.B. Preparation of 1-N-maleimidomethyl-3-(methoxypoly(ethylene glycol)propionamidomethyl)cyclohexane (mixture of cis and trans isomers): A solution of 1-aminomethyl-3-(methoxypoly(ethylene glycol)propionamidomethyl) cyclohexane (mixture of cis and trans isomers) (4.0 g, 0.8 mmol) in NaHCO$_3$ (sat'd, 20 mL) was cooled in an ice/salt/water bath. To this was added N-methoxycarbonylmaleimide (126 mg, 0.89 mmol). This mixture was stirred in the ice bath for 15 minutes and H$_2$O (32 mL) was added. After stirring in the ice bath for 1 h, the reaction mixture was removed from the bath and stirred at RT for 3 h. The reaction mixture was diluted with brine (30 mL). The pH was adjusted to 3 with 10% phosphoric acid and extracted with CH$_2$Cl$_2$ (3×50 mL). The combined organic extracts were dried (Na$_2$SO$_4$) and concentrated in vacuo. The residue was dried under vacuum to give the product as a white solid.

$^1$H NMR (dmso-d$_6$) δ 7.79 (1H, d, NHC=O), 7.01 (2H, s, CH=CH), 3.51 (br s, PEG backbone and CHC$\underline{H}_2$), 3.24 (3H, s, OCH$_3$) 3.10-2.63 (2H, m, CHC$\underline{H}_2$), 2.31 (2H, dd CH$_2$C=O), 1.65-1.1.10 (8H, m, ring protons), 0.83-0.48 (2H, m, ring protons).

Example 13

Hydrolysis Rate Study of Exemplary Polymer Maleimides

Hydrolysis studies were conducted on several exemplary stabilized PEG-maleimides as described above in Example 7. The structures of the particular PEG-maleimides and their corresponding half-lives are provided in Table 4 below.

TABLE 4

Stability of Selected mPEG Maleimides

| STRUCTURE | HALF-LIFE, IN HOURS |
|---|---|
| 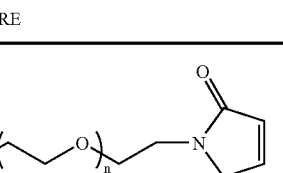 | 8.1 |
| 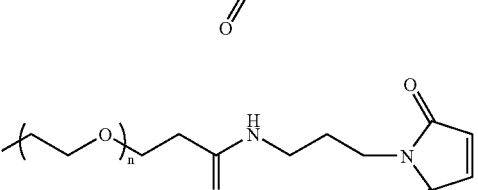 | 11.5 |
| 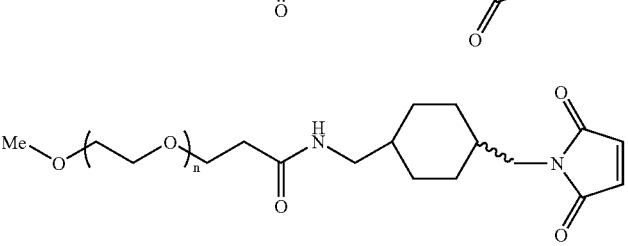 | 20.6 |

TABLE 4-continued

Stability of Selected mPEG Maleimides

| STRUCTURE | HALF-LIFE, IN HOURS |
|---|---|
| 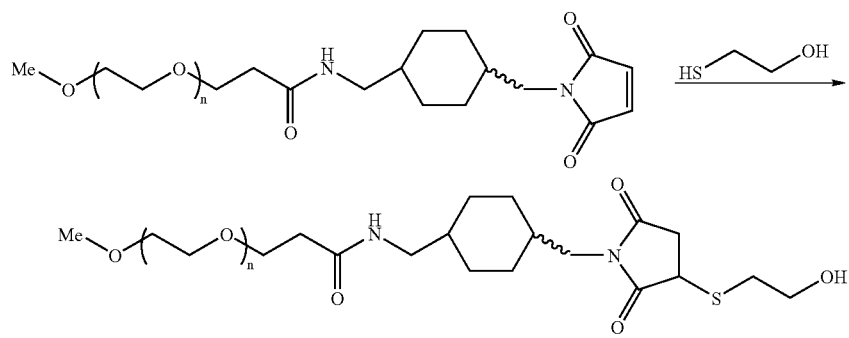 | 64.6 |

Example 14

Conjugation of a Stabilized mPEG-maleimide, 1-(N-maleimidomethyl)-4-(Methoxypoly(Ethylene Glycol)Propionamidomethyl)Cyclohexane, to the Model Compound, 2-mercaptoethanol

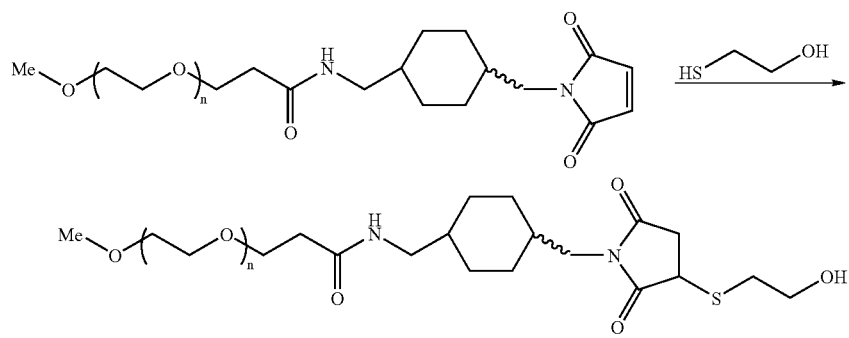

Preparation of 1-(3-(2-hydroxyethanemercapto)-N-succinimidylmethyl)-4-(methoxypoly(ethylene glycol)propionamidomethyl)cyclohexane (mixture of cis and trans isomers) To a solution of 1-(N-maleimidomethyl)-4-(methoxypoly(ethylene glycol)propionamidomethyl) cyclohexane (mixture of cis and trans isomers) (500 mg, 0.1 mmol) in $CH_3CN$ (10 mL) was added 2-mercaptoethanol (15 μL, 0.21 mmol). This mixture was allowed to stir at room temperature for 18 hours. $^1H$ NMR showed remaining maleimide starting material. Additional 2-mercaptoethanol (15 μL, 0.21 mmol) was added and the mixture was stirred for another 24 hours. $^1H$ NMR showed that no remaining maleimide was present. The solvent was removed in vacuo and dried under vacuum. The solid was taken up in $CH_2Cl_2$ (2 mL) and precipitated with IPA (50 mL). The solid was collected by filtration and dried to give the product as a white solid (403 mg).

$^1H$ NMR (dmso-$d_6$) δ 7.66 (1H, br s, NH), 4.83 (1H, t, OH), 4.01 (1H, dd, CH—S), 3.51 (br s, PEG backbone), 3.05-2.61 (4H, m, 2×CH$\underline{H}_2$), 2.30 (2H, t, $CH_2C=O$), 1.75-0.75 (10H, m, ring protons).

Example 15

Conjugation of a Stabilized mPEG-maleimide, Trans-4-(Methoxypoly(Ethylene Glyol)Propionamidomethyl)-N-cyclohexylmaleimide, to the Model Compound, 2-mercaptoethanol

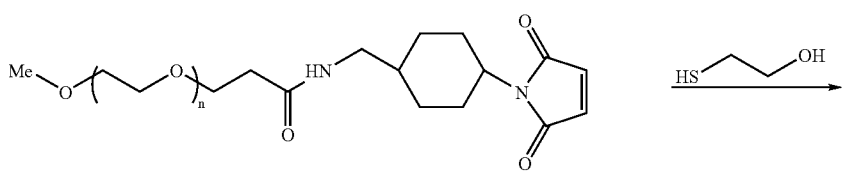

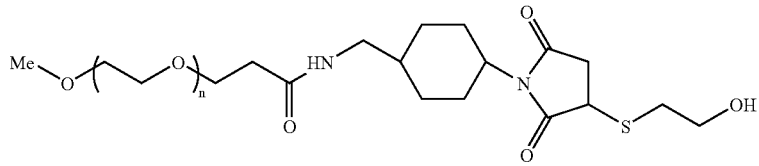

10

Preparation of trans-1-(3-(2-hydroxyethanemercapto)-N-succinimidyl)-4-(methoxypoly(ethylene glycol)propionamidomethyl)cyclohexane: To a solution of trans-4-(methoxypoly(ethylene glycol)propionamidomethyl)-N-cyclohexylmaleimide (400 mg, 0.0.08 mmol) in CH₃CN (10 mL) was added 2-mercaptoethanol (15 µL, 0.21 mmol). This mixture was allowed to stir at room temperature for 18 hours. The solvent was removed in vacuo and dried under vacuum. The residue was stirred with ether (2×20 mL) and the solid collected by filtration to give the product as a white solid (310 mg).

¹H NMR (dmso-d₆) δ 7.81 (1H, br s, NH), 4.87 (1H, t, OH), 3.85 (1H, dd, CH—SEtOH), 3.51 (br s, PEG backbone, CH and SCH₂C$\underline{H}$₂OH), 3.24 (3H, s, CH₃), 2.90 (2H, br s, CH₂NH), 2.79 (2H, t, SC$\underline{H}$₂CH₂), 2.30 (2H, t, CH₂C═O), 2.08-1.55 (5H, m, ring protons), 1.25-0.94 (4H, m, ring protons).

Example 16

Conjugation of a Stabilized mPEG-maleimide, Trans-4-(Methoxypoly(Ethylene Glycol)Propionamido)-N-cyclohexylmaleimide, to the Model Compound, 2-mercaptoethanol Preparation of trans-1-(3-(2-hydroxyethanemercapto)-N-succinimidyl)-4-(methoxypoly(ethylene glycol)propionamido)cyclohexane: To a solution of trans-4-(methoxypoly(ethylene glycol)propionamido)-N-cyclohexylmaleimide (400 mg, 0.0.08 mmol) in CH₃CN (10 mL) was added 2-mercaptoethanol (15 µL, 0.21 mmol). This mixture was allowed to stir at room temperature for 18 hours. The solvent was removed in vacuo and dried under vacuum to give the product as a white solid (240 mg).

¹H NMR (dmso-d₆) δ 7.75 (1H, br s, NH), 4.83 (1H, t, OH), 4.01 (1H, dd, CH—S), 3.51 (br s, PEG backbone and 2×CH), 2.75 (2H, m, S—CH₂), 2.33 (2H, t, CH₂C═O), 2.02-1.65 (4H, m, ring protons), 1.55-0.95 (4H, m, ring protons).

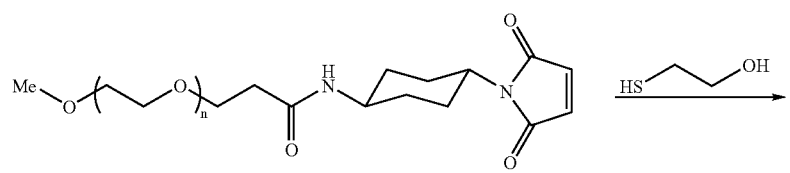

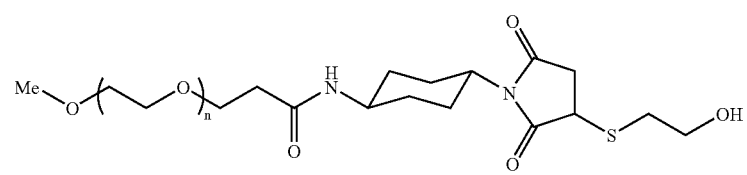

Example 17

Conjugation of a Stabilized mPEG-maleimide, 1-N-maleimidomethyl-3-(Methoxypoly(Ethylene Glycol)Propionamidomethyl)Cyclohexane, to the Model Compound, 2-Mercaptoethanol

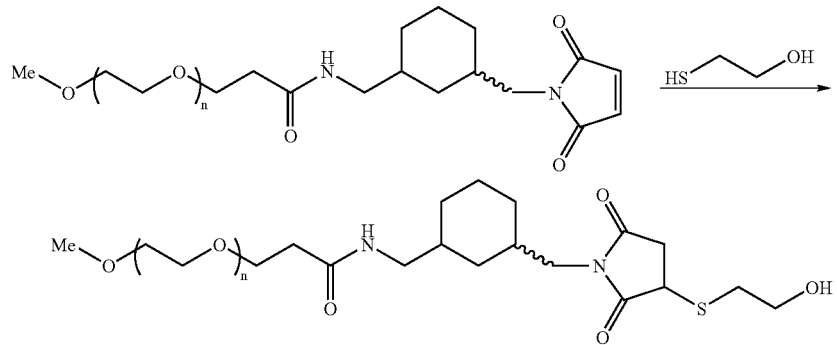

Preparation of 1-(3-(2-hydroxyethanemercapto)-N-succinimidylmethyl)-3-(methoxypoly(ethylene glycol)propionamidomethyl)cyclohexane (mixture of cis and trans isomers): To a solution of 1-N-maleimidomethyl-3-(methoxypoly(ethylene glycol)propionamidomethyl) cyclohexane (mixture of cis and trans isomers) (450 mg, 0.0.09 mmol) in $CH_3CN$ (10 mL) was added 2-mercaptoethanol (15 µL, 0.21 mmol). This mixture was allowed to stir at room temperature for 18 hours. The solvent was removed in vacuo and dried under vacuum. The residue was stirred with ether (20 mL) and the solid collected by filtration to give the product as a white solid (230 mg).

$^1$H NMR (dmso-$d_6$) δ 7.81 (1H, br s, NH), 4.89 (1H, t, OH), 4.03 (1H, dd, CH—S), 3.51 (PEG backbone and S—C$\underline{H}_2$C$\underline{H}_2$), 3.24 (3H, s, CH$_3$), 3.05-2.60 (4H, m, 2×CHC$\underline{H}_2$), 2.30 (2H, t, C$\underline{H}_2$C=O), 1.80-1.05 (8H, m, ring protons), 0.80-0.51 (2H, m, ring protons).

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A conjugate formed by reaction of an active agent comprising a reactive thiol group with a water-soluble polymer having the structure:

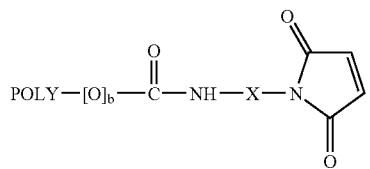

II wherein:
POLY is a water-soluble polymer segment,
b is 0 or 1,
X is a hydrolytically stable linker comprising at least 4 contiguous saturated carbon atoms adjacent to the nitrogen atom of the maleimide ring, and
said polymer is absent aromatic groups and ester linkages.

2. A conjugate comprising the following structure:

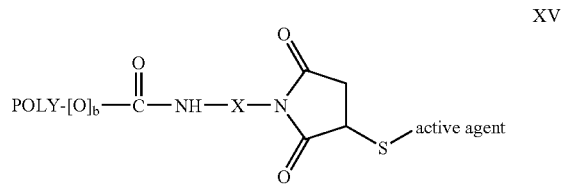

XV wherein:
POLY is a water-soluble polymer segment,
b is 0 or 1,
X is a hydrolytically stable linker comprising at least 4 contiguous saturated carbon atoms adjacent to the ring nitrogen atom,
"POLY-[O]$_b$—C(O)—NH—X—" is absent aromatic groups and ester linkages, and
"—S-active agent" represents a residue of an active agent comprising a thiol (—SH) group.

3. A composition comprising the conjugate of claim 2, wherein said composition comprises a single polymer conjugate species.

4. The conjugate of claim 1, wherein said active agent is selected from the group consisting of small molecules, peptides, and proteins.

5. The conjugate of claim 2, wherein said active agent is selected from the group consisting of small molecules, peptides, and proteins.

6. The conjugate of claim 2, wherein POLY is selected from the group consisting of poly(alkylene oxide), poly(vinyl pyrrolidone), poly(vinyl alcohol), polyoxazoline, poly(acryloylmorpholine), and poly(oxyethylated polyol).

7. The conjugate of claim 6, wherein POLY is a poly(alkylene oxide).

8. The conjugate of claim 7, wherein POLY is a poly(ethylene glycol).

9. The conjugate of claim 8, wherein the poly(ethylene glycol) is terminally capped with an end-capping moiety.

10. The conjugate of claim 9, wherein the end-capping moiety is selected from the group consisting alkoxy, substituted alkoxy, alkenyloxy, substituted alkenyloxy, alkynyloxy, substituted alkynyloxy, aryloxy, and substituted aryloxy.

11. The conjugate of claim 10, wherein the end-capping moiety is selected from the group consisting of methoxy, ethoxy, and benzyloxy.

12. The conjugate of claim 8, wherein the poly(ethylene glycol) has a nominal average molecular mass of from about 100 daltons to about 100,000 daltons.

13. The conjugate of claim 12, wherein the poly(ethylene glycol) has a nominal average molecular mass of from about 1,000 daltons to about 50,000 daltons.

14. The conjugate of claim 13, wherein the poly(ethylene glycol) has a nominal average molecular mass of from about 2,000 daltons to about 30,000 daltons.

15. The conjugate of claim 8, wherein said poly(ethylene glycol) has a structure selected from the group consisting of linear, branched and forked.

16. The conjugate of claim 15, wherein said poly(ethylene glycol) comprises the structure:

Z—(CH$_2$CH$_2$O)$_n$—CH$_2$CH$_2$—, where n is from about 10 to about 4000, and Z comprises a moiety selected from the group consisting of hydroxy, amino, ester, carbonate, aldehyde, aldehyde hydrate, acetal, ketone, ketone hydrate, ketal, alkenyl, acrylate, methacrylate, acrylamide, sulfone, thiol, carboxyl acid, isocyanate, isothiocyanate, hydrazide, urea, maleimide, vinylsulfone, dithiopyridine, vinylpyridine, iodoacetamide, alkoxy, benzyloxy, silane, lipid, phospholipid, biotin, and fluorescein.

17. The conjugate of claim 8, wherein X is a saturated acyclic, cyclic, or alicyclic hydrocarbon chain having a total number of carbon atoms selected from the group consisting of 4, 5, 6, 7, 8, 9, 10, 11, 12, 13, 14, 15, 16, 17, 18, 19, and 20.

18. The conjugate of claim 17, wherein X is a saturated acyclic, cyclic, or alicyclic hydrocarbon chain having a total number of carbon atoms selected from the group consisting of: from 4 to about 12, from 4 to about 10, and from about 5 to about 8 atoms.

19. The conjugate of claim 8, wherein X is a linear saturated acyclic hydrocarbon chain.

20. The conjugate of claim 8, wherein X is a branched saturated acyclic hydrocarbon chain.

21. The conjugate of claim 20, wherein X is branched at the carbon α to the maleimidyl group.

22. The conjugate of claim 20, wherein X is branched at the carbon β to the maleimidyl group.

23. The conjugate of claim 20, wherein X is branched at the carbon γ to the maleimidyl group.

24. The conjugate of claim 19, having the structure:

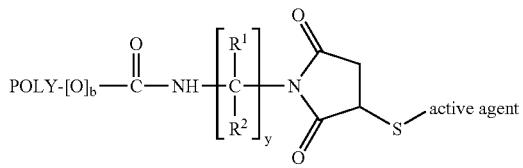

wherein:
y is an integer from 4 to about 20;
R$^1$, in each occurrence, is independently H or an organic radical that is selected from the group consisting of alkyl, substituted alkyl, cycloalkyl, substituted cycloalkyl, alkylenecycloalkyl, and substituted alkylenecycloalkyl, and R$^2$, in each occurrence, is independently H or an organic radical that is selected from the group consisting of alkyl, substituted alkyl, cycloalkyl, substituted cycloalkyl, alkylenecycloalkyl, and substituted alkylenecycloalkyl.

25. The conjugate of claim 24, wherein either (i) R$^1$ and R$^2$ in each occurrence is independently H or an organic radical selected from the group consisting of lower alkyl and lower cycloalkyl or (ii) R$^1$ and R$^2$ are both H, and y is selected from the group consisting of 4, 5, 6, 7, 8, 9, and 10.

26. The conjugate of claim 24 having the structure:

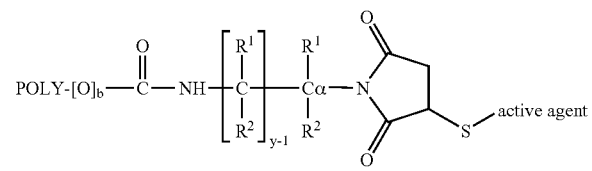

wherein at least one of R$^1$ or R$^2$ on C$_α$ is selected from the group consisting of alkyl, substituted alkyl, cycloalkyl, substituted cycloalkyl, alkylenecycloalkyl, and substituted alkylenecycloalkyl.

27. The conjugate of claim 26, wherein each of R$^1$ and R$^2$ on C$_α$ is independently selected from the group consisting of alkyl, substituted alkyl, cycloalkyl, substituted cycloalkyl, alkylenecycloalkyl, and substituted alkylenecycloalkyl.

28. The conjugate of claim 26, wherein all other non-C$_α$ R$^1$ and R$^2$ variables are H.

29. The conjugate of claim 26 wherein at least one of R$^1$ or R$^2$ on C$_α$ is lower alkyl or lower cycloalkyl.

30. The conjugate of claim 26, wherein R$^2$ on C$_α$ is H.

31. The conjugate of claim 30, wherein R$^1$ on C$_α$ is selected from the group consisting of methyl, ethyl, propyl, isopropyl, butyl, isobutyl, pentyl, cyclopentyl, hexyl, and cyclohexyl.

32. The conjugate of claim 26 having the structure:

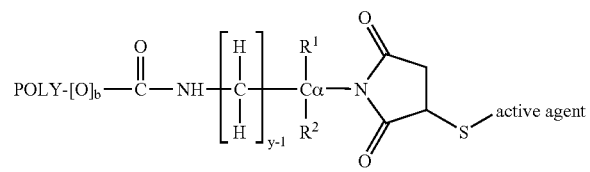

wherein R$^1$ and R$^2$ are each independently alkyl or cycloalkyl.

33. The conjugate of claim 26, having the structure:

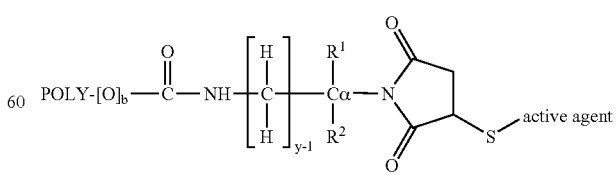

wherein R$^1$ is alkyl or cycloalkyl and R$^2$ is H.

34. The conjugate of claim 32 wherein R$^1$ and R$^2$ are each independently either methyl or ethyl.

35. The conjugate of claim 32, wherein $R^1$ and $R^2$ are the same.

36. The conjugate of claim 22 having the structure:

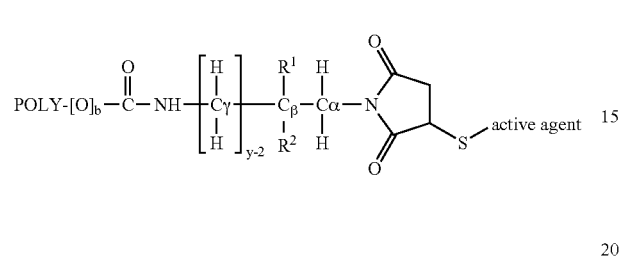

wherein $R^1$ and $R^2$ are each independently selected from the group consisting of H, alkyl, substituted alkyl, cycloalkyl, substituted cycloalkyl, alkylenecycloalkyl, and substituted alkylenecycloalkyl, but are not both H.

37. The conjugate of claim 36, wherein $R^1$ and $R^2$ are each independently H, lower alkyl or lower cycloalkyl.

38. The conjugate of claim 37, wherein $R^1$ and $R^2$ are each independently selected from the group consisting of H, methyl, ethyl, propyl, isopropyl, butyl, isobutyl, pentyl, cyclopentyl, hexyl, and cyclohexyl.

39. The conjugate of claim 36, wherein $R^2$ is H.

40. The conjugate of claim 24, having the structure:

wherein at least one of $R^1$ and $R^2$ attached to $C_\gamma$ is selected from the group consisting of alkyl, substituted alkyl, cycloalkyl, substituted cycloalkyl, alkylenecycloalkyl, and substituted alkylenecycloalkyl.

41. The conjugate of claim 40, wherein at least one of $R^1$ and $R^2$ attached to $C_\gamma$ is alkyl or cycloalkyl and all other $R^1$ and $R^2$ variables are H.

42. The conjugate of claim 40, wherein one of the $R^1$ variables attached to $C_\alpha$ or $C_\beta$ is alkyl or cycloalkyl, and all other $R^1$ and $R^2$ variables are H.

43. The conjugate of claim 2, wherein X is a saturated cyclic or alicyclic hydrocarbon chain.

44. The conjugate of claim 43, wherein X has the structure:

$$\left[\begin{array}{c} R^1 \\ | \\ C \\ | \\ R^2 \end{array}\right]_q - CYC_a - \left[\begin{array}{c} R^1 \\ | \\ C \\ | \\ R^2 \end{array}\right]_p,$$

IV and $CYC_a$ is a cycloalkylene group having "a" ring carbons, where the value of "a" ranges from 3 to 12;

p and q are each independently 0 to 20, and $p+q+a \leqq 20$, $R^1$, in each occurrence, is independently H or an organic radical that is selected from the group consisting of alkyl, substituted alkyl, cycloalkyl, substituted cycloalkyl, alkylenecycloalkyl, and substituted alkylenecycloalkyl, and $R^2$, in each occurrence, is independently H or an organic radical that is selected from the group consisting of alkyl, substituted alkyl, cycloalkyl, substituted cycloalkyl, alkylenecycloalkyl, and substituted alkylenecycloalkyl.

45. The conjugate of claim 44, wherein p and q are each independently selected from the group consisting of 0, 1, 2, 3, 4, 5, 6, 7, and 8.

46. The conjugate of claim 44, wherein $R^1$, in each occurrence, is independently H or an organic radical that is either lower alkyl or lower cycloalkyl, and $R^2$, in each occurrence, is independently H or an organic radical that is either lower alkyl or lower cycloalkyl.

47. The conjugate of claim 44, wherein a is selected from the group consisting of 5, 6, 7, 8 and 9.

48. The conjugate of claim 47, wherein a is 6 and $CYC_a$ is a 1,1-, 1,2-, 1,3- or 1,4-substituted cyclohexyl ring.

49. The conjugate of claim 44, wherein p and q each independently range from 0 to 4.

50. The conjugate of claim 48, wherein the substituents on said substituted cyclohexyl ring are cis.

51. The conjugate of claim 48, wherein the substituents on said substituted cyclohexyl ring are trans.

52. The conjugate of claim 44, wherein $R^1$ and $R^2$ are H in every occurrence.

53. The conjugate of claim 46, having the structure:

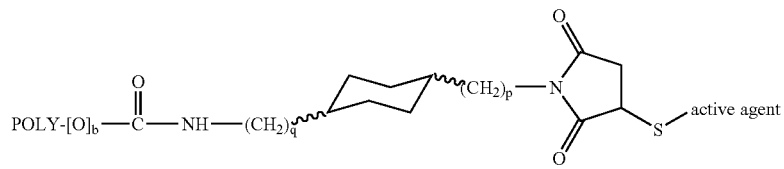

wherein q and p each independently range from 0 to 6.

54. The conjugate of claim 53, wherein q ranges from 0 to 6 and p is zero.

55. The conjugate of claim 46, having the structure:

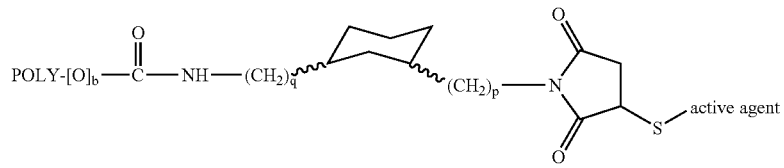

wherein q and p each independently range from 0 to 3, and the substituents on the cyclohexylene ring are either cis or trans.

56. The conjugate of claim 44, wherein $CYC_a$ is bicyclic or tricyclic.

57. The conjugate of claim 56, wherein $CYC_a$ is selected from the group consisting of:

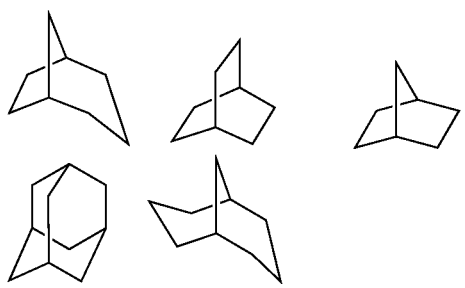

which may include substituents positioned at any available position on the bi or tricyclic ring.

58. The conjugate of claim 2 having the structure:

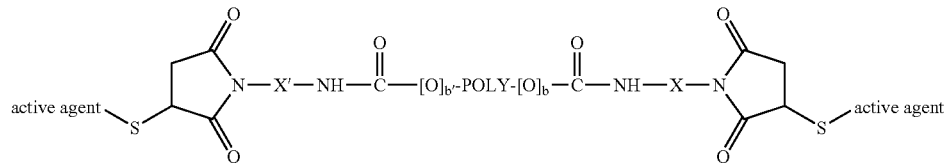

wherein X and b are as previously defined, b' is 0 or 1, and

X' is a hydrolytically stable linker comprising at least 4 contiguous saturated carbon atoms adjacent to the ring nitrogen atom.

59. The conjugate of claim 2, corresponding to the structure:

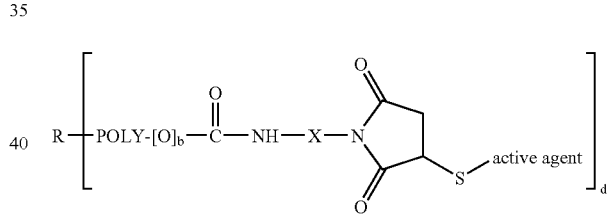

wherein:

d is an integer from 3 to about 100, and

R is a residue of a central core molecule having 3 or more hydroxyl groups, amino groups, or combinations thereof.

60. The conjugate of claim 59, wherein d is an integer from 3 to about 12.

61. The conjugate of claim 1, wherein POLY is a multi-arm polymer segment, and said polymer corresponds to the structure:

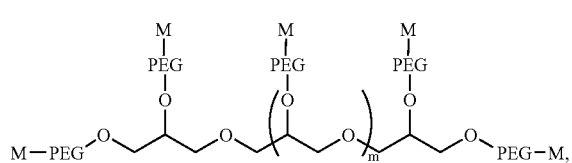
where
PEG is $-(CH_2CH_2O)_nCH_2CH_2-$,
M is:
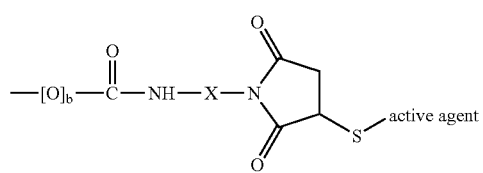
and m is selected from the group consisting of 3, 4, 5, 6, 7, and 8.
* * * * *